United States Patent
Sieffert et al.

(10) Patent No.: US 10,925,809 B2
(45) Date of Patent: Feb. 23, 2021

(54) ORAL DEVICE, ASSEMBLY AND METHOD FOR THE USE THEREOF

(71) Applicant: Trudell Medical International, London (CA)

(72) Inventors: Marcus Sieffert, London (CA); Peter Scarrott, London (CA); Andreas I. Rifani, London (CA)

(73) Assignee: Trudell Medical International, London (CA)

(*) Notice: Subject to any disclaimer, the term of this patent is extended or adjusted under 35 U.S.C. 154(b) by 376 days.

(21) Appl. No.: 15/781,990

(22) PCT Filed: Dec. 6, 2016

(86) PCT No.: PCT/IB2016/057378
§ 371 (c)(1),
(2) Date: Jun. 6, 2018

(87) PCT Pub. No.: WO2017/098404
PCT Pub. Date: Jun. 15, 2017

(65) Prior Publication Data
US 2018/0360692 A1 Dec. 20, 2018

Related U.S. Application Data

(60) Provisional application No. 62/265,088, filed on Dec. 9, 2015.

(51) Int. Cl.
*A61J 7/00* (2006.01)
*A63B 23/03* (2006.01)
(Continued)

(52) U.S. Cl.
CPC ............... *A61J 7/0061* (2013.01); *A61F 5/56* (2013.01); *A61H 9/0007* (2013.01);
(Continued)

(58) Field of Classification Search
CPC ........ A61H 21/00; A61H 23/00; A61H 13/00; A61H 13/005; A61H 9/0007;
(Continued)

(56) References Cited

U.S. PATENT DOCUMENTS 743,866 A 11/1903 Harris
3,118,667 A 1/1964 Barons
(Continued)

FOREIGN PATENT DOCUMENTS

CA 2867440 A1 10/2013
CN 201393517 Y 2/2010
(Continued)

OTHER PUBLICATIONS

Abdelmunim, H. et al., "A 3D Human Database Construction Based on a Point-based Shape Registration," 18th IEEE International Conference on Image Processing, 2011, pp. 1617-1620.
(Continued)

*Primary Examiner* — Colin W Stuart
*Assistant Examiner* — Douglas Y Sul
(74) *Attorney, Agent, or Firm* — Brinks Gilson & Lione

(57) ABSTRACT

A carrying case has first and second clam shell members hingedly connected along one side thereof and defines a interior cavity when in a closed position. At least a portion of an oral device is disposed between the first and second clam shell members with a support member engaging and supporting the oral device such that an intraoral bolus simulator is suspended in the interior cavity free of any engagement with the carrying case. The intraoral bolus simulator may include lubricated patches transformable from a first state, wherein the lubricated patches each comprise water soluble thermoplastic particles suspended in a silicone matrix, to a second state, wherein the water soluble thermoplastic particles are depleted from the silicone
(Continued)

matrix. A method of stimulating an oral cavity includes depleting the water soluble thermoplastic particles from the silicone matrix, and presenting a rough surface to the user with the depleted lubricated patches.

10 Claims, 47 Drawing Sheets

(51) Int. Cl.
*A61F 5/56* (2006.01)
*A61H 21/00* (2006.01)
*A61H 23/00* (2006.01)
*A61H 9/00* (2006.01)
*A61M 13/00* (2006.01)
*A61G 13/00* (2006.01)

(52) U.S. Cl.
CPC .......... *A61H 9/0078* (2013.01); *A61H 21/00* (2013.01); *A61H 23/00* (2013.01); *A61J 7/0053* (2013.01); *A61M 13/003* (2013.01); *A63B 23/032* (2013.01); *A61G 13/00* (2013.01); *A61M 2210/065* (2013.01)

(58) Field of Classification Search
CPC ... A61H 9/0078; A61M 13/003; A61J 7/0053; A61J 7/0061; A63B 230/032; A61C 16/06–066; A61C 2204/007; A61C 7/08; A61C 2202/00; B65D 11/105; B65D 25/10
USPC ................ 128/859–862; 206/63.5, 207–209, 206/361–362.4, 363–368, 372–380; 220/4.22–4.24; 433/6–7
See application file for complete search history.

(56) References Cited

U.S. PATENT DOCUMENTS

| | | |
|---|---|---|
| 3,286,576 A | 11/1966 | West |
| 3,646,628 A | 3/1972 | Halford |
| 3,662,463 A | 5/1972 | Ushkow |
| 3,744,485 A | 7/1973 | Worthy |
| 3,808,686 A | 5/1974 | Tauman |
| 3,867,770 A | 2/1975 | Davis |
| 3,924,850 A | 12/1975 | Robertson |
| 4,170,230 A | 10/1979 | Nelson |
| 4,367,759 A | 1/1983 | Kline |
| 4,401,130 A | 8/1983 | Halford et al. |
| 4,495,944 A | 1/1985 | Brisson et al. |
| 4,519,400 A | 5/1985 | Brenman et al. |
| 4,608,974 A | 9/1986 | Sicurelli, Jr. |
| 4,718,662 A | 1/1988 | North |
| 4,966,580 A | 10/1990 | Turner et al. |
| 4,986,283 A | 1/1991 | Tepper |
| 4,997,182 A | 3/1991 | Kussick |
| 5,066,502 A | 11/1991 | Eales |
| 5,085,634 A | 2/1992 | Lackney |
| 5,133,971 A | 7/1992 | Copelan et al. |
| 5,143,087 A | 9/1992 | Yarkony |
| 5,156,267 A * | 10/1992 | Yates, Jr. ............ A61M 5/3205 206/364 |
| 5,176,151 A | 1/1993 | Harding |
| 5,186,047 A | 2/1993 | Gordon |
| 5,191,014 A | 3/1993 | Roberts et al. |
| 5,213,553 A | 5/1993 | Light |
| 5,260,000 A | 11/1993 | Nandu et al. |
| 5,263,976 A | 11/1993 | Williams |
| 5,268,005 A | 12/1993 | Suhonen |
| 5,288,498 A | 2/1994 | Stanley et al. |
| 5,318,523 A | 6/1994 | Lu |
| 5,379,648 A | 1/1995 | Tiffin |
| 5,445,825 A | 8/1995 | Copelan et al. |
| H1557 H | 7/1996 | Joubert et al. |
| 5,653,229 A | 8/1997 | Greenberg |
| 5,735,772 A | 4/1998 | Schiavoni |
| 5,839,444 A | 11/1998 | Komatsu et al. |
| 5,855,908 A | 1/1999 | Stanley et al. |
| 5,897,492 A | 4/1999 | Feller et al. |
| D411,623 S | 6/1999 | Schiavoni |
| 5,954,673 A | 9/1999 | Stachlin et al. |
| 5,993,413 A * | 11/1999 | Aaltonen ............... A61J 7/0092 604/77 |
| D422,694 S | 4/2000 | Hill |
| 6,326,022 B1 * | 12/2001 | Katz ..................... A61M 31/00 424/435 |
| D461,558 S | 8/2002 | Schiavoni |
| 6,454,788 B1 | 9/2002 | Ashton |
| 6,468,554 B1 | 10/2002 | Ichino |
| 6,581,605 B2 | 6/2003 | Addington et al. |
| 6,591,140 B2 | 7/2003 | Strome et al. |
| 6,595,362 B2 * | 7/2003 | Penney ................. A61M 5/002 206/364 |
| 6,607,549 B2 | 8/2003 | Huang |
| 6,632,095 B2 | 10/2003 | Ryan |
| 6,823,554 B1 | 11/2004 | Braun et al. |
| 6,974,424 B2 | 12/2005 | Fletcher et al. |
| 7,083,548 B1 | 8/2006 | Moore et al. |
| 7,143,462 B2 | 12/2006 | Hohlbein |
| 7,238,144 B2 | 7/2007 | Ferrara |
| 7,238,145 B2 | 7/2007 | Robbins et al. |
| 7,258,311 B2 | 8/2007 | Yen et al. |
| 7,273,327 B2 | 9/2007 | Hohlbein et al. |
| 7,404,403 B2 | 7/2008 | Farrell |
| 7,438,667 B2 | 10/2008 | Robbins et al. |
| 7,527,642 B2 | 5/2009 | VanSkiver et al. |
| 7,606,623 B2 | 10/2009 | Ludlow et al. |
| 7,660,636 B2 | 2/2010 | Castel et al. |
| 7,662,066 B2 | 2/2010 | Ferrara |
| 7,942,782 B2 | 5/2011 | Al-Tawil |
| 8,047,964 B2 | 11/2011 | Al-Tawil |
| 8,517,729 B2 | 8/2013 | Martin et al. |
| 9,855,187 B2 | 1/2018 | Martin et al. |
| 10,603,427 B2 * | 3/2020 | Hasumi ................ A61M 5/00 |
| 2002/0128673 A1 | 9/2002 | Ripich |
| 2003/0205234 A1 | 11/2003 | Bardach et al. |
| 2004/0000054 A1 | 1/2004 | Sommer |
| 2004/0005525 A1 | 1/2004 | Brattesani |
| 2005/0091854 A1 | 5/2005 | Johnson |
| 2005/0103331 A1 | 5/2005 | Wedemeyer |
| 2005/0218022 A1 * | 10/2005 | Cervantes ............. A61F 2/0095 206/363 |
| 2006/0210480 A1 | 9/2006 | Hamdy |
| 2006/0235352 A1 | 10/2006 | Dziewas et al. |
| 2006/0282010 A1 | 12/2006 | Martin et al. |
| 2007/0181144 A1 | 8/2007 | Brown et al. |
| 2008/0077192 A1 | 3/2008 | Harry et al. |
| 2009/0117507 A1 * | 5/2009 | Abolfathi ............. A61C 19/063 433/6 |
| 2009/0188520 A1 | 7/2009 | Brown |
| 2009/0249571 A1 | 10/2009 | Rohrig |
| 2009/0259310 A1 | 10/2009 | Blom |
| 2009/0286237 A1 | 11/2009 | Fitzgerald et al. |
| 2009/0306626 A1 | 12/2009 | Sinha et al. |
| 2009/0306741 A1 | 12/2009 | Hogle et al. |
| 2010/0016908 A1 | 1/2010 | Martin et al. |
| 2010/0055233 A1 | 3/2010 | Macinnis et al. |
| 2010/0119992 A1 | 5/2010 | Satoh et al. |
| 2010/0121224 A1 | 5/2010 | Toyota et al. |
| 2010/0147846 A1 | 6/2010 | Soibel |
| 2011/0125190 A1 | 5/2011 | Rohrig |
| 2011/0130249 A1 | 6/2011 | Mikhailenok et al. |
| 2011/0239470 A1 | 10/2011 | Hemstreet |
| 2011/0282248 A1 | 11/2011 | Martin et al. |
| 2011/0290246 A1 | 12/2011 | Zachar |
| 2013/0047446 A1 | 2/2013 | Leffler |
| 2013/0060281 A1 | 3/2013 | Lam |
| 2013/0296751 A1 * | 11/2013 | Martin ................... A61H 23/00 601/148 |
| 2014/0247702 A1 * | 9/2014 | Gauthier ................. A23G 4/06 368/89 |
| 2017/0007386 A1 * | 1/2017 | Mason ............... A61C 13/0013 |

(56) References Cited

U.S. PATENT DOCUMENTS

FOREIGN PATENT DOCUMENTS

| EP | 0818213 A2 | 1/1998 |
|---|---|---|
| EP | 1055491 B1 | 1/2003 |
| GB | 2159720 B | 12/1985 |
| GB | 2323026 B | 9/1998 |
| JP | 2005-287712 A | 10/2005 |
| JP | 2006-034916 A | 2/2006 |
| JP | 2007-319303 A | 12/2007 |
| JP | 2008-110024 A | 5/2008 |
| JP | 2011/083524 A | 4/2011 |
| JP | 2011/172996 A | 9/2011 |
| WO | WO 99/37270 A1 | 7/1999 |
| WO | WO 2006/036597 A1 | 4/2006 |
| WO | WO 2006/116843 A1 | 11/2006 |
| WO | WO 2007/121065 A2 | 10/2007 |
| WO | WO 2008/048911 A2 | 4/2008 |
| WO | WO 2009/127947 A2 | 10/2009 |
| WO | WO 2012/090507 A1 | 7/2012 |

OTHER PUBLICATIONS

Ada, Louise et al., "Effect of muscle length on strength and dexterity after stroke," Clinical Rehabilitation, vol. 14, 2000, pp. 55-61.

Adams, M.J. et al., "Friction and lubrication of human skin," Tribology Letters, vol. 26, No. 3, Jun. 2007, pp. 239-253.

Addington, Robert W. et al., "Assessing the Laryngeal Cough Reflex and the Risk and the Risk of Developing Pneumonia After Stroke: An Interhospital Comparison," Stroke, vol. 20, 1999, pp. 1203-1207.

Anderson, D.J., "Measurement of Stress in Mastication. I," Journal of Dental Research, vol. 35, 1956, pp. 664-670.

Anderson, D.J., "Measurement of Stress in Mastication. II," Journal of Dental Research, vol. 35, 1956, pp. 671-673.

Baijens, Laura W. et al., "Effects of Therapy for Dysphagia in Parkinson's Disease: Systematic Review," Dysphagia, vol. 24, 2009, pp. 91-102.

Baijens, Laura W. et al., "Rehabilitation Program for Prosthetic Tracheojejunal Voice Production and Swallowing Function Following Circumferential Pharyngolaryngectomy and Neopharyngeal Reconstruction with a Jejunal Free Flap," Dysphagia, vol. 26(1), 2011, published online Apr. 3, 2010, pp. 78-84.

Barritt, Andrew W. et al., "Role of Cerebral Cortex Plasticity in the Recovery of Swallowing Function Following Dysphagic Stroke," Dysphagia, vol. 24, 2009, pp. 83-90.

Barry, M. et al., "Design of dynamic test equipment for the testing of dental implants," Materials and Design, vol. 26, 2005, pp. 209-216.

Bateman, Claire et al., "Adult Dysphagia Assessment in the UK and Ireland: Are SLTs Assessing the Same Factors?," Dysphagia, vol. 22, 2007, pp. 174-186.

Baylow, Hope E. et al., "Accuracy of Clinical Judgment of the Chin-Down Posture for Dysphagia During the Clinical/Bedside Assessment as Corroborated by Videofluroscopy in Adults with Acute Stroke," Dysphagia, vol. 24, 2009, pp. 423-433.

Becker, Regine et al., "Functional Dysphagia Therapy and PEG Treatment in an Clinical Geriatric Setting," Dysphagia, vol. 26(2), 2011, published online Jan. 26, 2010, pp. 108-116.

Bekelis, Kimon et al., "Severe Dysphagia Secondary to Posterior C1-C3 Instrumentation in a Patient with Altantoaxial Traumatic Injury: A Case Report and Review of the Literature," Dysphagia, vol. 25(2), 2010, published online Sep. 30, 2009, pp. 156-160.

Bennett, Janice W. et al., "Sip-Sizing Behaviors in Natural Drinking Conditions Compared to Instructed Experimental Conditions," Dysphagia, vol. 24, 2009, pp. 152-158.

Bhatka, R. et al., "Bolus size unilateral chewing cycle kinematics," Archrives of Oral Biology, vol. 49, 2004, pp. 559-566.

Billard, Aude et al., "Learning human arm movements by imitation: Evaluation of a biologically inspired connectionist architecture," Robotics and Autonomous Systems, vol. 37, 2001, pp. 145-160.

Bogaardt, H.C. et al., "Cross-cultural Adaptation and Validation of the Dutch Version of SWAL-QoL," Dysphagia, vol. 24, 2009, pp. 66-70.

Bollschweiler, Elfriede et al., "Prevalence of Dysphagia in Patients with Gastroesophageal Reflux in Germany," Dysphagia, vol. 23, 2008, pp. 172-176.

Boryor, Andrew et al., "A downloadable meshed human canine tooth model with PDL and bone for finite element simulations," Dental Materials, vol. 25, 2009, pp. e57-e62.

Bourne, Malcolm, "Relation Between Texture and Mastication," Journal of Texture Studies, vol. 35, 2004, pp. 125-143.

Bülow, Margareta et al., "Neuromuscular Electrical Stimulation (NMES) in Stroke Patients with Oral and Pharyngeal Dysfunction," Dysphagia, vol. 23, 2008, pp. 302-309.

Burkhead, Lori M. et al., "Strength-Training Exercise in Dysphagia Rehabilitation: Principles, Procedures, and Directions for Future Research," Dysphagia, vol. 22, 2007, pp. 251-265.

Butler, Susan G. et al., "Preliminary Investigation of Swallowing Apnea Duration and Swallow/Respiratory Phase Relationships in Individuals with Cerebral Vascular Accident," Dysphagia, vol. 22, 2007, pp. 215-224.

Canning, Brendan J., "Encoding of the cough reflex," Pulmonary Pharmacology & Therapeutics, vol. 20, 2007, pp. 396-401.

Canning, Colleen G. et al., "Loss of strength contributes more to physical disability after stroke than loss of dexterity," Clinical Rehabilitation, vol. 18, 2004, pp. 300-308.

Carlson, Matthew L. et al., "Surgical Management of Dysphagia and Airway Obstruction in Patients with Prominent Ventral Cervical Osteophytes," Dysphagia, vol. 26(1), 2011, published online Jan. 23, 2010, pp. 34-40.

Cha, Tae-Hyun et al., "Noninvasive Treatment Strategy for Swallowing Problems Related to Prolonged Nonoral Feeding in Spinal Muscular Atrophy Type II," Dysphagia, vol. 25(3), 2010, published online Jan. 20, 2010, pp. 261-264.

Chang, Chia-Chi et al., "Effects of a feeding skills training programme on nursing assistants and dementia patients," Care of Older People, © 2005, Blackwell Publishing Ltd., pp. 1185-1192.

Chen, Po-Hung et al., "Prevalence of Perceived Dysphagia and Quality-of-Life Impairment in a Geriatric Population," Dysphagia, vol. 24, 2009, pp. 1-6.

Chin, Ronald Y. et al., "Dysphagia After Emergency Intubation: Case Report and Literature Review," Dysphagia, vol. 24, 2009, pp. 105-108.

Clayton, Nicola A. et al., "Management of Dysphagia in Toxic Epidermal Necrolysis (TEN) and Stevens-Johnson Syndrome (SJS)," Dysphagia, vol. 22, 2007, pp. 187-192.

Colodny, Nancy EdD, "Validation of the Caregiver Mealtime and Dysphagia Questionnaire (CMDQ)," Dysphagia, vol. 23, 2008, pp. 47-58.

Coulas, Véronique et al., "Differentiating Effortful and Noneffortful Swallowing with a Neck Force Transducer: Implications for the Development of a Clinical Feedback System," Dysphagia, vol. 24, 2009, pp. 7-12.

Crary, Michael A. PhD et al., "Identification of Swallowing Events from sEMG Signals Obtained from Healthy Adults," Dysphagia, vol. 22, 2007, pp. 94-99.

Crary, Michael A. PhD et al., "Electrical Stimulation Therapy for Dysphagia: Descriptive Results of Two Surveys," Dysphagia, vol. 22, 2007, pp. 165-173.

Crawford, Hannah et al., "Compliance with Dysphagia Recommendations by Carers of Adults with Intellectual Impairment," Dysphagia, vol. 22, 2007, pp. 326-334.

Danneskiold-Samsøe, B. et al., "Isokinetic and isometric muscle strength in a healthy population with special reference to age and gender," Acta Physiol., vol. 197 (Suppl. 673), 2009, pp. 1-68.

Dantas, Roberto Oliveira et al., "Effect of Gender on Swallow Event Duration Assessed by Videofluroscopy," Dysphagia, vol. 24, 2009, pp. 280-284.

Di Domizio, Jennifer et al., "Forearm posture and grip effects during push and pull tasks," Ergonomics, vol. 53, No. 3, Mar. 2010, pp. 336-343.

Dörfer, Christof E. et al., "Factors influencing proximal dental contact strengths," Eur. J. Oral Sci., vol. 108, 2000, pp. 368-377.

(56) References Cited

OTHER PUBLICATIONS

Duizer, L.M. et al., "Instrumental Measures of Bite Forces Associated with Crisp Products," Journal of Texture Studies, vol. 37, 2006, pp. 1-15.

Dyer, Jill C. et al., "Objective Computer-Based Assessment of Valleculae Residue—Is It Useful,?" Dysphagia, vol. 23, 2008, pp. 7-15.

Dziewas, R. et al., "Placing nasogastric tubes in stroke patients with dysphagia: efficiency and tolerability of the reflex placement," J. Neutral Neurosurg. Psychiatry, vol. 74, 2003, pp. 1429-1431.

Easterling, Caryn S. et al., "Dementia and Dysphagia," Geriatric Nursing, vol. 29, No. 4, 2008, pp. 275-285.

Easterling, Caryn, "Does an Exercise Aimed at Improving Swallow Function Have an Effect on Vocal Function in the Healthy Elderly? ," Dysphagia, vol. 23, 2008, pp. 317-326.

Eisenberg, John M. MD et al., "8: Diagnosis and Treatment of Swallowing Disorders (Dysphagia) in Acute-Care Stroke Patients," AHRQ Evidence Reports, Agency for Health Care Policy and Research, U.S. Department of Health and Human Services, ECRI, Plymouth Meeting, Pennsylvania, Jul. 1999, 153 pages.

Emami, Mohammad Hassan et al., "Pneumatic Balloon Dilation Therapy Is as Effective as Esophagomyotomy for Achalasia," Dysphagia, vol. 23, 2008, pp. 155-160.

Engelen, L. et al., "Relating Particles and Texture Perception," Chapter 5, pp. 58-72.

Farahmand, Bahram et al., "Predicting fracture and fatigue crack growth properties using tensile properties," Engineering Fracture Mechanics, vol. 75, 2008, pp. 2144-2155.

Ferrario, Virgilio F. et al., "Maximal bite forces in healthy young adults as predicted by surface electromyography," Journal of Dentistry, vol. 32, 2004, pp. 451-457.

Ferrario, V.F. et al., "Single tooth bite forces in healthy young adults," Journal of Oral Rehabilitation, vol. 31, 2004, pp. 18-22.

Finney, M. et al., "Measurement of Biting Velocities at Predetermined and Individual Crosshead Speed Instrumental Imitative Tests for Predicting Sensory Hardness of Gelatin Gels," Journal of Sensory Studies, vol. 20, 2005, pp. 114-129.

Font, Jean Paul MD et al., "Esophargeal Dysphagia," University of Texas Medical Branch, Department of Otolaryngology, Grand Rounds Presentation, Feb. 6, 2008, 53 pages.

Foster, K.D. et al., "Effect of Texture of Plastic and Elastic Model Foods on the Parameters of Mastication," J. Neurophysiol, vol. 95, 2006, pp. 3469-3479.

Franssen, Oliver et al., "New high modulus silicone elastomer—fiber-reinforced LSR," Rubber World, Jun. 2011, 4 pages.

Frazier, Jacqueline Bolders, "Effect of Tactile Stimulation on Lingual Motor Function in Pediatric Lingual Dysphagia," Dysphagia, vol. 22, 2007, pp. 340-342.

French, Stephen et al., "Recent advances in the physiology of eating," Proceedings of the Nutrition Society, vol. 61, Issue 04, Nov. 2002, pp. 489-496.

Fucile, Sandra et al., "A Contolled-flow Vacuum-free Bottle System Enhances Preterm Infants' Nutritive Sucking Skills," Dysphagia, vol. 24, 2009, pp. 145-151.

Gallagher, Louise et al., "Prescription Drugs and Their Effects on Swallowing," Dysphagia, vol. 24, 2009, 159-166.

Gallas, Syrine et al., "Sensory Transcutaneous Electrical Stimulation Improves Post-Stroke Dysphagic Patients," Dysphagia, vol. 25(4), 2010, published online Oct. 24, 2009, pp. 291-297.

Garcia, Jane Mertz PhD et al., "Serving Temperature Viscosity Measurements of Nectar- and Honey-Thick Liquids," Dysphagia, vol. 23, 2008, pp. 65-75.

Geddes, Donna T. et al., "Ultrasound Imaging of Infant Swallowing During Breast-Feeding," Dysphagia, vol. 25(3), 2010, published online Jul. 22, 2009, pp. 183-191.

Gielo-Perczak, Krystyna, "Mechanical considerations for biomechanical glenohumeral joint modeling," Occupational Ergonomics, vol. 5, 2005, pp. 29-42.

Gomes, Fernanda Rodrigues et al., "Oral and Pharyngeal Transit of a Paste Bolus in Chagas' Disease," Dysphagia, vol. 23, 2008, pp. 82-87.

Gumbley, Freya et al., "Effects of Bolus Volume on Pharyngeal Contact Pressure During Normal Swallowing," Dysphagia, vol. 23, 2008, pp. 280-285.

Hammond, Carol A. Smith et al., "Cough and Aspiration of Food and Liquids Due to Oral-Pharyngeal Dysphagia," Chest, vol. 129,1, Jan. 2006, pp. 154S-168S.

Hammond, Carol Smith, "Cough and Aspiration of Food and Liquids Due to Oral Pharyngeal Dysphagia," Lung, vol. 186 (Suppl 1), 2008, pp. S35-S40.

Han, Tai Ryoon et al., "The Prediction of Persistent Dysphagia Beyond Six Months After Stroke," Dysphagia, vol. 23, 2008, pp. 59-64.

Han, Tai Ryoon et al., "Dysphagia Development after Surgery Unrelated to Laryngeal and Pharyngeal Structures," Dysphagia, vol. 24, 2009, pp. 167-171.

Hanna, Fady et al, "Anthropometric and Demographic Correlates of Dual-Axis Swallowing Accelerometry Signal Characteristics: A Canonical Correlation Analysis," Dysphagia, vol. 25(2), 2010, published online Jun. 3, 2009, pp. 94-103.

Hegland, Karen W. et al., "Volitional control of reflex cough," J. Appl. Physiol., vol. 113, 2012, First published Apr. 5, 2012, pp. 39-46.

Hewitt, Angela MS et al., "Standardized Instrument for Lingual Pressure Measurement," Dysphagia, vol. 23, 2008, pp. 16-25.

Humbert, Ianessa A. PhD et al., "Normal Swallowing and Functional Magnetic Resonance Imaging: A Systematic Review," Dysphagia, vol. 22, 2007, pp. 266-275.

Igarashi, Atsuko et al., "Sensory and Motor Responses of Normal Young Adults During Swallowing of Foods with Different Properties and Volumes," Dysphagia, vol. 25(3), 2010, published online Aug. 13, 2009, pp. 198-206.

Imoto, Yoshimasa et al., "Cough reflex induced by capsaicin inhalation in patients with dysphagia," Acta Oto-Laryngologica, vol. 131, 2011, pp. 96-100.

Inamoto, Yoko et al., "Evaluation of Swallowing Using 320-detector-row Multislice CT. Part II: Kinematic Analysis of Laryngeal Closure during Normal Swallowing," Dysphagia, vol. 26(3), 2011, published online Mar. 5, 2010, pp. 209-217.

Ioakimidis, Ioannis et al., "Food intake and chewing in women," Neurocomputing, vol. 84, 2012, pp. 31-38.

Isaksson, Ulf et al., "Physically violent behavior in dementia care: Characteristics of residents and management of violent situations," Aging & Mental Health, vol. 15, No. 5, Jul. 2011, pp. 573-579.

Isildak, Huseyin et al., "Unusual Manifestations of Bilateral Carotid Artery Dissection: Dysphagia and Hoarseness," Dysphagia, vol. 25(4), 2010, pp. 338-340.

Jaric, Slobodan, "Muscle Strength Testing—Use for Normalisation for Body Size," Sports Med., vol. 32(10), 2002, pp. 615-631.

Jones, B. et al., "ACR Appropriateness Criteria® dysphagia," American College of Radiology, Mar. 2001, 9 pages.

Jones, Harrison N. et al., "Oropharyngeal Dysphagia in Infants and Children with Infantile Pompe Disease," Dysphagia, vol. 25(4), 2010, published online Sep. 10, 2009, pp. 277-283.

Kagaya, Hitoshi et al., "Simple Swallowing Provocation Test Has Limited Applicability as a Screening Tool for Detecting Aspiration, Silent Aspiration, or Penetration," Dysphagia, vol. 25, 2010, pp. 6-10.

Kamegai, Tetsuya et al., "A determination of bit force in northern Japanese children," Eur. J. of Orthodontics, vol. 27, 2005, pp. 53-57.

Kanai, Naoko et al., "Successful Treatment of Pulmonary Aspiration Due to Brain Stem Infarction by Using Cough Exercise Based on Swallowing Scintigraphy: Preliminary Observations," Dysphagia, vol. 24, 2009, pp. 434-437.

Kantor, MacKinlay, "Behold the Brown-Faced Men," The Saturday Evening Post, Sep. 23, 1939, pp. 26, 30, 44, 46, 47, 50, 51 and 54.

Karaman, Emin et al., "Unusual Location of Primary Hydatid Cyst: Soft Tissue Mass in the Parapharyngeal Region," Dysphagia, vol. 26(1), 2011, published online Mar. 4, 2010, pp. 75-77.

(56) References Cited

OTHER PUBLICATIONS

Katsinelos, Panagiotis, MD, PhD. et al., "Congenital Bilateral Pharyngoceles: An Unusual Case of Upper Dysphagia," Dysphagia, vol. 23, 2008, pp. 98-100.
Katsinelos, Panagiotis et al., "Long-term Botulinum Toxin Treatment for Dysphagia Due to Large Epiphrenic Diverticulum in Elderly Patients: A Report of Two Cases," Dysphagia, vol. 24, 2009, pp. 109-113.
Kellen, Patrick M. et al., "Computer-Assisted Assessment of Hyoid Bone Motion from Videofluoroscopic Swallow Studies," Dysphagia, vol. 25(4), 2010, published online Oct. 24, 2009, pp. 298-306.
Kelly, Jennifer et al., "A Qualitative Study of the Problems Surrounding Medicine Administration to Patients with Dysphagia," Dysphagia, vol. 24, 2009, pp. 49-56.
Kennedy, Daniel et al., "Tongue Pressure Patterns During Water Swallowing," Dysphagia, vol. 25, 2010, pp. 11-19.
Kieser, Jules et al., "Measuring Intraoral Pressure: Adaptation of a Dental Appliance Allows Measurement During Function," Dysphagia, vol. 23, 2008, pp. 237-243.
Kim, Youngsun et al., "Maximal Hyoid Displacement in Normal Swallowing," Dysphagia, vol. 23, 2008, pp. 274-279.
Kim, Youngsun et al., "Maximal Hyoid Excursion in Poststroke Patients," Dysphagia, vol. 25, 2010, pp. 20-25.
Kim, Youngsun PhD et al., "Stage Transition Duration in Patients Poststroke," Dysphagia, vol. 22, 2007, pp. 299-305.
Kind, Amy et al., "Omission of Dysphagia Therapies in Hospital Discharge Communications," Dysphagia, vol. 26(1), 2011, published online Jan. 23, 2010, pp. 49-61.
Klatsky, Meyer D.D.S., "Cinephotography and Cinefluorography of the Masticatory Apparatus in Function," American Journal of Orthodontics and Oral Surgery, vol. 25, No. 3, Mar. 1939, pp. 205-210.
Kluin, Karen J. et al., "Dysphagia in elderly men with myasthenia gravis," Journal of the Neurological Sciences, vol. 138, 1996, pp. 49-52.
Koc, Duygu et al., "Bite Force and Influential Factors on Bite Force Measurements: A Literature Review," European Journal of Dentistry, vol. 4, Apr. 2010, pp. 223-232.
Koolstra, J.H. et al., "Dynamics of the Human Masticatory Muscles During a Jaw Open-Close Movement," J. Biomechanics, vol. 30, No. 9, 1997, pp. 883-889.
Koolstra, J.H., "Dynamics of the Human Masticatory System," Crit. Rev. Oral Biol. Med., vol. 13(4), 2002, pp. 366-376.
Kos, Martijn P. et al., "Long-Term Results of External Upper Esophageal Sphincter Myotomy for Oropharyngeal Dysphagia," Dysphagia, vol. 25(3), 2010, published online Sep. 17, 2009, pp. 169-176.
Krause, Eike et al., "Botulinum Toxin a Treatment of Cricopharyngeal Dysphagia After Subarachnoid Hemorrhage," Dysphagia, vol. 23, 2008, pp. 406-410.
Kvist, L. Catharina et al., "Equipment for drug release testing of medicated chewing gums," Journal of Pharmaceutical and Biomedical Analysis, vol. 22, 2000, pp. 405-411.
Lamm, Nyla Claire, et al., A Comment on "Effect of Tactile Stimulation on Lingual Motor Function in Pediatric Lingual Dysphagia," Dysphagia, vol. 22, 2007, pp. 343-352.
Landreneau, Stephen W. et al., "Dysphagia in a patient with Esophageal Intramural Pseudo-diverticulosis," Visible Human Journal of Endoscopy, vol. 10, Issue 1, 2011, 3 pages.
Lang, Ivan M., "Brain Stem Control of the Phases of Swallowing," Dysphagia, vol. 24, 2009, pp. 333-348.
Laubach, Lloyd L., "Chapter VII—Human Muscular Strength," Anthropology Research Project Web Associates, pp. VII-1-VII-55.
Lazenby, Tracy, "The Impact of Aging on Eating, Drinking, and Swallowing Function in People with Down's Syndrome," Dysphagia, vol. 23, 2008, pp. 88-97.
Leach, Chet PhD et al., "Particle size of inhaled corticosteroids: Does it matter?" J. Allergy Clin. Immunol., vol. 124, No. 6, pp. S88-S93.
Leder, Steven B. et al., "Confirmation of No Causal Relationship Between Tracheotomy and Aspiration Status: A Direct Replication Study," Dysphagia, vol. 25, 2010, pp. 35-39.
Lee, Joon et al., "Effects of Age and Stimulus on Submental Mechanomyography Signals During Swallowing," Dysphagia, vol. 24, 2009, pp. 265-273.
Lee, Shin-Jae et al., "Cluster analysis of tooth size in subjects with normal occlusion," American Journal of Orthodontics and Dentofacial Orthopedics, vol. 132, No. 6, Dec. 2007, pp. 796-800.
Leonard, Rebecca et al., "Fluoroscopic Surrogate for Pharyngeal Strength: The Pharyngeal Constriction Ratio (PCR)," Dysphagia, vol. 26(1), 2011, published online Oct. 24, 2009, pp. 13-17.
Leopold, Norman A. et al., "Supranuclear Control of Swallowing," Dysphagia, vol. 25(3), 2010, published online Sep. 3. 2009, pp. 250-257.
Leow, Li Pyn et al., "The Impact of Dysphagia on Quality of Life in Ageing and Parkinson's Disease as Measured by the Swallowing Quality of Life (SWAL-QOL) Questionnaire," Dysphagia, vol. 25(3), 2010, published online Aug. 13, 2009, pp. 216-220.
Leslie, Paula, PhD et al., "Cervical Auscultation Synchronized with Images from Endoscopy Swallow Evaluations," Dysphagia, vol. 22, 2007, pp. 290-298.
Leslie, Paula et al., "People with a Learning Disability and Dysphagia: A Cinderella Population," Dysphagia, vol. 24, 2009, pp. 103-104.
Lever, Teresa E. et al., "The Effect of an Effortful Swallow on the Normal Adult Esophagus," Dysphagia, vol. 22, 2007, pp. 312-325.
Lever, Teresa E. et al., "A Mouse Model of Pharyngeal Dysphagia in Amyotrophic Lateral Sclerosis," Dysphagia, Springer Science & Business Media, Jun. 3, 2009, 15 pages.
Lever, Teresa E. et al., "An Animal Model of Oral Dysphagia in Amyotrophic Lateral Sclerosis," Dysphagia, vol. 24, 2009, pp. 180-195.
Lewis, Jr. James L., "Operator Performance and Localized Muscle Fatigue in a Simulated Space Vehicle Control Task," NASA Technical Memorandum 58220, Jun. 1979, 83 pages.
Lim, Anthony et al., "A Pilot Study of Respiration and Swallowing Integration in Parkinson's Disease: "On" and "Off" Levodopa," Dysphagia, vol. 23, 2008, pp. 76-81.
Logemann, Jeri A., "A Randomized Study Comparing the Shaker Exercise with Traditional Therapy: A Preliminary Study," Dysphagia, vol. 24, 2009, pp. 403-411.
Logemann, Jeri A. et al., "What Information Do Clinicians Use in Recommending Oral versus Nonoral Feeding in Oropharyngeal Dysphagic Patients,?" Dysphagia, vol. 23, 2008, pp. 378-384.
Lundgren, D. et al., "Occlusal force pattern during chewing and biting in dentitions restored with fixed bridges of cross-arch extension," Journal of Oral Rehabilitation, vol. 13, 1986, pp. 57-71.
Lunt, Darin R. et al., "Impact energy absorption of three mouthguard materials in three environments," Dental Traumatology, vol. 26, 2010, pp. 23-29.
Maclean, Julia et al., "Dysphagia Following a Total Laryngectomy: The Effect on Quality of Life, Functioning, and Psychological Well-Being," Dysphagia, vol. 24, 2009, pp. 314-321.
Maclean, Julia et al., "Post-Laryngectomy: It's Hard to Swallow," Dysphagia, vol. 24, 2009, pp. 172-179.
Maeshima, Shinichiro, MD, PhD et al., "Influence of Dysphagia on Short-Term Outcome in Patients with Acute Stroke," Am. J. Phys. Med. Rehabil., vol. 90, No. 4, Apr. 2011, pp. 316-320.
Malandraki, Georgia A. et al., "Age-Related Differences in Laterality of Cortical Activations in Swallowing," Dysphagia, vol. 25(3), 2010, published online Sep. 17, 2009, pp. 238-249.
Marbach, Joseph J. D.D.S., "Phantom bite," Am. J. Orthod., vol. 70, No. 2, Aug. 1976, pp. 190-199.
Martin, Ruth E., "Neuroplasticity and Swallowing," Dysphagia, vol. 24, 2009, pp. 218-229.
Martin-Harris, Bonnie et al., "MBS Measurement Tool for Swallow Impairment-MBSImp: Establishing a Standard," Dysphagia, vol. 23, 2008, pp. 392-405.
Martin-Harris, Bonnie et al., "Erratum to: MBS Measurement Tool for Swallow Impairment—MBSImp: Establishing a Standard," Dysphagia, vol. 25, 2010, p. 79.

(56) References Cited

OTHER PUBLICATIONS

Martino, Rosemary et al., "Perceptions of Psychological Issues Related to Dysphagia Differ in Acute and Chronic Patients," Dysphagia, vol. 25, 2010, pp. 26-34.
Márton, Krisztina et al., "Evaluation of oral manifestations and masticatory force in patients with polymyositis and dermatomyositis," J. Oral Pathol. Med., vol. 34, 2005, pp. 164-169.
Materazzi, S. et al., "Cough Sensors. II. Transient Receptor Potential Membrane Receptors on Cough Sensors," Handbook Exp. Pharmacol., vol. 187, 2009, pp. 49-61.
Mazari, A. et al., "Contribution of the Cheeks to the Intraoral Manipulation of Food," Dysphagia, vol. 22, 2007, pp. 117-121.
McElhiney, Judith et al., "The Mayo Dysphagia Questionnaire-30: Documentation of Reliability and Validity of a Tool for Interventional Trials in Adults with Esophageal Disease," Dysphagia, vol. 25(3), 2010, published online Oct. 24, 2009, pp. 221-230.
McHorney, Colleen A., "Clinical Validity of the SWAL-QOL and SWAL-CARE Outcome Tools with Respect to Bolus Flow Measures," Dysphagia, vol. 23, 2008, p. 461.
McKinstry, Anita et al., "Outcomes of Dysphagia Intervention in a Pulmonary Rehabilitation Program," Dysphagia, vol. 25(2), 2010, published online Jul. 18, 2009, pp. 104-111.
Meng, Han et al., "Anatomical Variations in Stylopharyngeus Muscle Insertions Suggest Interindividual and Left/Right Differences in Pharyngeal Clearance Function of Elderly Patients: A Cadaveric Study," Dysphagia, vol. 23, 2008, pp. 251-257.
Mepani, Rachel et al., "Augmentation of Deglutitive Thyrohyoid Muscle Shortening by the Shaker Exercise," Dysphagia, vol. 24, 2009, pp. 26-31.
Metheny, Norma A., "Preventing Aspiration in Older Adults with Dysphagia," Medsurg Nursing, vol. 15, 2, ProQuest Nursing & Allied Health Source, Apr. 2006, pp. 110.
Miller, Jeri L. et al., "Preliminary Ultrasound Observation of Lingual Movement Patterns During Nutritive versus Non-nutritive Sucking in a Premature Infant," Dysphagia, vol. 22, 2007, pp. 150-160.
Minami, Ichiro et al., "Jaw-movement smoothness during empty chewing and gum chewing," European Journal of Oral Sciences, vol. 120, 2012, pp. 195-200.
Miura, H. et al., "Relationship between cognitive function and mastication in elderly females," Journal of Oral Rehabilitation, vol. 30, 2003, pp. 808-811.
Miyaura, K. et al., "Comparison of biting forces in different age and sex groups: a study of biting efficiency with mobile and non-mobile teeth," Journal of Oral Rehabilitation, vol. 26, 1999, pp. 223-227.
Monroe, Kimberly, "Revisiting the basics of successful ergonomics programs," Ergonomics 101, Industrial Engineer, vol. 38, 3, Mar. 2006, pp. 41-45.
Moore, Jill, "Dysphagia Screening," Integris Stroke Center of Oklahoma, Southwest Medical Center, Acute Physical Medicine Department, Slide presentation, date unknown, 20 pages.
Moriniére, Sylvain et al., "Origin of the Sound Components During Pharyngeal Swallowing in Normal Subjects," Dysphagia, vol. 23, 2008, pp. 267-273.
Murray, Joseph, PhD, "Accuracy of Dysphagia Assessment," VA Ann Arbor, Wayne State University, Detroit, date unknown, 96 pages.
Nagaoka, Keiko, PhD. et al., "Activities of the Muscles Involved in Swallowing in Patients with Cleft Lip and Palate," Dysphagia, vol. 22, 2007, pp. 140-144.
Nakajima, Makoto et al., "Clinical Significance of Oral Intake in Patients with Acute Stroke," Dysphagia, vol. 25(3), 2010, published online Aug. 5, 2009, pp. 192-197.
Neumann, H.H., "Electrical Action Currents During Mastication: Measurement of the Effort Exerted in Chewing Various Foods," Journal of Dental Research, Aug. 1950, Downloaded Mar. 10, 2011, Sage Publications, 7 pages.
Nguyen, C.T. et al., "Mechanics and mechanisms of puncture of elastomer membranes," Journal of Materials Science, vol. 39, 2004, pp. 7361-7364.
Nguyen, C.T. et al., "Puncture characterization of rubber membranes," Theoretical and Applied Fracture Mechanics, vol. 42, 2004, pp. 25-33.
Nguyen, Nam P. et al., "Effectiveness of the Cough Reflex in Patients with Aspiration Following Radiation for Head and Neck Cancer," Lung, vol. 185, 2007, pp. 243-248.
Nguyen, C. Thang et al., "Puncture of elastomer membranes by medical needles. Part I: Mechanisms," Int. J. Fract., vol. 155, 2009, pp. 75-81.
Nguyen, C. Thang et al., "Puncture of elastomer membranes by medical needles. Part II: Mechanics," Int. J. Fract., vol. 155, 2009, pp. 83-91.
Nishimura, T. et al., "Dental hygiene residential care in a 3-year dental hygiene education programme in Japan: towards dysphagia management based on dental hygiene process of care," Int. J. Dental Hygiene, vol. 5, 2007, pp. 145-150.
Okada, Sumiko SLP, MS et al., "What is the Chin-down Posture? A Questionnaire Survey of Speech Language Pathologists in Japan and the United States," Dysphagia, vol. 22, 2007, pp. 204-209.
Okubo, Paula de Carvalho Macedo Issa, MSc et al., "Clinical and Scintigraphic Assessment of Swallowing of Older Patients Admitted to a Tertiary Care Geriatric Ward," Dysphagia, vol. 23, 2008, pp. 1-6.
Okuda, Shinpei et al., "Morphologic Characteristics of Palatopharyngeal Muscle," Dysphagia, vol. 23, 2008, pp. 258-266.
Paine, Peter A. et al., "Modulation of Activity in Swallowing Motor Cortex Following Esophageal Acidification: A Functional Magnetic Resonance Imaging Study," Dysphagia, vol. 23, 2008, pp. 146-154.
Paliwal, Vimal K. et al., "Dysphagia in a Patient with Bilateral Medial Medullary Infarcts," Dysphagia, vol. 24, 2009, p. 349-353.
Pap, J-S. et al., "A robotic human masticatory system: kinematics simulations," Int. J. Intelligent Systems Technologies and Applications, vol. 1, Nos. 1/2, 2005, pp. 3-17.
Parcell, A.C. et al., "An upper arm model for simulated weightlessness," Acta. Physiol. Scand., vol. 169, 2000, pp. 47-54.
Park, Jin-Woo et al., "Effortful Swallowing Training Coupled with Electrical Stimulation Leads to an Increase in Hyoid Elevation During Swallowing," Dysphagia, vol. 24, 2009, pp. 296-301.
Park, Taeok et al., "Initiation and Duration of Laryngeal Closure During the Pharyngeal Swallow in Post-Stroke Patients," Dysphagia, vol. 25(3), 2010, published online Sep. 17, 2009, pp. 177-182.
Payne, Clare et al., "Consistently Inconsistent: Commercially Available Starch-Based Dysphagia Products," Dysphagia, vol. 26(1), 2011, published online Dec. 31, 2009, pp. 27-33.
Pedersen, Morten et al., "Miconazole and Miconazolenitrate Chewing Gum as Drug Delivery Systems—A Practical Application of Solid Dispersion Technique," Drug Development and Industrial Pharmacy, vol. 16(1), 1990, pp. 55-74.
Pedersen, Morten et al., "Miconazole Chewing Gum as a Drug Delivery System Test of Release Promoting Additives," Drug Development and Industrial Pharmacy, vol. 17(3), 1991, pp. 411-420.
Pettigrew, Catharine M. et al., "Dysphagia Evaluation Practices of Speech and Language Therapists in Ireland: Clinical Assessment and Instrumental Examination Decision-Making," Dysphagia, vol. 22, 2007, pp. 235-244.
Pichi, Barbara et al., "Rhabdomyoma of the Parapharyngeal Space Presenting with Dysphagia," Dysphagia, vol. 23, 2008, pp. 202-204.
Pitts, Teresa et al., "Voluntary Cough Production and Swallow Dysfunction in Parkinson's Disease," Dysphagia, vol. 23, 2008, pp. 297-301.
Platteaux, Nele et al., "Dysphagia in Head and Neck Cancer Patients Treated with Chemoradiotheraphy," Dysphagia, vol. 25(2), 2010, published online Aug. 27, 2009, pp. 139-152.
Plesh, Octavia et al., "Effect of Gum Hardness on Chewing Pattern," Experimental Neurology, vol. 92, 1986, pp. 502-512.
Podnos, E. et al., "FEA analysis of silicone MCP implant," Journal of Biomechanics, vol. 39, 2006, pp. 1217-1226.
Power, Maxine L. et al., "Predicting Aspiration After Hemispheric Stroke from Timing Measures of Oropharyngeal Bolus Flow and Laryngeal Closure," Dysphagia, vol. 24, 2009, pp. 257-264.

(56) References Cited

OTHER PUBLICATIONS

Raadsheer, M.C. et al., "Human jaw muscle strength and size in relation to limb muscle strength and size," Eur. J. Oral Sci., vol. 112, 2004, pp. 398-405.
Regan, Julie et al., "Immediate Effects of Thermal-Tactile Stimulation on Timing of Swallow in Idiopathic Parkinson's Disease," Dysphagia, vol. 25(3), 2010, published online Aug. 26, 2009, pp. 207-215.
Reynolds, Eric W. et al., "Variability of Swallow-associated Sounds in Adults and Infants," Dysphagia, vol. 24, 2009, pp. 13-19.
Riecker, Axel et al., "Dysphagia Due to Unilateral Infarction in the Vascular Territory of the Anterior Insula," Dysphagia, vol. 24, 2009, pp. 114-118.
Roberts, D.F. et al., "Arm Strength and Body Dimensions," Human Biology, vol. 31:4, Dec. 1959, pp. 334-343.
Rogers, Sharon D. et al., "Cognitive Impairment and Effects on Upper Body Strenght of Adults With Dementia," J. Aging and Physical Activity, vol. 16, 2008, pp. 61-68.
Roubeau, Bernard PhD et al., "Use of Reaction Time in the Temporal Analysis of Normal Swallowing," Dysphagia, vol. 23, 2008, pp. 102-109.
Rydwik, E. et al., "Muscle strength testing with one repetition maximum in the arm/shoulder for people aged 75+—test-retest reliability," Clinical Rehabilitation, vol. 21, 2007, pp. 258-265.
Sakamoto, Kiwako et al., "Effect of Mastication on Human Brain Activity," Anti-Aging Medicine, vol. 7(13), 2010, pp. 153-160.
Sasaki, Clarence T. et al., "Comments on Selected Recent Dysphagia Literature," Dysphagia, vol. 19, 2004, pp. 60-63.
Sasaki, Clarence T. et al., "Comments on Selected Recent Dysphagia Literature," Dysphagia, vol. 22, 2007, pp. 161-164.
Sasaki, Clarence T. et al., "Comments on Selected Recent Dysphagia Literature," Dysphagia, vol. 22, 2007, pp. 276-279.
Sasaki, Clarence T. et al., "Comments on Selected Recent Dysphagia Literature," Dysphagia, vol. 22, 2007, pp. 335-339.
Sasaki, Clarence T. et al., "Comments on Selected Recent Dysphagia Literature," Dysphagia, vol. 23, 2008, pp. 208-212.
Sasaki, Clarence T. et al., "Comments on Selected Recent Dysphagia Literature," Dysphagia, vol. 23, 2008, pp. 213-218.
Sasaki, Clarence T. et al., "Comments on Selected Recent Dysphagia Literature," Dysphagia, vol. 23, 2008, pp. 413-419.
Sasaki, Clarence T. et al., "Comments on Selected Recent Dysphagia Literature," Dysphagia, vol. 24, 2009, pp. 119-125.
Sasaki, Clarence T. et al., "Comments on Selected Recent Dysphagia Literature," Dysphagia, vol. 24, 2009, pp. 249-255.
Sasaki, Clarence T. et al., "Comments on Selected Recent Dysphagia Literature," Dysphagia, vol. 24, 2009, pp. 362-367.
Sasaki, Clarence T. et al., "Comments on Selected Recent Dysphagia Literature," Dysphagia, vol. 24, 2009, pp. 441-446.
Sasaki, Clarence T. et al., "Comments on Selected Recent Dysphagia Literature," Dysphagia, vol. 25, 2010, pp. 73-78.
Sasaki, Clarence T. et al., "Comments on Selected Recent Dysphagia Literature," Dysphagia, vol. 25, 2010, pp. 265-270.
Schindler, Antonio et al., "Rehabilitative Management of Oropharyngeal Dysphagia in Acute Care Settings: Data from a Large Italian Teaching Hospital," Dysphagia, vol. 23, 2008, pp. 230-236.
Seo, Na Jin et al., "Effects of handle orientation, gloves, handle friction and elbow posture on maximum horizontal pull and push forces," Ergonomics, vol. 53, No. 1, Jan. 2010, pp. 92-101.
Seo, Han Gil et al., "Longitudinal Changes of the Swallowing Process in Subacute Stroke Patients with Aspiration," Dysphagia, vol. 26(1), 2011, published online Jan. 8, 2010, pp. 41-48.
Shaker, Reza, "Editorial: The 15$^{th}$ Anniversary of the Dysphagia Research Society and Establishment of the 'Endowment for the Future'," Dysphagia, vol. 23, 2008, p. 101.
Shimada, A. et al., "Measurement of dynamic bite force during mastication," Journal of Oral Rehabilitation, vol. 39, 2012, pp. 349-356.
Slavicek, G., "Human mastication," J. Stomat. Occ. Med., vol. 3, 2010, pp. 29-41.
Slavicek, G. et al., "Analysis of human mastication behavior: a new approach using planar calculations of fragmented chewing sequences," J. Stomat. Occ. Med., vol. 3, 2010, pp. 61-67.
Sokoloff, Alan J. et al., "Myosin Heavy-Chain Composition of the Human Hyoglossus Muscle," Dysphagia, vol. 25(2), 2010, published online Jun. 13, 2009, pp. 81-93.
Speyer, Renée et al., "Effects of Therapy in Oropharyngeal Dysphagia by Speech and Language Therapists: A Systematic Review," Dysphagia, vol. 25, 2010, pp. 40-65.
Stec, Sebastian et al., "High-Resolution Esophageal Manometry with with ECG Monitoring for Management of Premature Ventricular Complexes-Associated Dysphagia," Dysphagia, vol. 25, 2010, pp. 66-69.
Steele, Catriona M. et al., "The Dynamics of Lingual-Mandibular Coordination During Liquid Swallowing," Dysphagia, vol. 23, 2008, pp. 33-46.
Strassburg, Julia et al., "Geometrical resolution limits and detection mechanisms in the oral cavity," Journal of Biomechanics, vol. 40, 2007, pp. 3533-3540.
Stuart, Sheela et al., "Viscosity in Infant Dysphagia Management: Comparison of Viscosity of Thickened Liquids Used in Assessment and Thickened Liquids Used in Treatment," Dysphagia, vol. 24, 2009, pp. 412-422.
Stübgen, Joerg-Patrick, "Facioscapulohumeral Muscular Dystrophy: A Radiologic and Manometric Study of Pharynx and Esophagus," Dysphagia, vol. 23, 2008, pp. 341-347.
Suiter, Debra M. et al., "Clinical Utility of the 3-ounce Water Swallow Test," Dysphagia, vol. 23, 2008, pp. 244-250.
Abella, Amanda et al., "How to Reuse Daily Contact Lenses," eHow, http://www.ehow.com/how_7455972_reuse-daily-contact-lenses.html, reviewed Sep. 2012, retrieved online Nov. 21, 2013, 2 pages.
Arnold, Dr. M.A. (Toby), "Arnold's Glossary of Anatomy," The University of Sydney, Jun. 2010, 49 pages.
Baba, K. et al. "Society for Oral Physiology Store Kro Group", Journal of Oral Rehabilitation, vol. 29, 2002, pp. 872-889.
Bishop, Eric et al., "Multi-Component Molding of Liquid Silicone Rubber Over Thermoplastics", Medical Silicone Conference, Anaheim, Nov. 3-4, 2010, 54 pages.
Chan, Simon Y.P. et al., "Changes in Arterial Oxygen Saturation ($SaO_2$) Before, During, and After Meals in Stroke Patients in a Rehabilitation Setting", Dysphagia, vol. 24, 2009, pp. 77-82.
Constantino, Paul J. et al., "Tooth chipping can reveal the diet and bite force of fossil hominins" Biol. Lett., vol. 6, 2010, pp. 826-829.
Davies, C.N., "Inhaled Particles", Edited by W.H. Walton, 1971, pp. xvi + viii + 1090, Two volumes, Unwin Brothers, Old Woking, Book Reviews, pp. 213-221.
Demura, Shinich et al., "The Difference in Output Properties Between Dominant and Nondominant Limbs as Measured by Various Muscle Function Tests," Journal of Strength and Conditioning Research, vol. 24, No. 10, pp. 2816-2820.
Dolnikov, Y.I., "Experimental research on the movements in the large joint of arm," Central Scientific Research Institute of Prosthetics and Orthopedic Appliances, 1964, 13 pages.
Duarte Silva, Luiz Filipe et al., "Are There Any Differences Between Nutcracker Esophagus With and Without Reflux?," Dysphagia, vol. 22, 2007, pp. 245-250.
Ergun, Gulch in A. MD, "Swallowing Disorders and Dysphagia," Chapters 1 and 2, date unknown but prior to at least Mar. 28, 2013, 13 pages.
Etter, Jean-Francois, "Electronic cigarettes: a survery of users," BMC Public Health, vol. 10, 2010, 7 pages.
Frank, F.C. et al., "On the theory of Hertzian fracture," Proceedings of the Royal Society of London, Series A, Mathematical and Physical Sciences, © 1967, pp. 291-306.
Frunza, Mihai Catalin et al., "Cusp radius measurement through digital image analysis," Acta Odontologica Scandinavica, vol. 71, 2013, pp. 236-240.
Goldberg, Jon A., "Viscoelastic Properties of Silicone, Polysulfide, and Polyether Impression Materials," Journal of Dental Research, vol. 5, No. 53, 1974, pp. 1033-1039.

(56) References Cited

OTHER PUBLICATIONS

Higgins, Johanne et al., "The effect of a task-oriented intervention on arm function in people with stroke: a randomized controlled trial," Clinical Rehabilitation, vol. 20, 2006, pp. 296-310.

Hutchings, Scott C., "Oral processing of heterogeneous foods," A thesis presented in partial fulfillment of the requirements for the Ph.D. in Food Science at Massey Univ., NZ, 2011, 266 pages.

Hutchings, Scott C. et al., "Mastication of heterogeneous foods: Peanuts inside two different food matrices," Food Quality and Preferences, vol. 22, 2011, pp. 332-339.

Hutchinson, Matt et al., "A Brief Atlas of the Human Body," Copyright1989, Pearson Education, Inc. publishing as Benjamin Cummings, San Francisco, CA, 28 pages.

Imai, E. et al., "Effect of Physical Properties of Food Particles on the Degree of Graininess Perceived in the Mouth," Journal of Texture Studies, vol. 30, 1999, pp. 59-88.

Klompen, Edwin TJ, "Mechanical properties of solid polymers—Consultative modeling of long and short term behavior," Technische Universiteit Eindhoven, 2005, 155 pages.

Koolstra, J.H. et al., "Application and Validation of a Three-Dimensional Mathematical Model of the Human Masticatory System In Vivo," J. Biomechanics, vol. 25, No. 2, 1992, pp. 175-187.

Koolstra, J.H. et al., Three-dimensional dynamical capabilities of the human masticatory muscles, Journal of Biomechanics, vol. 32, 1999, pp. 145-152.

Kothari, M. et al., "Force and complexity of tongue task training influences behavioral measures of motor learning," European Journal of Oral Sciences, vol. 119, 2011, pp. 1-8.

Kothari, M. et al., "Influence of the ability to roll the tongue and tongue-training parameters on oral motor performance and learning," Archives of Oral Biology, vol. 56, 2011, pp. 1419-1423.

Kumar, Shrawan, "Muscle Strength," CRS Press, © 2004, ISBN 0-415-36953-3, 24 pages.

Langdon, Claire, "Dysphagia and Respiratory Infections in Acute Ischemic Stroke," Acute Ischemic Stroke, Jan. 2012, pp. 80-100.

Larian, Babak, M.D., "Swallowing Problems (Dysphagia)," http://www.larianmd.com/areas-of-practice/voice-swallowing.html, © 2012, retrieved from the Internet Dec. 13, 2013, 5 pages.

Lawn, B.R., "Partial cone crack formation in a brittle material loaded with a sliding spherical indenter," Proceedings of the Royal Society of London, Series A, Mathematical and Physical Sciences, © 1967, pp. 307-316.

Liedberg, Birgitta, DDS et al., "Oral Bolus Kneading and Shaping Measured with Chewing Gum," Dysphagia, vol. 10, 1995, pp. 101-106.

Litonjua, Luis A. et al., "An assessment of stress analyses in the theory of abfraction," Bio-Medical Materials and Engineering, vol. 14, 2004, pp. 311-321.

Lowell, Soren Y. et al., "Sensory stimulation activates both motor and sensory components of the swallowing system," NeuroImage, vol. 42, 2008, pp. 285-295.

Miah, Khosru, "Silicone Hydrogels: manufacturing the future today," Acryate Research & Development Ltd., Technical Paper #A843001, Oct. 2006, 1 page.

Miner, John, "Chewing Gum It's Good for You," London Free Press, published prior to at least Mar. 28, 2013, 1 page.

Mizuko, Mark et al., "Identification of Swallowing Patterns Associated with Dysphagia," University of Minnesota Duluth, http://www.d.umn.edu/csd/video/swallowing.htm, © 1998, last modified Mar. 25, 2011, retrieved from the Internet Dec. 13, 2013, 3 pages.

Mountain, Gary et al., "Bite force measurement in children with primary dentition," International Journal of Pediatric Dentistry, vol. 21, 2011, pp. 112-118.

Naitove, Matthew H., "Do's and Don'ts for Overmolding Liquid Silicone onto Thermoplastics," Plastics Technology, vol. 56(3), Mar. 2010, pp. 26-27.

Newman, Anne B., MD, MPH et al., "Strength and Muscle Quality in a Well-Functioning Cohort of Older Adults: The Heath, Aging and Body Composition Study," JAGS, vol. 51, 2003, pp. 323-330.

Nishinari, Katsuyoshi, "Rheology, Food Texture and Mastication," Journal of Texture Studies, vol. 35, 2004, pp. 113-124.

Nohara, Kanji DDS, PhD et al., "Power Spectra Analysis of Levator Veli Palatini Muscle Electromyogram During Velopharyngeal Closure for Swallowing, Speech, and Blowing," Dysphagia, vol. 22, 2007, pp. 135-139.

Paik, Nam-Jong, "Dysphagia," http://www.emedicine.medscape.com/article/324096-overview, May 29, 2012, retrieved from the Internet Dec. 13, 2013, 5 pages.

Pileicikiene, Gaivile et al, "The Human Masticatory System From a Biomechanical Perspective: A Review," Stomatologija, Baltic Dental and Maxillofacial Journal, vol. 6, 2004, pp. 81-84.

Rosiak, Janusz M. et al., "Radiation Formation of Hydrogels for Biomedical Applications," Institute of Applied Radiation Chemistry, Technical University of Lodz, Poland, 1995, 50 pgs.

Roylance, David, "Engineering Viscoelasticity," Dept. of Materials Science and Engineering, MIT, Oct. 2001, 37 pages.

Saitoh, Eiichi, MD, DMSc et al., "Chewing and Food Consistency: Effects on Bolus Transport and Swallow Initiation," Dysphagia, vol. 22, 2007, pp. 100-107.

Schimmel, M. et al., "Masticatory Function and Bite Force in Stroke Patients," Journal of Dental Research, vol. 90, 2011, pp. 230-234.

Simon, Josh, "Effects of Testing Parameters on Pinch Test Results for Hydrophilic Coatings," Biocoat, Inc. Slideshow Presentation, Published prior to at least Mar. 28, 2013, 36 pages.

Simon, Josh, "Hydrophilic Coatings: Consideration for product development and choice," Technical White Paper, www.biocoat.com, published prior to at least Mar. 28, 2013, 8 pages.

Smith, Marianne et al., "Behaviors Associated with Dementia," AJN, vol. 105, No. 7, 2005, pp. 40-52.

Sothmann, M.S. et al., "Performing requirements of physically strenuous occupations: validating minimum standards for muscular strength and endurance," Ergonomics, vol. 47, No. 8, Jun. 2004, pp. 864-875.

Tassinari, Carlo Alberto et al., "Biting Behavior, Aggression, and Seizures," Epillepsia, vol. 46(5), 2005, pp. 654-663.

Theurer, Julie A. et al., "Effects of Oropharyngeal Air-Pulse Stimulation on Swallowing in Healthy Older Adults," Dysphagia, vol. 24, 2009, pp. 302-313.

Thomis, M.A.I. et al., "Inheritance of static and dynamic arm strength and some of its determinants," Acta Physiol. Scand., vol. 163, 1998, pp. 59-71.

Thompson, C.L. et al., The Influence of Experimental Manipulations on Chewing Speed During In Vivo Laboratory Research in Tufted Capuchins (*Cebus apella*), American Journal of Physical Anthropology, vol. 145, 2011, pp. 402-414.

Thralow, Joan Ungerecht, BS, OTR et al., "Activities of daily living and cognitive levels of function in dementia," The American Journal of Alzheimer's Care and Related Disorders & Research, Sep./Oct. 1993, pp. 14-19.

Tighe, Brian et al., "Silicone hydrogels—What are they and how should they be used in everyday practice," Contact Lens Monthly, vol. 218, No. 5726, Nov. 1999, pp. 31-35.

Tippett, Donna C., Tracheotomy: Airway Management, Communication and Swallowing, $2^{nd}$ ed., Edited by Eugene N. Myers and Jonas T. Johnson, Dysphagia, vol. 24, 2009, pp. 246-248.

Troche, Michelle S. et al., "Effects of Bolus Consistency on Timing and Safety of Swallow in Patients with Parkinson's Disease," Dysphagia, vol. 23, 2008, pp. 26-32.

Tsumori, Nobuaki et al., "Morphologic Characteristics of the Superior Pharyngeal Constrictor Muscle in Relation to the Function During Swallowing," Dysphagia, vol. 22, 2007, pp. 122-129.

Unknown author, "Oral-B® Indicator® Toothbrush," http://www.dentalcare.com/en-US/oral-b-crest-professional-products/category/manual-toothbrushes/oralb-indicator.aspx, 2002, retrieved online Nov. 26, 2013, 1 page.

Unknown author, "Chewing Gum (How Products are Made)," Gale Cengage, How Products are Made, www.enotes.com/topics/chewing-gum, 2002, retrieved online Nov. 21, 2013, 6 pages.

Unknown author, "Safety Razor (How Products are Made)," Gale Cengage, How Products are Made, www.enotes.com/topics/safety-razor, 2002, retrieved online Nov. 21, 2013, 6 pages.

(56) References Cited

OTHER PUBLICATIONS

Unknown author, "Socioeconomics," Wikipedia, http://en.wikipedia.org/wiki/Socioeconomics, reviewed Sep. 1012, retrieved online Nov. 21, 2013, 4 pages.

Unknown author, "PDI Lemon Glycerin Swabsticks," © 2009 Quick Medical—Medical Equipment and Supplies, www.quickmedical.com/pdi/lemon-glycerin-swabstikcs.html, retrieved online Nov. 22, 2013, 2 pages.

Unknown author, "Flavored Tongue Depressors," © 2013, Super Duper® Publications, Greenville, SC, www.superduper.com/products/view.aspx?stid=171, retrieved online Nov. 22, 2013, 2 pages.

Unknown author, "Specification for 'Babies' elastomeric feeding bottle teats'," British Standard, BSi, BS 7368:1990, © 1990, 10 pages.

Unknown author, "Dental implants—Guidelines for developing dental implants," Technical Report, International Organization for Standardization (ISO) TR11175, Aug. 1993, 8 pages.

Unknown author, "Flavored Medical Gloves," Southpaw Enterprises®, Inc., www.southpawenterprises.com/OralMotor/FlavoredMedicalGloves.asp, retrieved online Nov. 26, 2013, 1 page.

Unknown author, "Commercial Life Science Products & Services," SAFC, © 2013 Sigma-Aldrich Co. LLC, www.sigmaaldrich.com/safc.html, retrieved online Nov. 26, 2013, 2 pages.

Unknown author, "Dentistry—Implants—Dynamic fatigue test for endosseous dental implants," International Standard, International Organization for Standardization (ISO) 14801, Nov. 2007, 13 pages.

Unknown author, "Roles of Speech-Language Pathologists in Swallowing and Feeding Disorders: Technical Report," American Speech-Language-Hearing Association, DOI 10.1044/policy. TR2001-00150, Dysphagia Document Review and Working Group, © 2001, 31 pages.

Unknown author, "Human Integration Design Handbook (HIDH)," NASA Handbook, BASELINE, Washington, DC, Jan. 2010, 1,136 pages.

Unknown author, "Child use and care articles—Soother holder—Safety requirements and test methods," British Standard, BSi, BS EN 12586:2007, © 2011, European Committee for Standardization, 56 pages.

Unknown author, "Liquid Silicones Boast High Tear Strength," Plastics Technology, vol. 53(11), Nov. 2007, p. 29.

Unknown author, "Dysphagia—The trouble with swallowing," Mayo Clinic Health Letter, vol. 28, No. 10, Oct. 2010, 3 pages.

Unknown author, "Standard Practice for Conditioning Plastics for Testing," ASTM International, Designation: D618-08, Mar. 2011, 4 pages.

Unknown author, "Standard Test Method for Tensile Properties of Plastics," ASTM International, Designation: D638-10, Mar. 2011, 16 pages.

Unknown author, "Standard Test Method for Tear Strength of Conventional Vulcanized Rubber and Thermoplastic Elastomers," ASTM International, Designation: D624-00, Mar. 2011, 9 pages.

Unknown author, "Standard Test Method for Compressive Properties of Rigid Plastics," ASTM International, Designation: D695-10, Mar. 2011, 7 pages.

Unknown author, "Standard Test Methods for Flexural Properties of Unreinforced and Reinforced Plastics and Electrical Insulating Materials," ASTM International, Designation: D790-10, Mar. 2011, 11 pages.

Unknown author, "Standard Test Method for Tensile Properties of Thin Plastic Sheeting," ASTM International, Designation: D882-10, Mar. 2011, 16 pages.

Unknown author, "Standard Test Method for Bearing Strength of Plastics," ASTM International, Designation: D953-10, Mar. 2011, 6 pages.

Unknown author, "Standard Test Method for Tear Resistance (Graves Tear) of Plastic Film and Sheeting," ASTM International, Designation: D1004-09, Mar. 2011, 4 pages.

Unknown author, "Standard Terminology Relating to Rubber," ASTM International, Designation: D1566-10, Mar. 2011, 15 pages.

Unknown author, "Standard Test Method for Propagation Tear Resistance of Plastic Film and Thin Sheeting by Pendulum Method," ASTM International, Designation: D1922-09, Mar. 2011, 7 pages.

Unknown author, "Standard Test Method for Tear-Propagation Resistance (Trouser Tear) of Plastic Film and Thin Sheeting by a Single-Tear Method," ASTM International, Designation: D1938-08, Mar. 2011, 4 pages.

Unknown author, "Standard Method for Puncture-Propagation Tear Resistance of Plastic Film and Thin Sheeting," ASTM International, Designation: D2582-09, Mar. 2011, 5 pages.

Unknown author, "Standard Specification for Poly(Vinyl Chloride) (PVC) Plastic Drain, Waste, and Vent Pipe and Fittings," ASTM International, Designation: D2665-10, Mar. 2011, 7 pages.

Unknown author, "Standard Test Method for Strength Properties of Adhesively Bonded Plastic Lap-Shear Sandwich Joints in Shear by Tension Loading," ASTM International, Designation: D3164-03, Mar. 2011, 4 pages.

Unknown author, "Standard Practice for Injection Molding Test Specimens of Thermoplastics Molding and Extrusion Materials," ASTM International, Designation: D3641-10a, Mar. 2011, 9 pages.

Unknown author, "Standard Test Method for Rubber Property-Extension Cycling Fatigue," ASTM International, Designation: D4482-07, Mar. 2011, 9 pages.

Unknown author, "Standard Test Method for Chip Impact Strength of Plastics," ASTM International, Designation: D4508-10, Mar. 2011, 6 pages.

Unknown author, "Standard Practice for Compression Molding Thermoplastic Materials into Test Specimens, Plaques, or Sheets," ASTM International, Designation: D4703-10a, Mar. 2011, 12 pages.

Unknown author, "Standard Test Methods for Rubber-Measurement of Processing Properties Using Capillary Rheometry," ASTM International, Designation: D5099-08, Mar. 2011, 8 pages.

Unknown author, "Standard Practice for Determining Physical Properties of Fabrics, Yarns, and Sewing Thread Used in Inflatable Restraints," ASTM International, Designation: D5446-08, 5 pages.

Unknown author, "Standard Test Method for Determining the Charpy Impact Resistance of Notched Specimens of Plastics," ASTM International, Designation: D6110-10, Mar. 2011, 17 pages.

Unknown author, "Standard Practice for Cutting Film and Sheeting Test Specimens," ASTM International, Designation: D6287-09, Mar. 2011, 3 pages.

Unknown author, "Standard Test Method for High Speed Puncture Properties of Plastic Films Using Load and Displacement Sensors," ASTM International, Designation: D7192-10, Mar. 2011, 8 pages.

Unknown author, "Standard Practice for Strain-Controlled Fatigue Testing," ASTM International, Designation: E606-04, Mar. 2011, 16 pages.

Unknown author, "Standard Test Method for Measurement of Fatigue Crack Growth Rates," ASTM International, Designation: E647-08, Mar. 2011, 45 pages.

Unknown author, "Standard Guide for Time-Intensity Evaluation of Sensory Attributes," ASTM International, Designation: E1909-97, Mar. 2011, 15 pages.

Unknown author, "Standard Test Method for Odor or Flavor Transfer or Both from Rigid Polymeric Packaging," ASTM International, Designation: E2609-08, Mar. 2011, 10 pages.

Unknown author, "Standard Classification for Vinyl Chloride Plastics Used in Biomedical Application," ASTM International, Designation: F665-09, Mar. 2011, 4 pages.

Unknown author, "Standard Practice for Care and Use of Athletic Mouth Protectors," ASTM International, Designation: F697-00, Mar. 2011, 2 pages.

Unknown author, "Standard Guide for Silicone Elastomers, Gels, and Foams Used in Medical Applications Part II-Crosslinking and Fabrication," ASTM International, Designation: F2042-00, Mar. 2011, 7 pages.

Unknown author, "Standard Specification for Poly(Vinyl Chloride) (PVC) Plastic Drain, Waste, and Vent (DWV) Pipe and Fittings Having Post-Industrial Recycle Content," ASTM International, Designation: F2390-07, Mar. 2011, 7 pages.

Unknown author, "Standard Guide for Developing and Selecting Wear Tests," ASTM International, Designation: G190-06, Mar. 2011, 5 pages.

(56) References Cited

OTHER PUBLICATIONS

Unknown author, "Guidance for Industry and Food and Drug Administration Staff—Factors to Consider When Making Benefit-Risk Determinations in Medical Device Premarket Approval and De Novo Classifications," DHHS, FDA, Centers for Devices and Radiological Health, Centers for Biological Evaluation and Research, Mar. 2012, 55 pages.
Unknown author, "Title 21—Food and Drugs—Chapter 1—Food and Drug Administration—Department of Health and Human Services—Subchapter B—Food for Human Consumption (Continued)," Code of Federal Regulations, Title 21, vol. 3, Revised as of Apr. 1, 2011.
Unknown author, "4a Humanscale™ Human Strenght," Designed by Henry Dreyfuss Associates, published prior to at least Mar. 28, 2013, 5 pages.
Unknown author, "Lubricious Hydrophilic Coatings for Medical Devices," Biocoat Incorporated. www.biocoat.com, © 2013, retrieved online Nov. 26, 2013, 2 pages.
Unknown author, "Contolled Surface, Controlled Process," Plasma Technology Systems, www.plasmatechsystems.com, © 2013, retrieved online Nov. 26, 2013, 1 page.
Unknown author, "Ice Finger," AliMed, www.alimed.com/ice-finger.html, © 2013, retrieved online Nov. 26, 2013, 1 page.
Unknown author, Dysphagia Message Board, www.healthboards.com/boards/dysphagia, © 1998-2013, retrieved online Nov. 26, 2013, 2 pages.
Unknown author, Oral-B® Indicator Toothbrush, Oral-B, www.oralb.com/products/indicator-toothbrush.aspx, retrieved online Nov. 21, 2013, 1 page.
Unknown author, "Reducing Disability From Stroke in the Great Lakes Region," National Association of Chronic Disease Directors, published prior to at least Mar. 28, 2013, 1 page.
Unknown author, "Overmolding Guide," GLS Corporation, © 2004, 18 pages.
Unknown author, Oral Swab 6 information sheet, www.punktura.ro/medicalsupply/Oral_Swab_6_inch_Plastic_Individually_Wrapped_Flavored_Latex_Free_Case.460705985.php, published prior to at least Mar. 28, 2013, 1 page.
Unknown author, "Child use and care articles—Drinking equipment—Part 1: General and mechanical requirements and tests," European Standard EN 14350-1, European Committee for Standardization, Aug. 2004, 24 pages.
Unknown author, "Child use and care articles—Drinking equipment—Part 2: Chemical requirements and tests," European Standard EN 14350-2, European Committee for Standardization, Aug. 2004, 21 pages.
Unknown author, "Methods for Sampling and Testing Gelatine (physical and chemical methods)," BSI, British Standards Institution, BS 757 : 1975, © 1975, 34 pages.
Unknown author, "Child use and care articles—Soothers for babies and young children—Part 1: General Safety requirements and product information," BSI, British Standards Institution, BS EN 1400-1:2002, Oct. 2002, 30 pages.
Unknown author, "Child use and care articles—Soothers for babies and young children—Part 2: Mechanical requirements and tests," BSI, British Standards Institution, BS EN 1400-2:2002, Oct. 2002, 30 pages.
Unknown author, "Child use and care articles—Soothers for babies and young children—Part 3: Chemical requirements and tests," BSI, British Standards Institution, BS EN 1400-3:2002, Oct. 2002, 18 pages.
Unknown author, "The Design Guide for Bonding Rubber and Thermoplastic Elastomers," Locite, vol. 2 2/05, Henkel Corporation, 2005, 78 pages.
Unknown author, "Lemon Glycerin Swabsticks," Medline Industries, Inc., http://www.medline.com/sku/item/MDPMD090600, retrieved from the Internet on Dec. 13, 2013, published prior to at least Mar. 28, 2013, 1 page.
Unknown author, ARK's Oro-Navigator™, ARK Therapeutic Services, Inc., http://www.arktherapeutic.com/ONAVIxxAR.html, retrieved from the Internet on Dec. 13, 2013, published prior to at least Mar. 28, 2013, 2 pages.
Unknown author, ARK's DnZ-Vibe©, ARK Therapeutic Services, Inc., http://www.arktherapeutic.com/DnZV100CAR.html, retrieved from the Internet on Dec. 13, 2013, published prior to at least Mar. 28, 2013, 3 pages.
Unknown author, ARK's Bite-n-Chew Tip Combo, ARK Therapeutic Services, Inc., http://www.arktherapeutic.com/ZVBC400SAR.html, retrieved from the Internet on Dec. 13, 2013, published prior to at least Mar. 28, 2013, 2 pages.
Unknown author, "Chewy Tubes," http://chewytubes.com/products/chewy-tubes/, retrieved from the Internet on Dec. 13, 2013, published prior to at least Mar. 28, 2013, 2 pages.
Unknown author, "How TheraSIP Works," TheraSIP Swallowing Treatment, http://therasip.com/index.cfm/fuseaction/howitworks.index, retrieved from the Internet on Dec. 13, 2013, © 2010, 3 pages.
Unknown author, "Lab: Testing for the Presence of Organic Compounds—'Spit & Chew'," National Association of Chronic Disease Directors, published prior to at least Mar. 28, 2013, 4 pages.
Unknown author, "Statement on Standard Practice for Infection Prevention and Control Instruments for Tracheal Intubation," Committee of Origin: Committee on Quality Management and Departmental Administration (QMDA), Oct. 20, 2010, 1 page.
Unknown author, "Pharynx and Larynx," http://www.emory.edu/ANATOMY/AnatomyManual/pharynx.html, retrieved from the Internet on Dec. 13, 2013, published prior to at least Mar. 28, 2013, 8 pages.
Unknown author, "Identification of Swallowing Patterns Associated with Dysphagia," UM Technology Enhanced Learning Project Description, http://www.d.umn.edu/csd/video/nhoney.htm, retrieved from the Internet on Dec. 13, 2013, published prior to at least Mar. 28, 2013, 2 pages.
Unknown author, picture of Esophagus, http://www.meddean.luc.edu/lumen/meded/Radio/curriculum/ENT, retrieved from the Internet on Dec. 13, 2013, published prior to at least Mar. 28, 2013, 1 page.
Unknown author, "Deglutition," Netter Medical Images, http://www.netterimages.com/images/2125.htm, © 2005-2012, Elsevier, retrieved from the Internet on Dec. 13, 2013, 2 pages.
Utanohara, Yuri et al., "Standard Values of Maximum Tongue Pressure Taken Using Newly Developed Disposable Tongue Pressure Measurement Device," Dysphagia, vol. 23, 2008, pp. 286-290.
Van der Bilt, A. et al., "Oral physiology and mastication," Physiology and Behavior, vol. 89, 2006, pp. 22-27.
Various authors, "Society for Oral Physiology—Store Kro Group," Twenty-Second Biennial Meeting, Jun. 7-10, 2001, Lugano, Switzerland, Abstract of Selected Presentations, Journal of Oral Rehabilitation, vol. 29, 2002, pp. 872-889.
Various authors, "Dysphagia Research Society," Seventeenth Annual Dysphagia Research Society Meeting, Mar. 4-7, 2009, New Orleans, Dysphagia, vol. 24, 2009, pp. 449-460.
Verin, E. et al., "Poststroke Dysphagia Rehabilitation by Repetitive Transcranial Magnetic Stimulation: A Noncontrolled Pilot Study," Dysphagia, vol. 24, 2009, pp. 204-210.
Viana Silva, Ana Cristina et al., "A Scintigraphic Study of Oral, Pharyngeal, and Esophageal Transit in Patients with Stroke," Dysphagia, vol. 23, 2008, pp. 165-171.
Voss, Sarah J., "Two-Shot Silicone—Thermoplastic Medical Molding," Saint-Gobain Performance Plastics, published prior to at least Mar. 28, 2013, 7 pages.
Wakasugi, Yoko et al., "Screening Test for Silent Aspiration at the Bedside," Dysphagia, vol. 23, 2008, pp. 364-370.
Waller, Dave, "ARM's strength," Management Today, vol. 49, May 2007, 6 pages.
Wang, Jing et al., "Improved Adhesion of Silicone Rubber to Polyurethane by Surface Grafting," Journal of Applied Polymer Science, vol. 121, 2011, pp. 1245-1253.

(56) References Cited

OTHER PUBLICATIONS

Warren-Forward, Helen et al., "Australian Speech-Language Pathologists' Knowledge and Practice of Radiation Protection While Performing Videofluoroscopic Swallowing Studies," Dysphagia, vol. 23, 2008, pp. 371-377.

Weers, Jeffry G. et al., "Design of fine particles for pulmonary drug delivery," Expert Opinion Drug Delivery, vol. 4(3), 2007, pp. 297-313.

Weijenberg, R.A.F. et al., "Mastication for the mind—The relationship between mastication and cognition in ageing and dementia," Neuroscience and Biobehavioral Reviews, vol. 35, 2011, pp. 483-497.

Wheeler, Karen M. PhD et al., "Surface Electromyographic Activity of the Submental Muscles During Swallow and Expiratory Pressure Threshold Training Tasks," Dysphagia, vol. 22, 2007, pp. 108-116.

White, Kevin T. et al., "Fatigue Analysis Before and After Shaker Exercise: Physiologic Tool for Exercise Design," Dysphagia, vol. 23, 2008, pp. 385-391.

Willett, Lisa L. MD et al., "An Unusual Cause of Chronic Cough," Case Report, J. Gen. Intern. Med., vol. 21, 2005, pp. C1-C3.

Woda, A. et al., "Development and validation of a mastication simulator," Journal of Biomechanics, vol. 43, 2010, pp. 1667-1673.

Wu, Xin et al., "Wide-mouthed Sacculation of the Esophagus: A Cause of Dysphagia after Radiation Therapy," Dysphagia, vol. 25(4), 2010, published online Mar. 4, 2010, pp. 341-344.

Xu, Weilang et al., "Mastication Robots—Biological Inspiration to Implementation," @ 2010, Springer-Verlag, Berlin, Heidelberg, ISBN 978-3-540-83902-3, DOI 10.1007/978-3-540-93903-0, Library of Congress Control No. 2010928433, 301 pages.

Yagi, Saiko et al., "Involvement of Sensory Input from Anterior Teeith in Deglutitive Tongue Function," Dysphagia, vol. 23, 2008, pp. 221-229.

Yang, Feng et al., "An algorithm for simulating human arm movement considering the comfort level," Simulation Modeling Practice and Theory, vol. 13, 2005, pp. 437-449.

Yang, Xinghao et al., "Release Kinetics of Catechins from Chewing Gum," Journal of Pharmaceutical Sciences, vol. 93, No. 2, Feb. 2004, pp. 293-299.

Yokoi, Teruo et al., "Investigation of Eating Actions of People with Dementia From the Viewpoint of Self-Awareness," American Journal of Alzheimer's Disease and Other Dementias, vol. 27, 2012, pp. 228-237.

Yoshida, Ryo, "Self-Oscillating Gel as Novel Biomimetic Materials," Proceedings of the $14^{th}$ International Symposium on Recent Advances in Drug Delivery Systems, Journal of Controlled Release, vol. 140, Issue 3, Dec. 2009, pp. 333-348.

Youmans, Scott R. et al., "Differences in Tongue Strength Across Age and Gender: Is There a Diminished Strength Reserve?" Dysphagia, vol. 24, 2009, pp. 57-65.

Zimmerman, Jack E. et al., "Swallowing Dysfunction in Acutely Ill Patients," Physical Therapy, vol. 61, No. 12, Dec. 1981, pp. 1755-1763.

Živko-Babić, J. et al., "Bite Force in Subjects with Complete Dentition," Coll. Antropol., vol. 26, 2002, pp. 293-302.

International Search Report and Written Opinion of the International Searching Authority for International Application No. PCT/IB2013/000568, dated Aug. 16, 2013, 13 pgs.

Notification of Reason for Rejection from Japanese Application No. 2011-504558, dated Jun. 4, 2013, 4 pages.

European Search Report for European Patent Application No. EP 15182751 dated on Nov. 27, 2015 (9 pages).

International Search Report for related International Application No. PCT/IB2016/057378, dated Feb. 17, 2017, 3 pgs.

\* cited by examiner

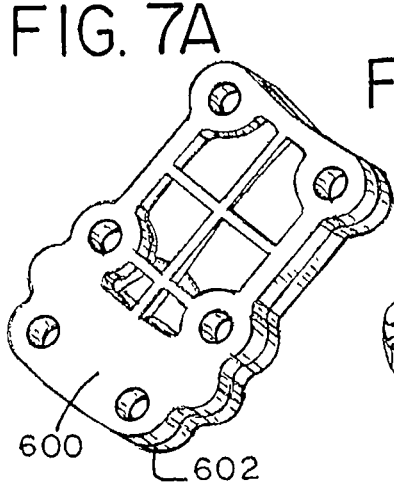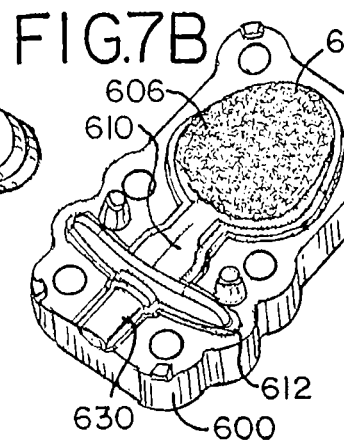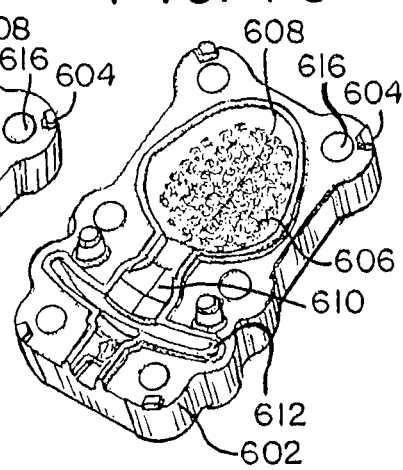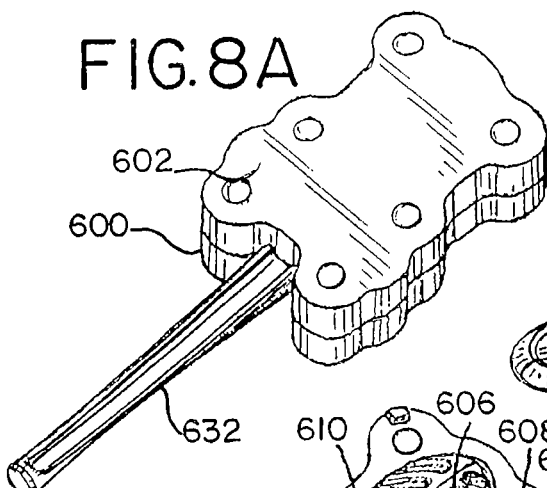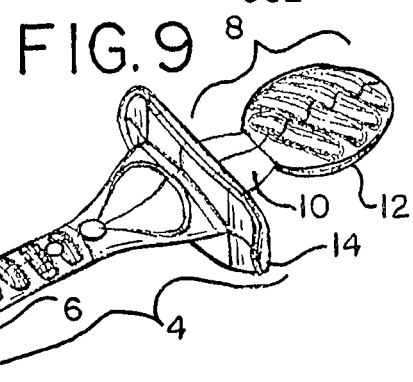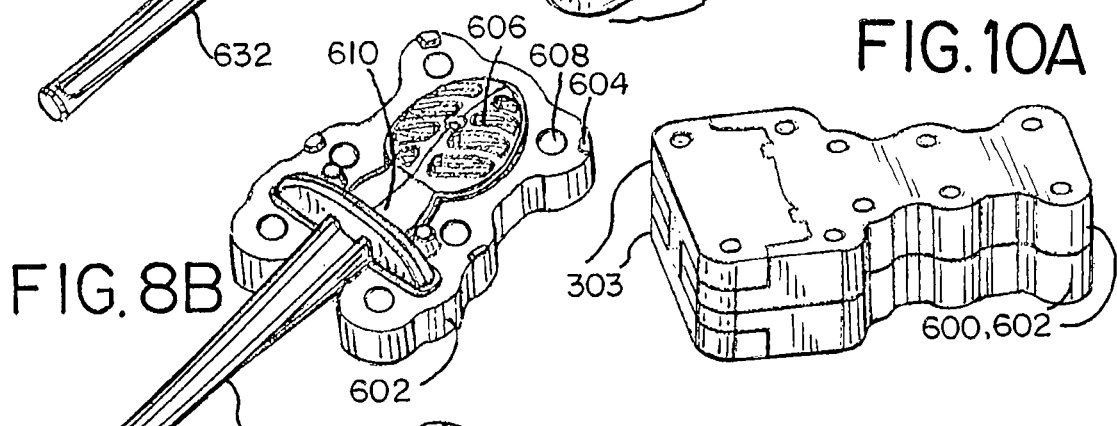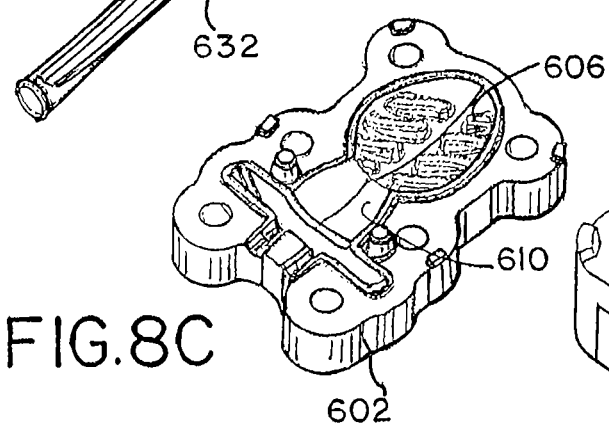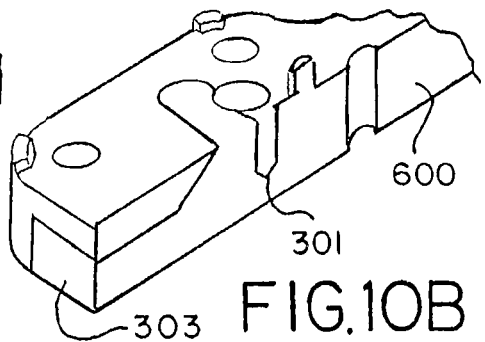

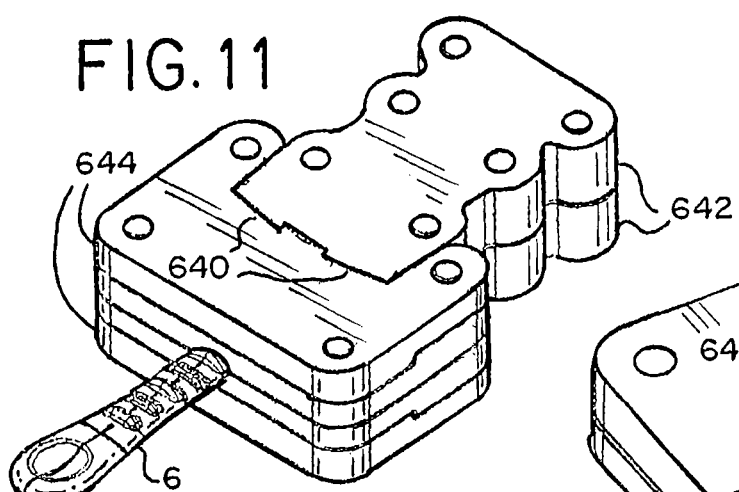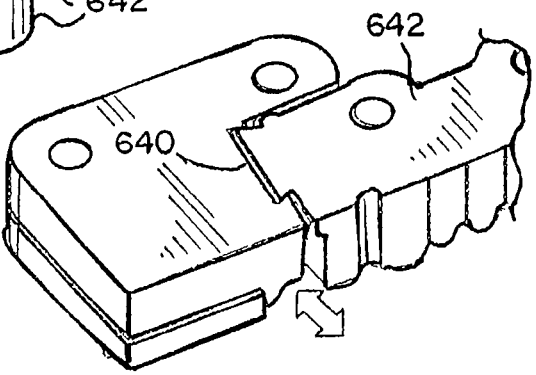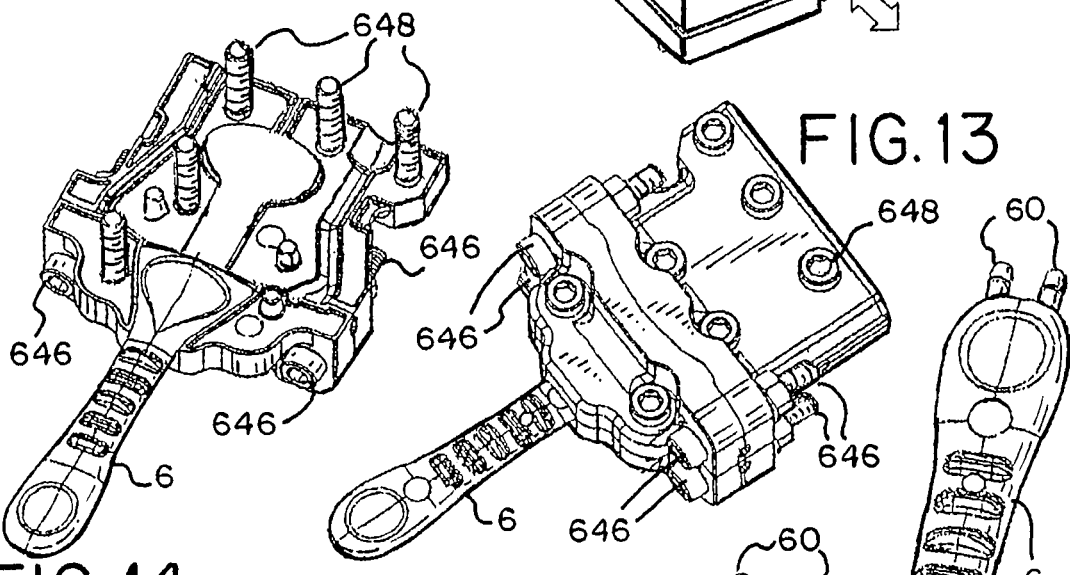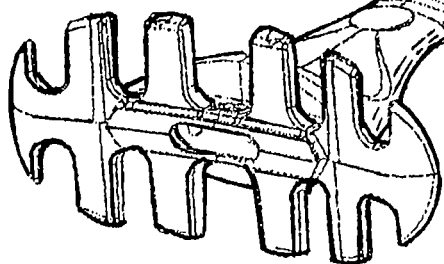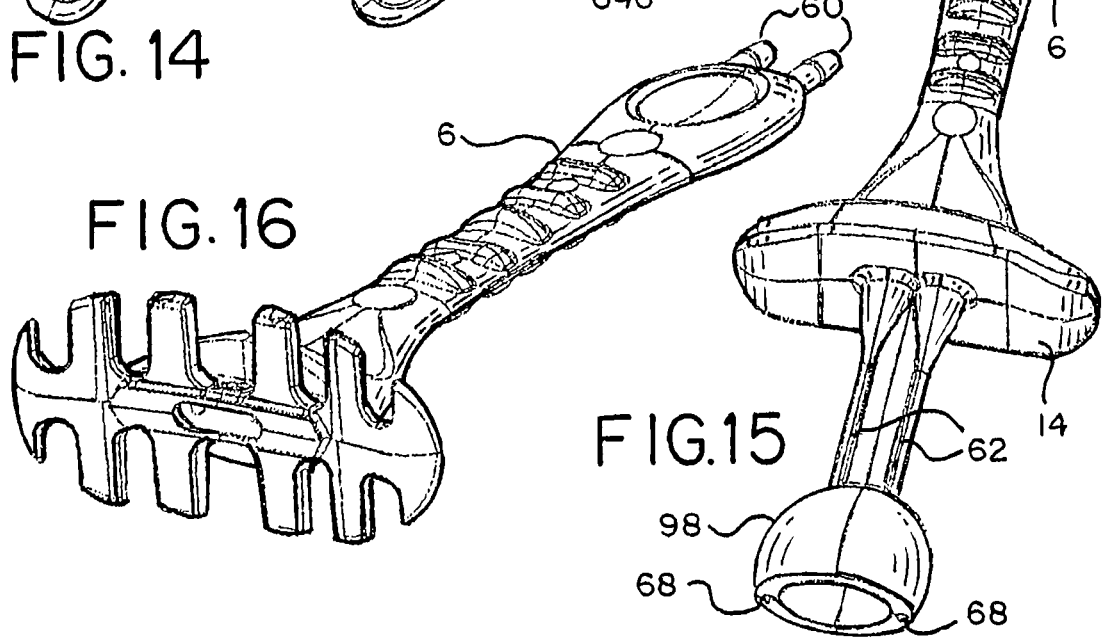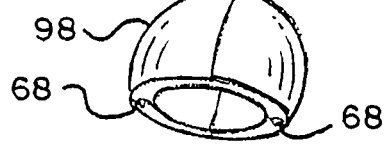

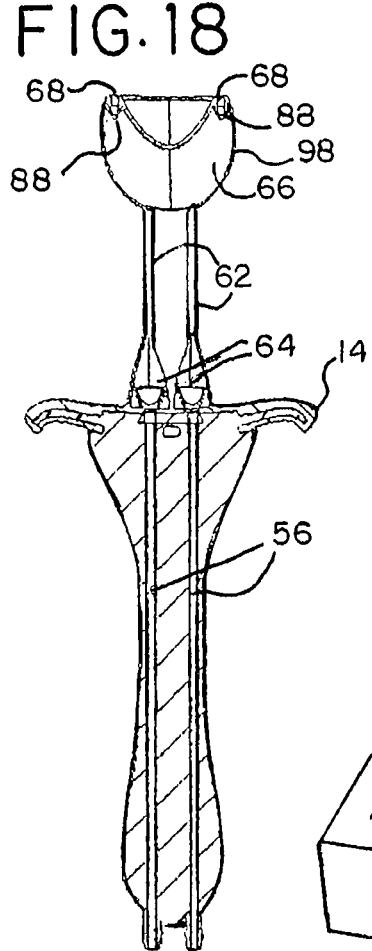
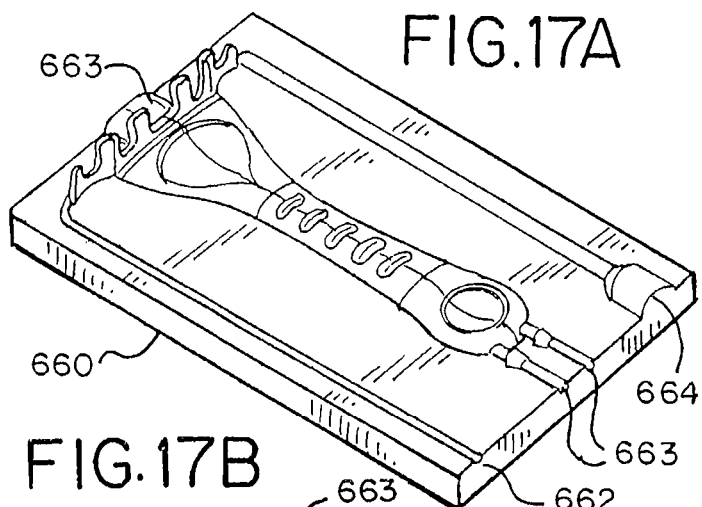
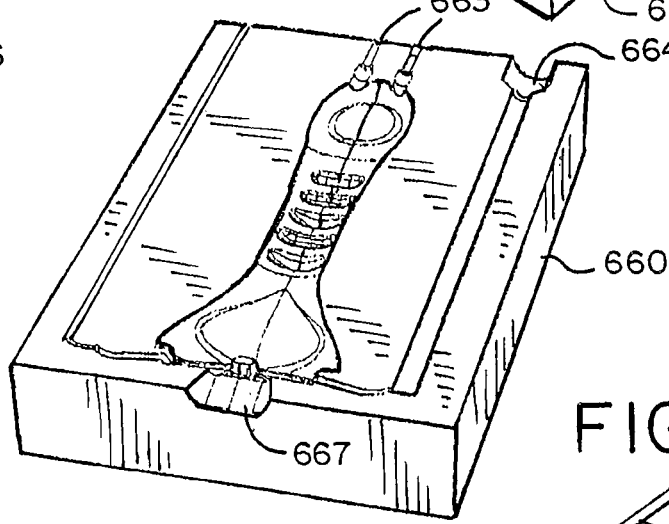
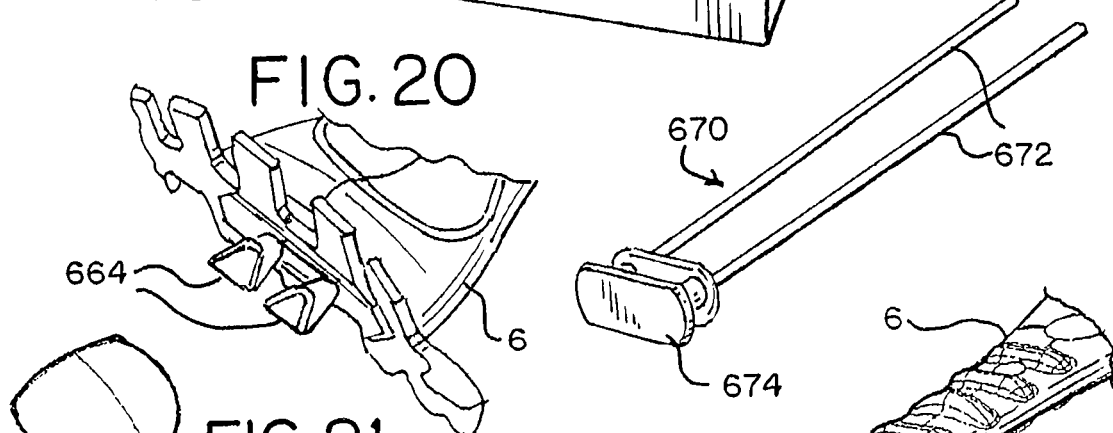
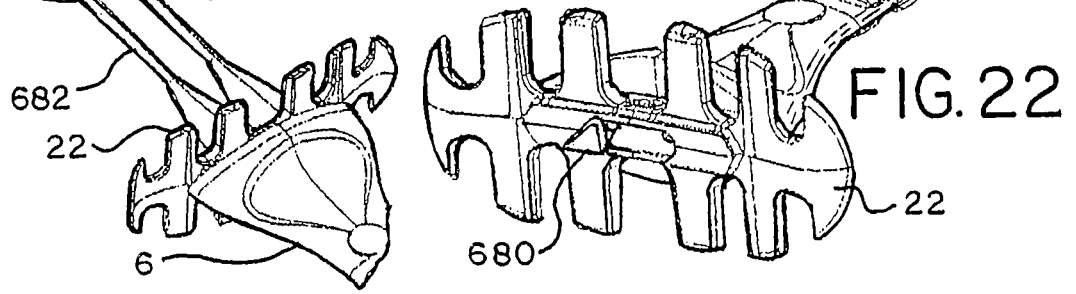

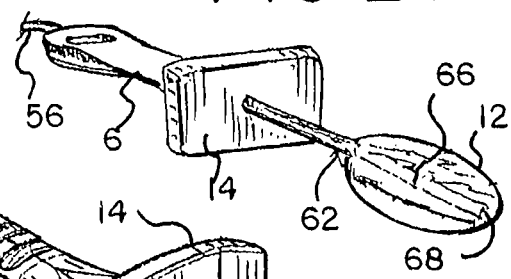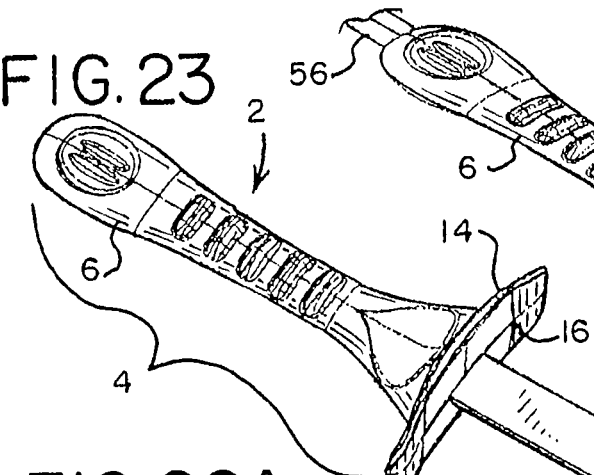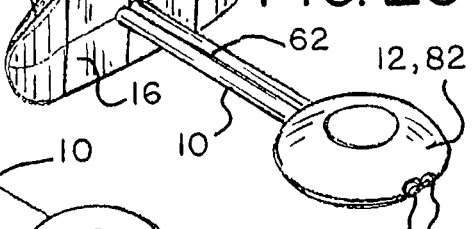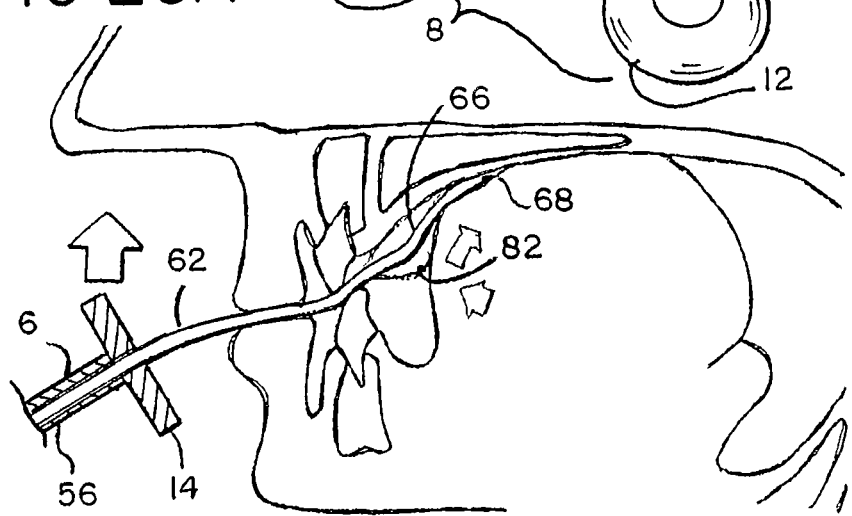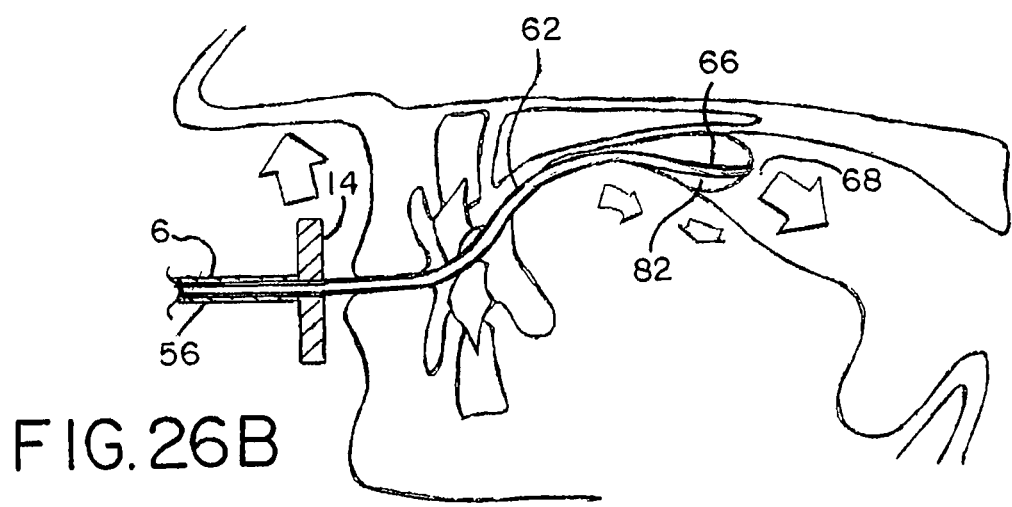

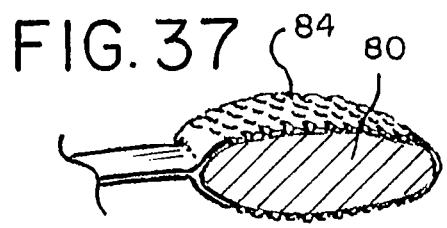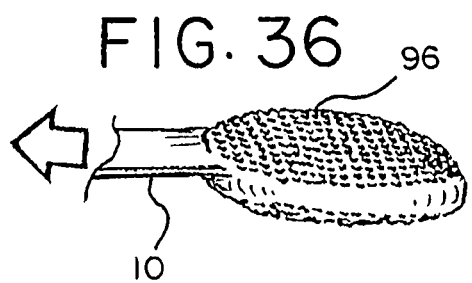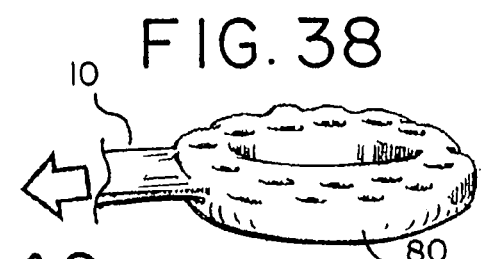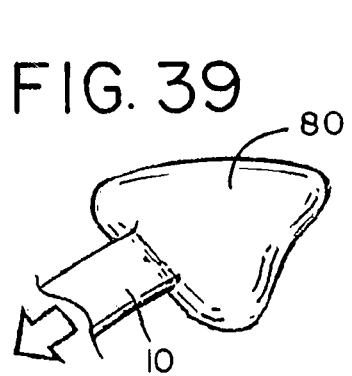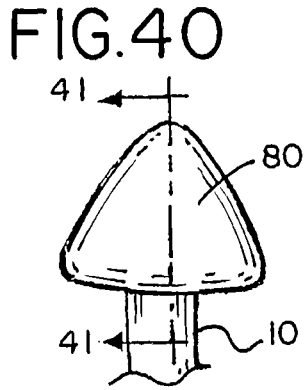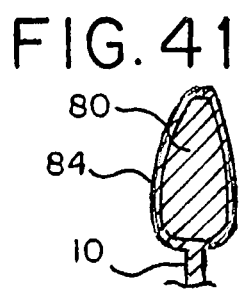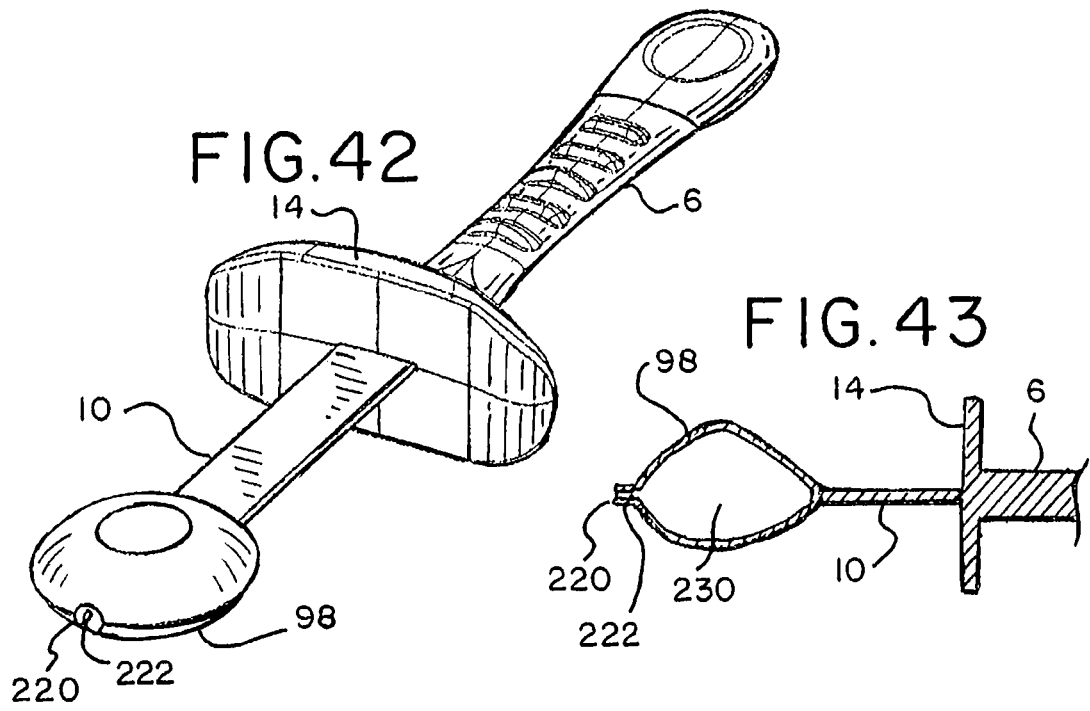

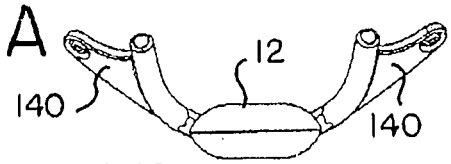
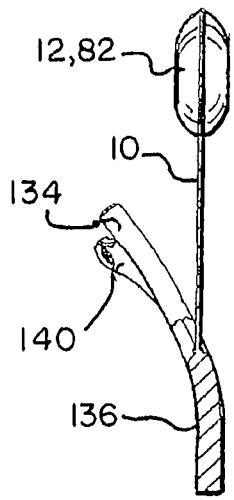
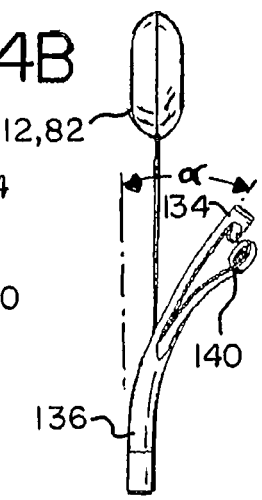
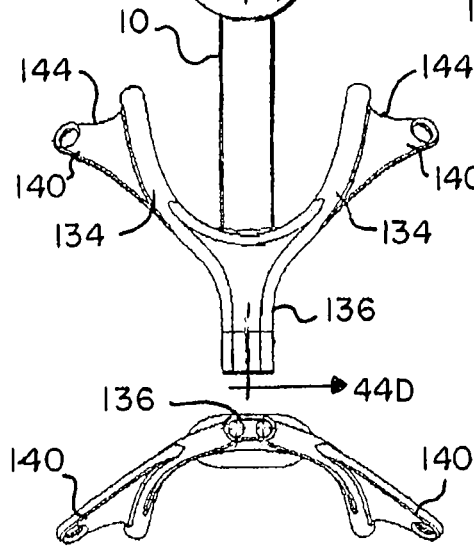
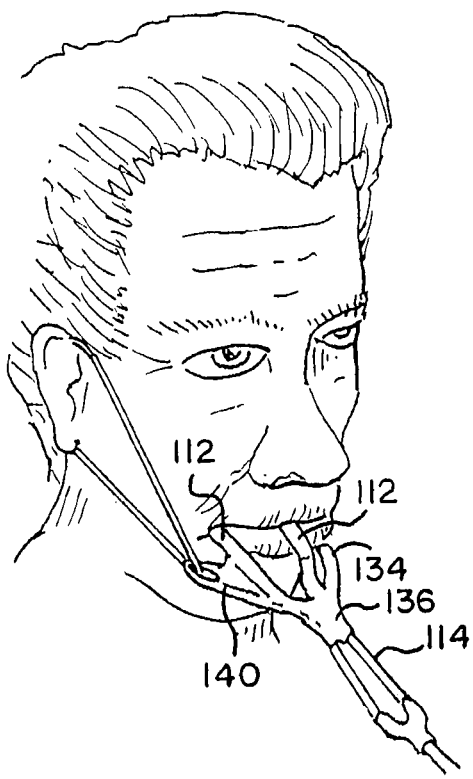
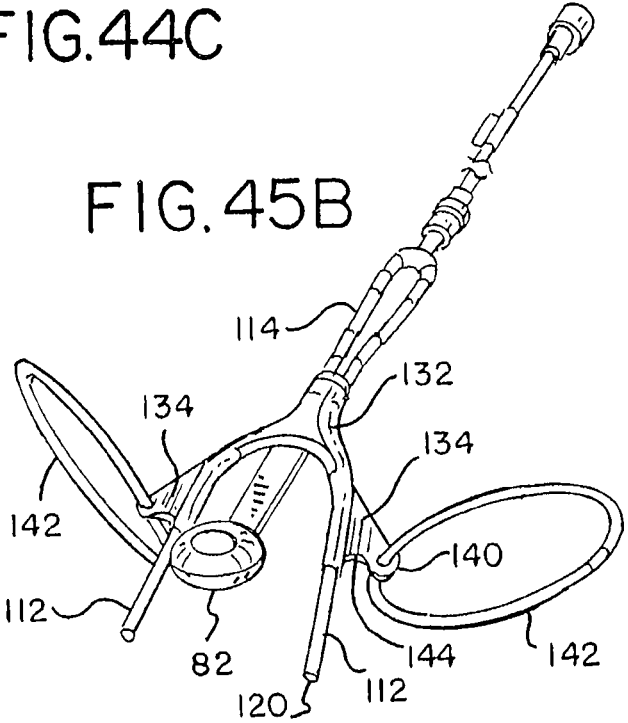
FIG.44A  FIG.44D  FIG.44E  FIG.44B  FIG.44C  FIG.45A  FIG.45B

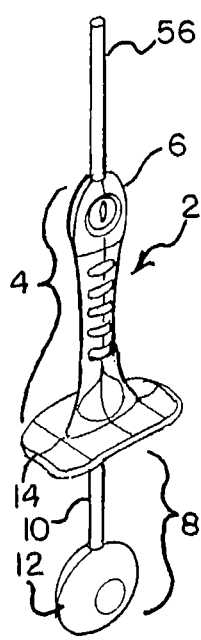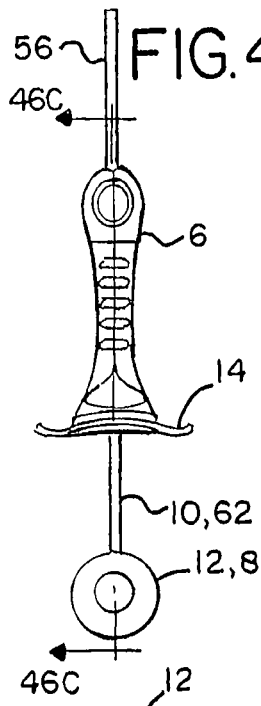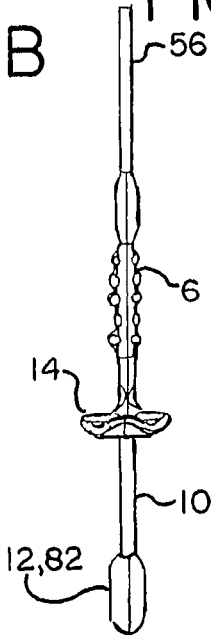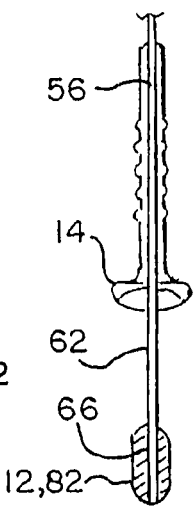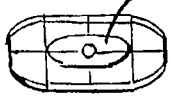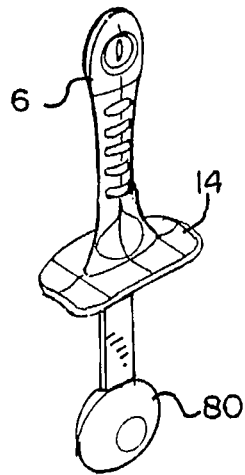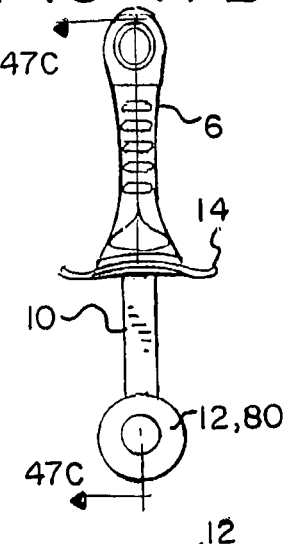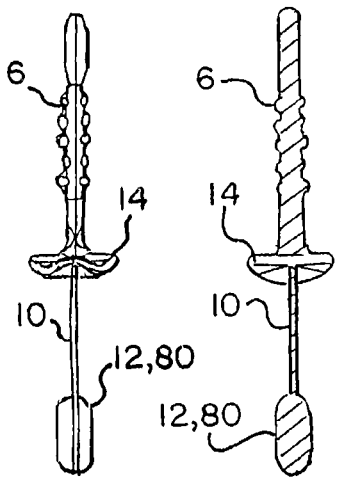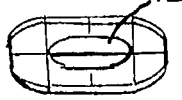

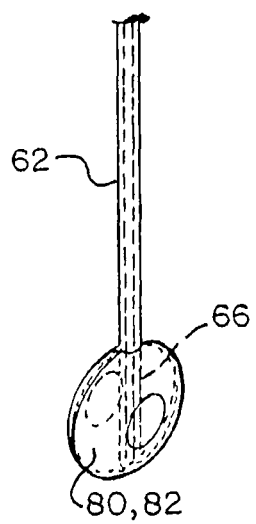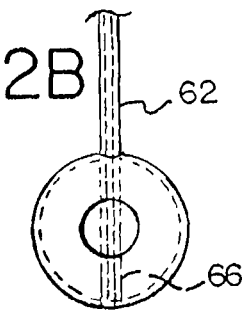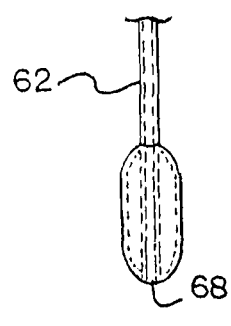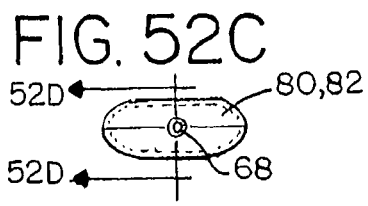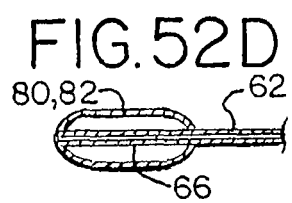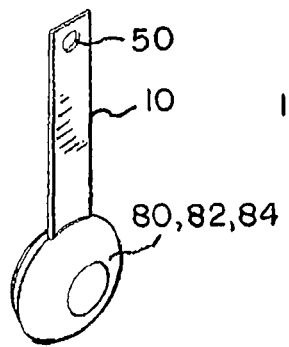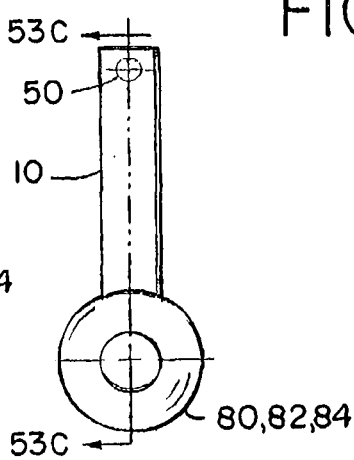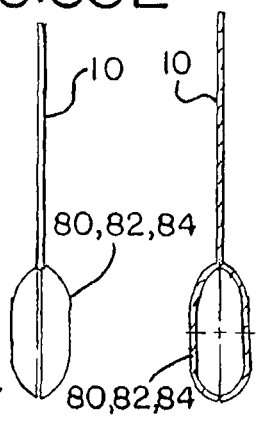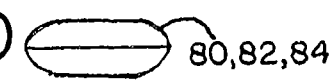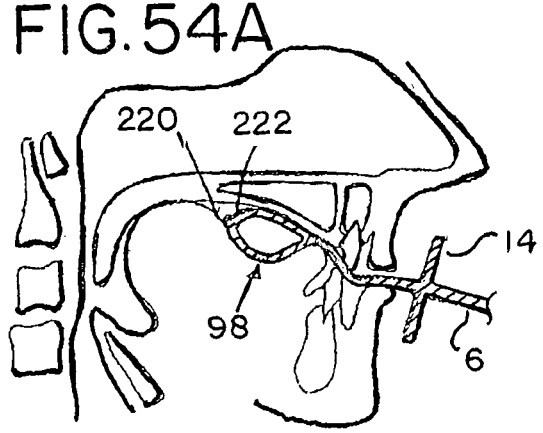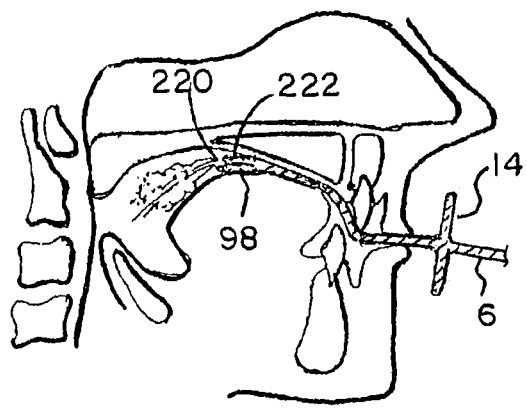

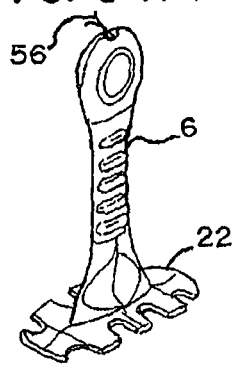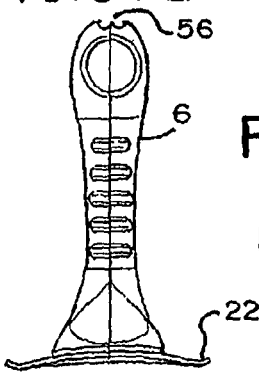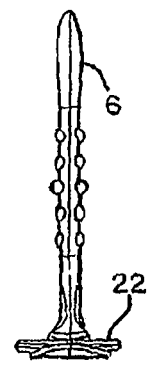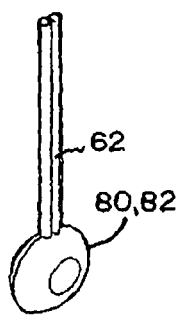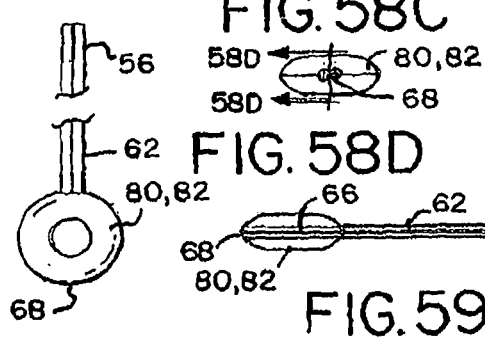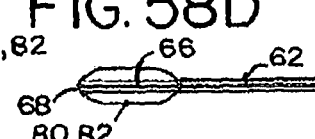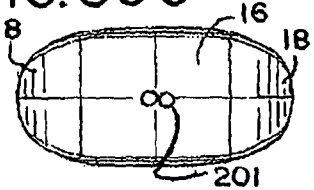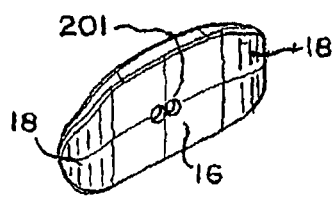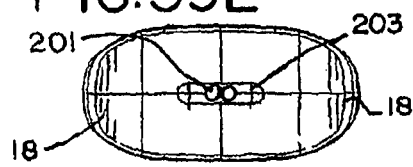

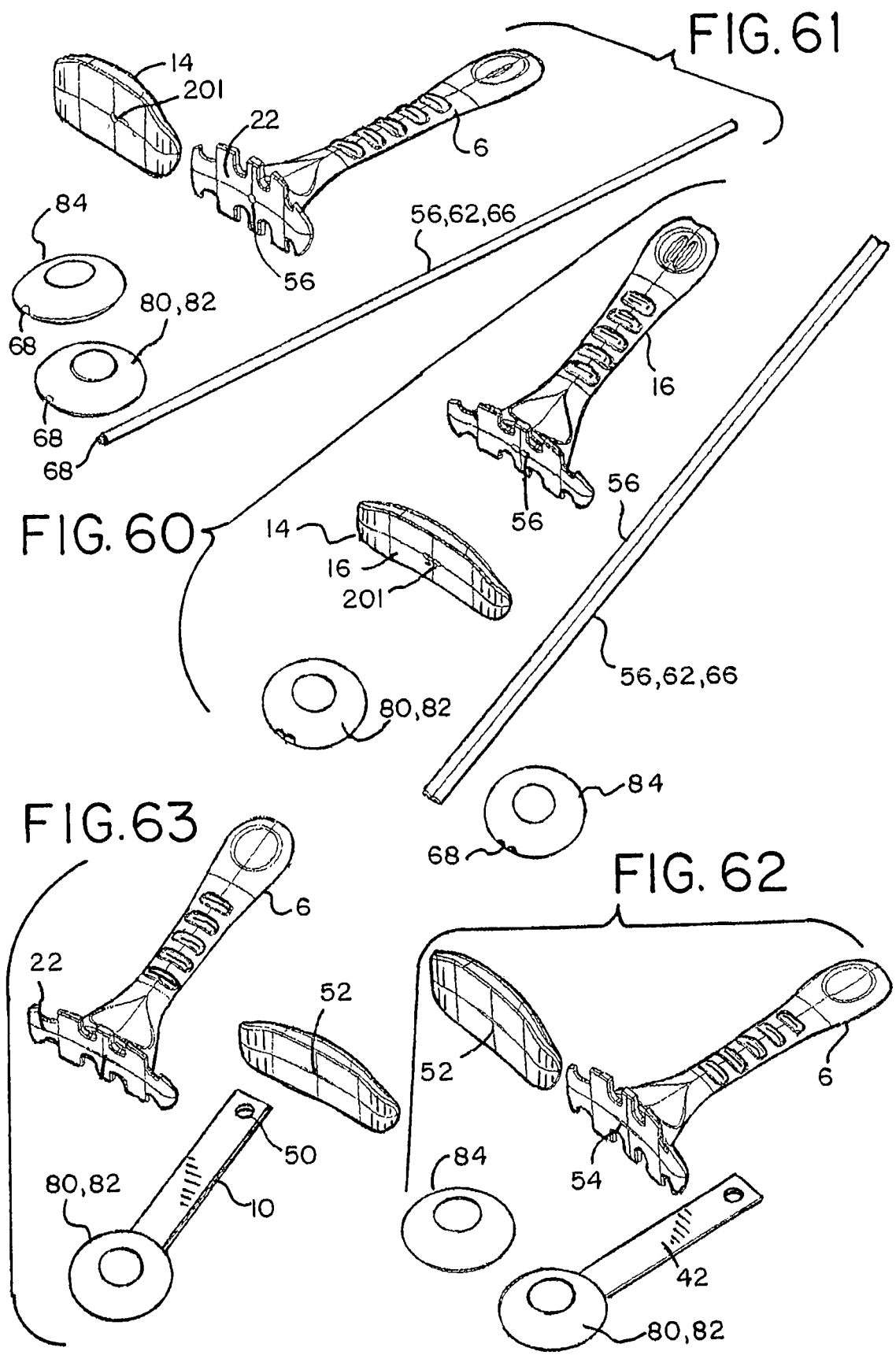

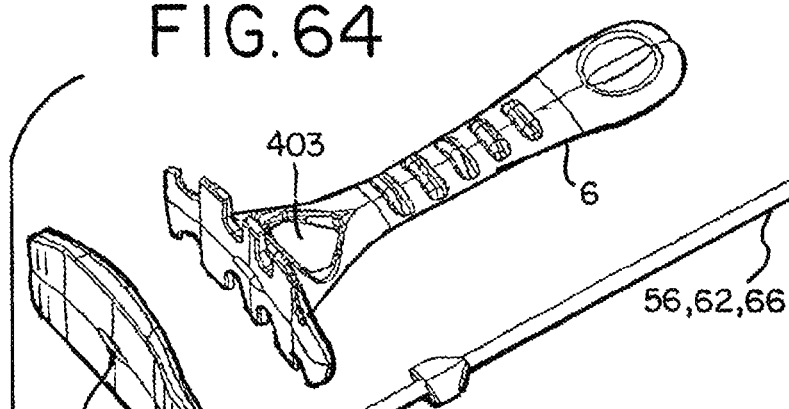
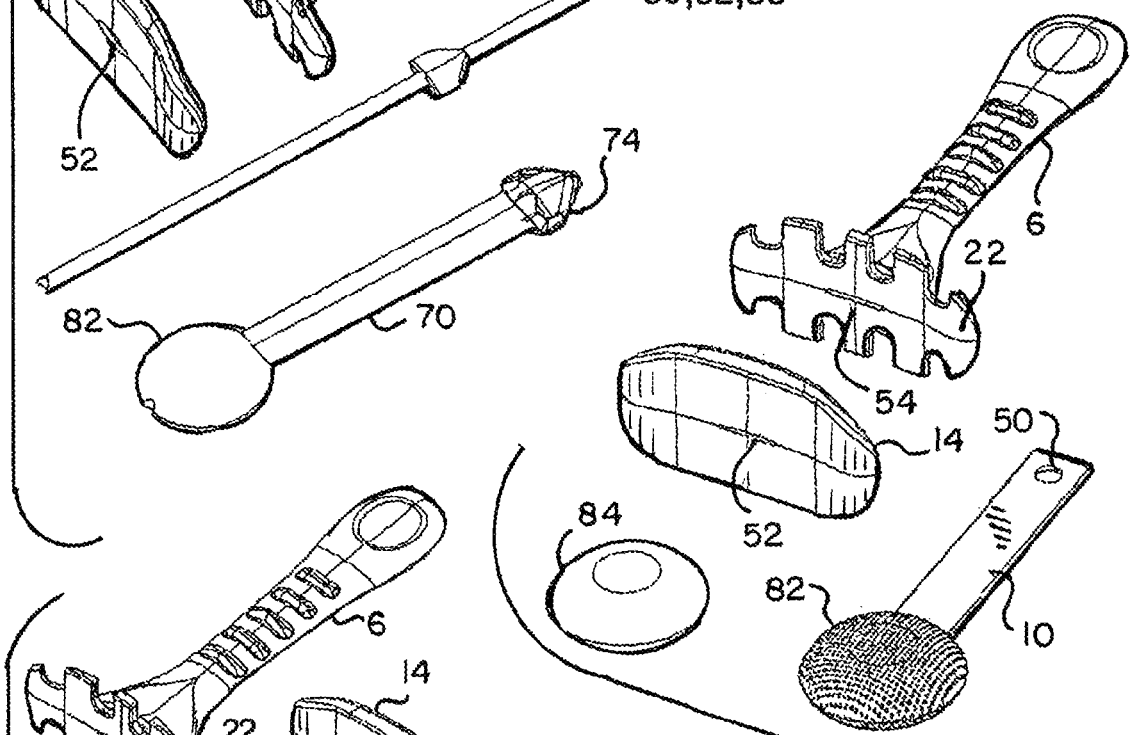
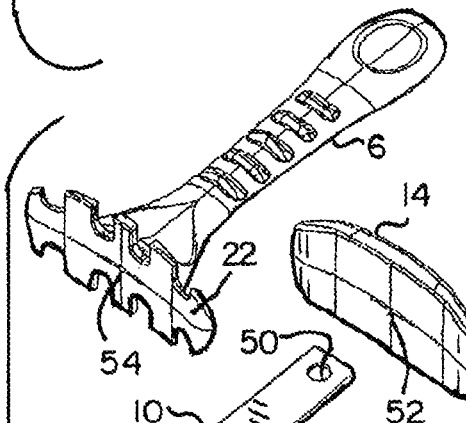
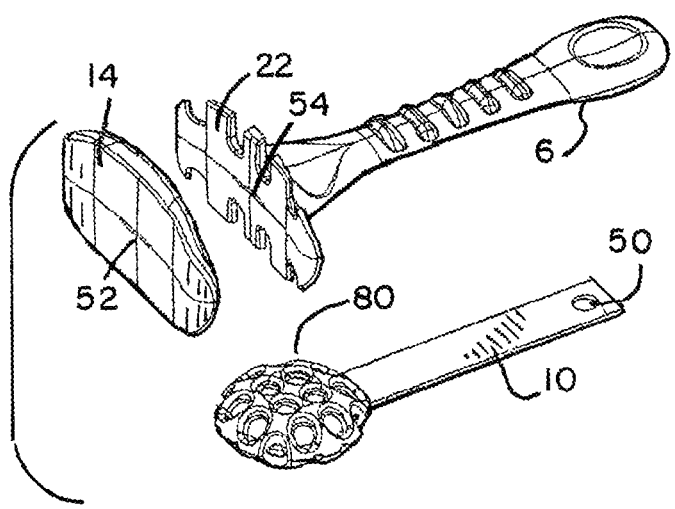

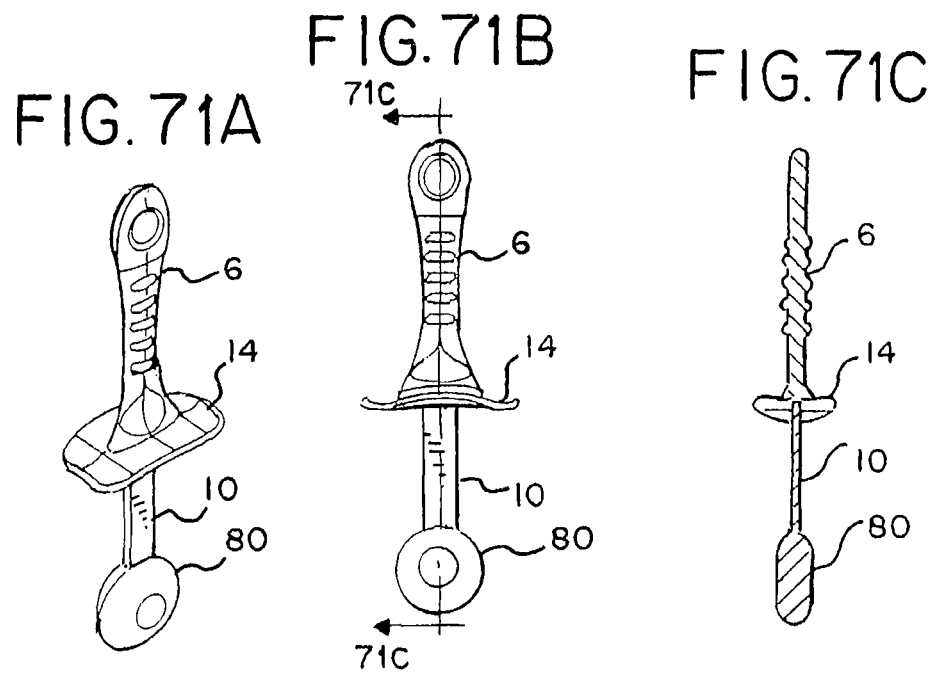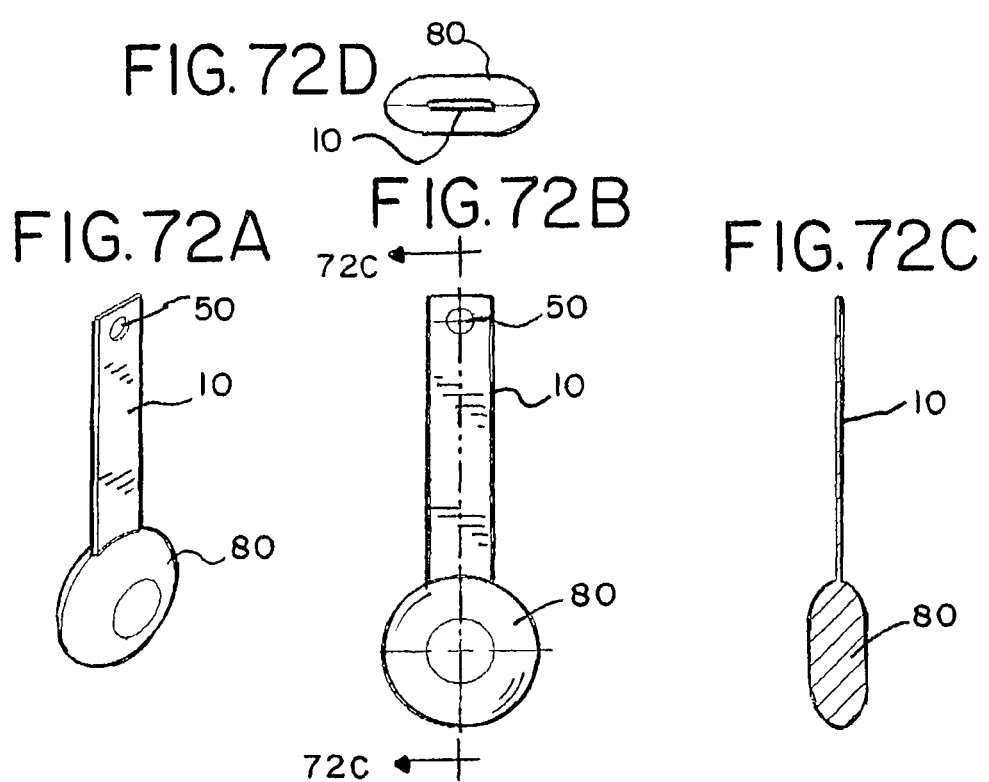

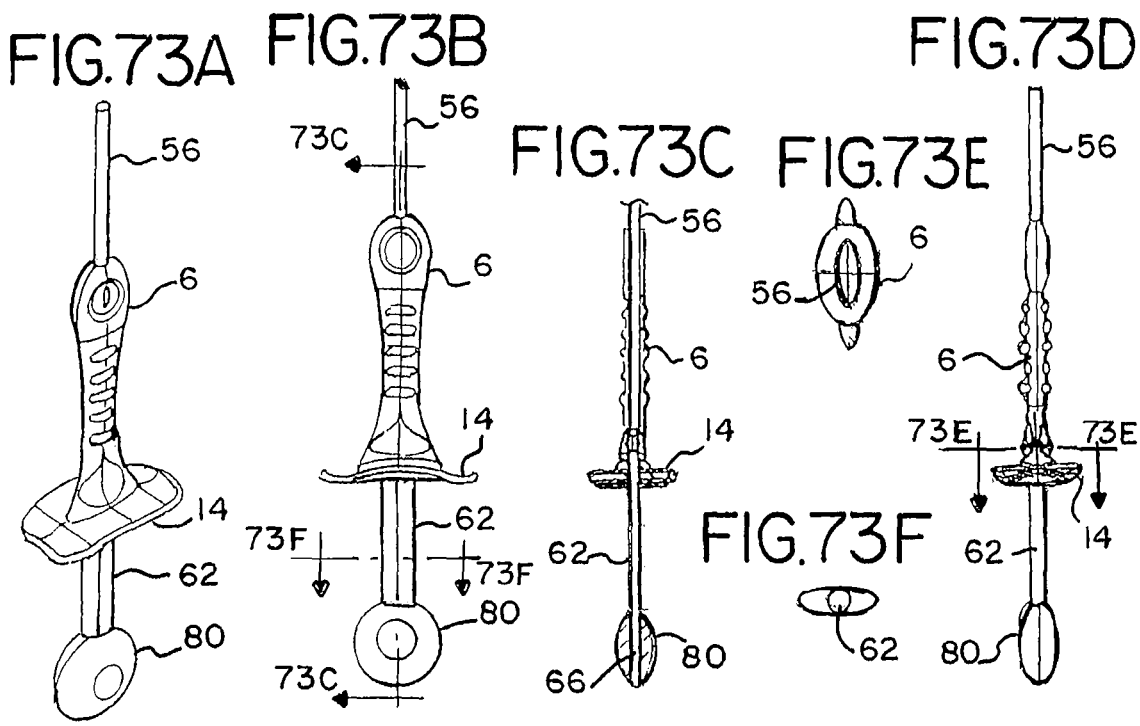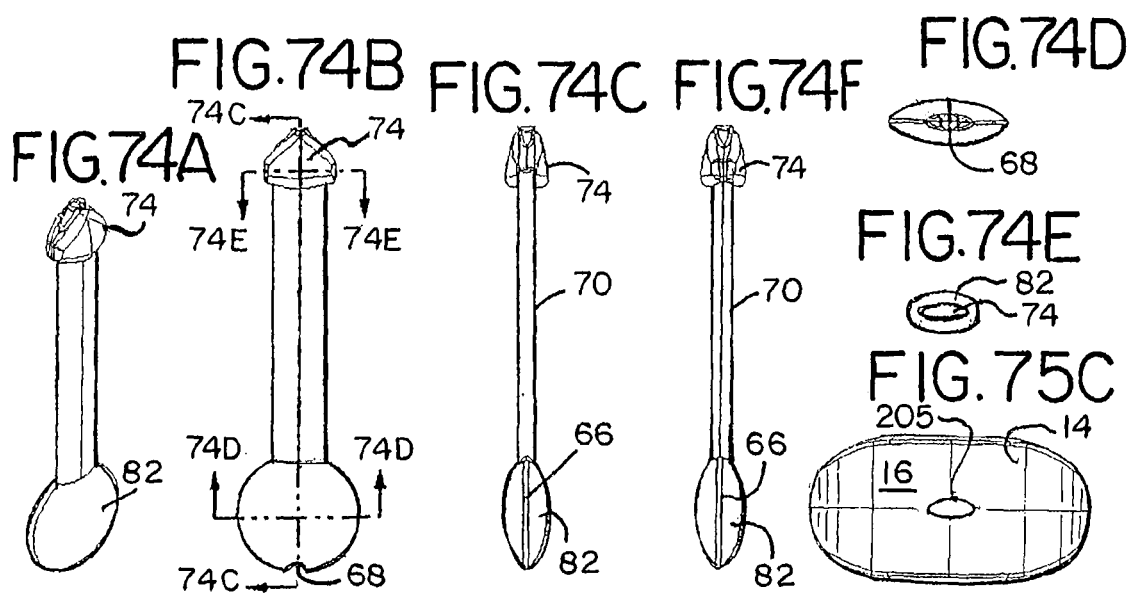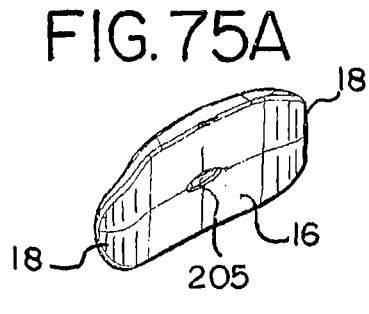

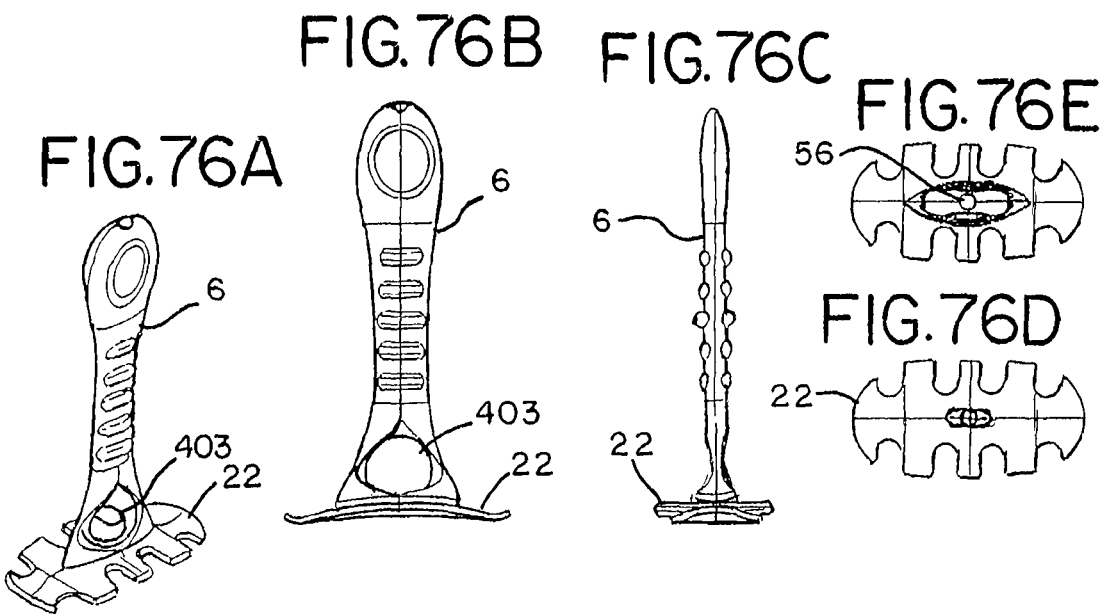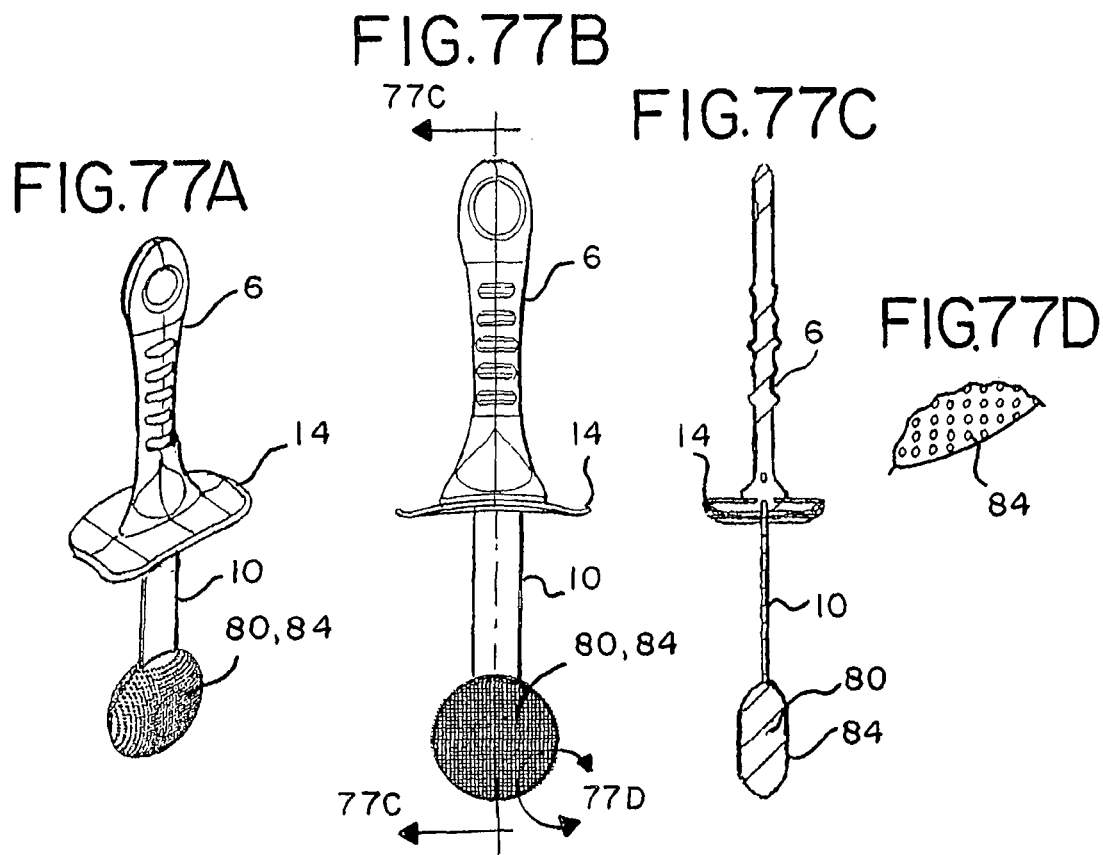

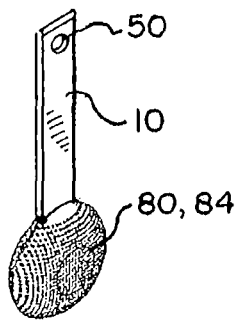
FIG. 78A
FIG. 78F
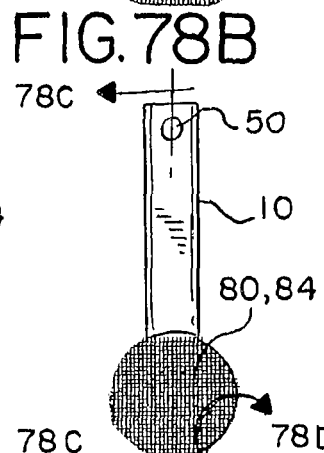
FIG. 78B
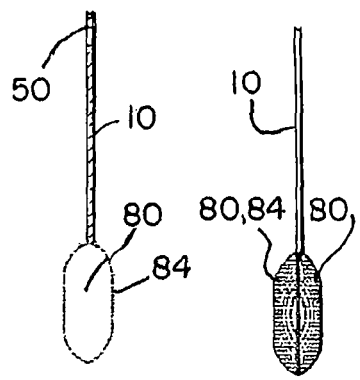
FIG. 78C
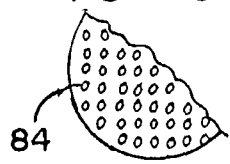
FIG. 78D
FIG. 78G
FIG. 78E
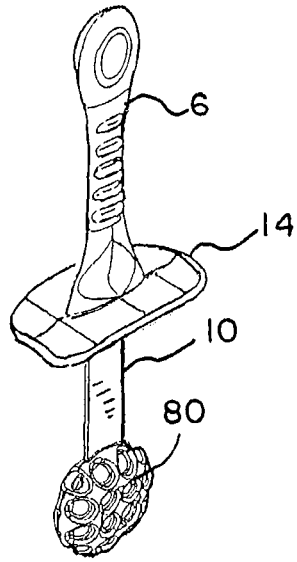
FIG. 79A
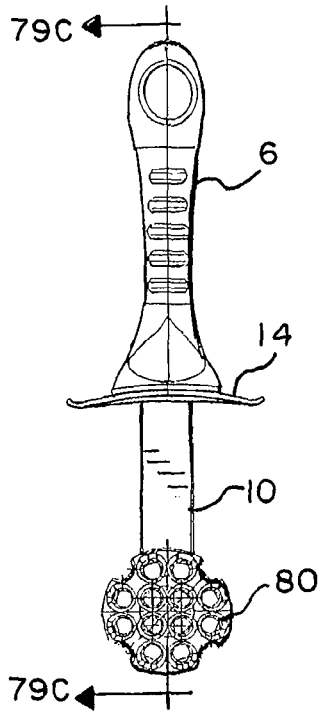
FIG. 79B
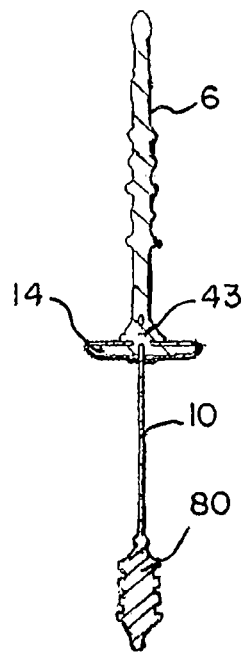
FIG. 79C

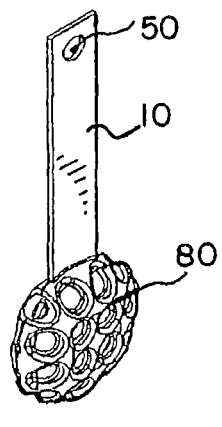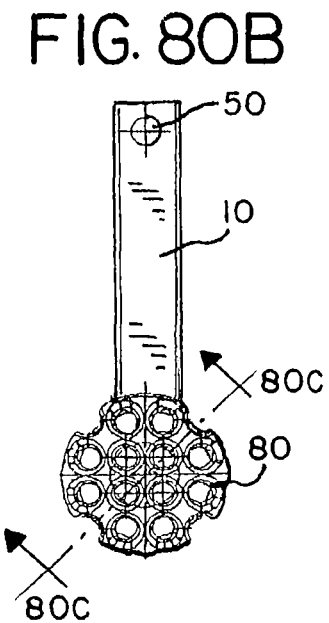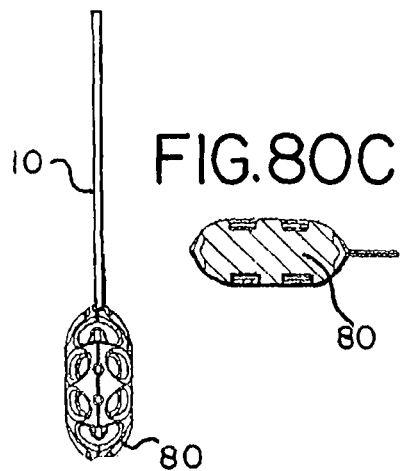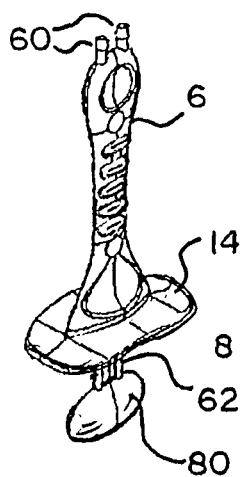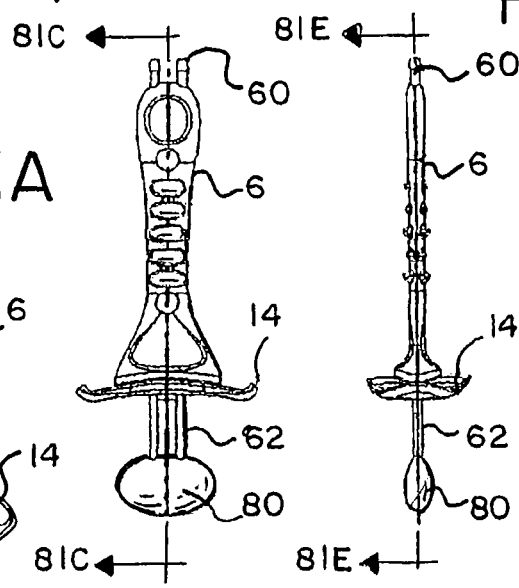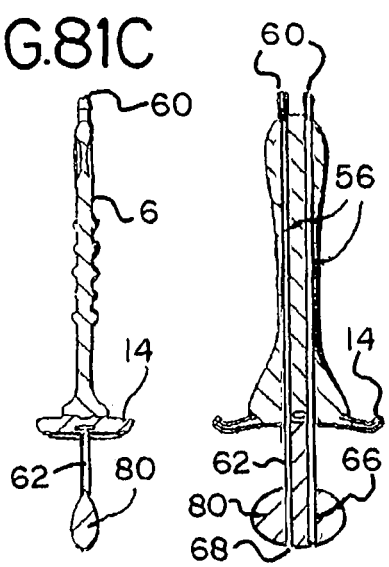

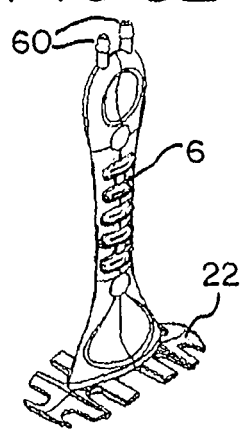
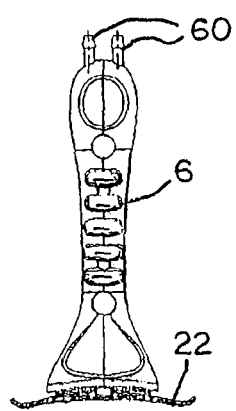
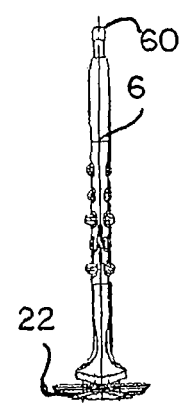
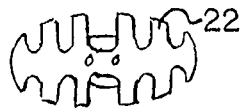
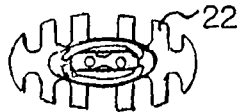
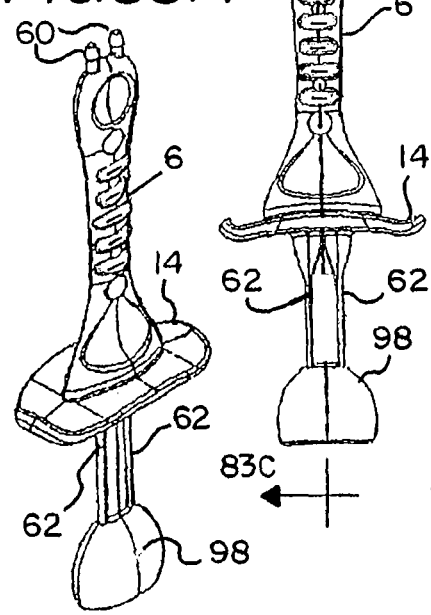
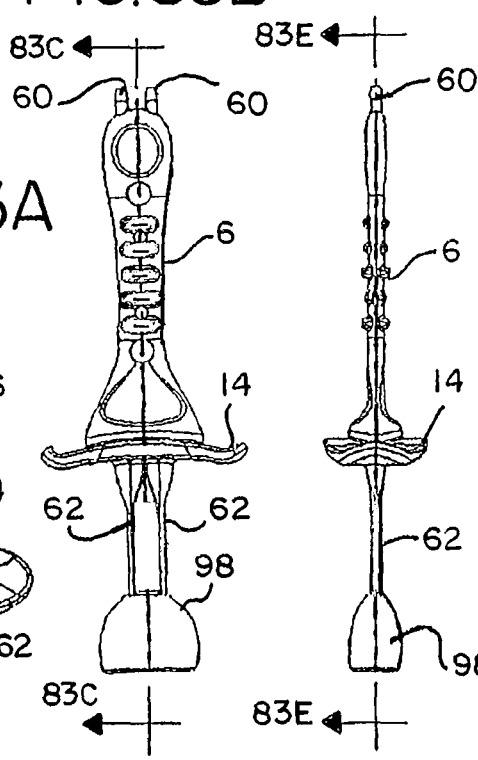
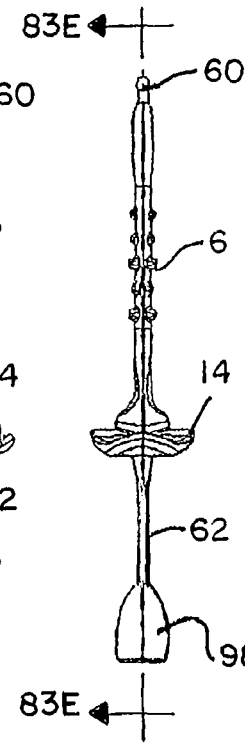
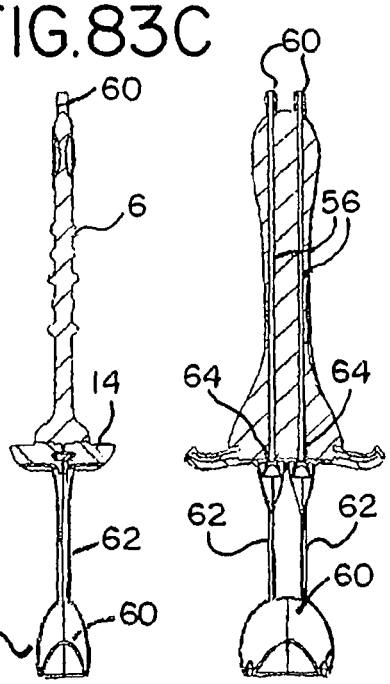

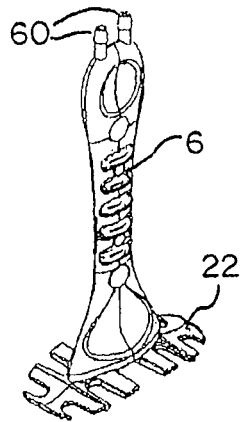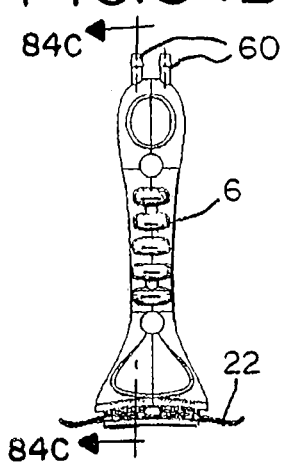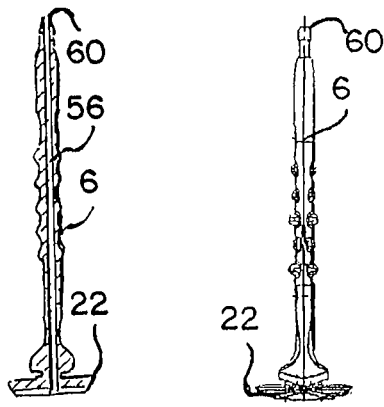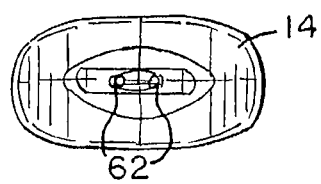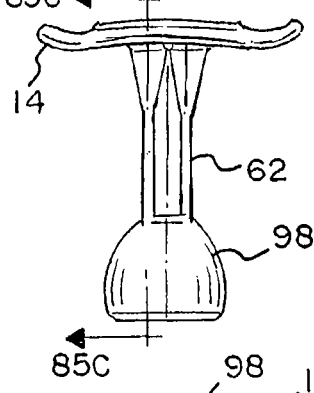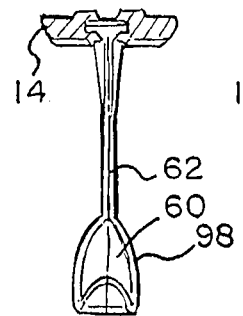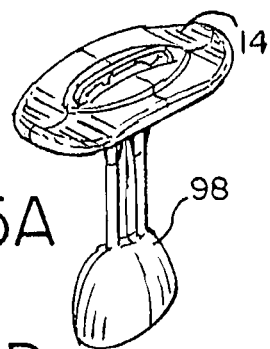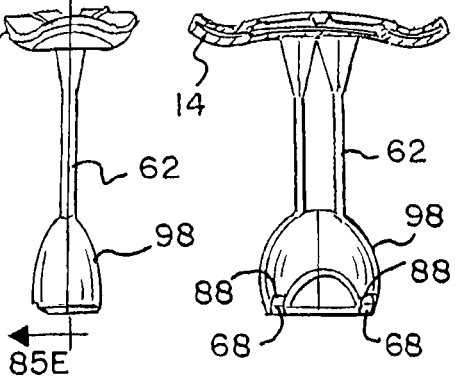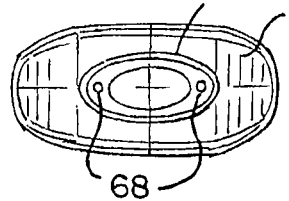

FIG. 86C
FIG. 86A
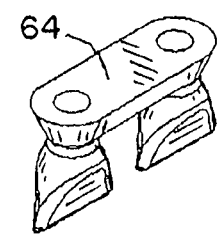
FIG. 86B
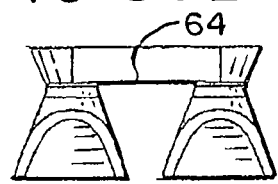
FIG. 86D
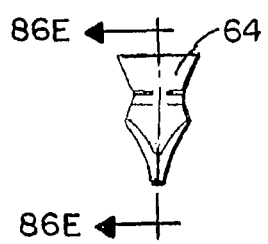
FIG. 86E
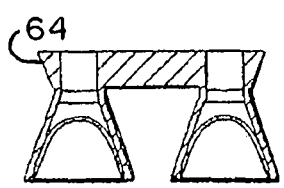
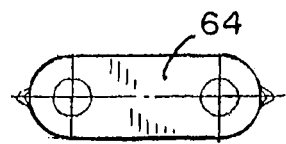
FIG. 86F
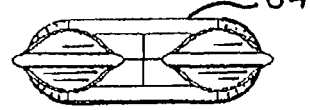
FIG. 87A
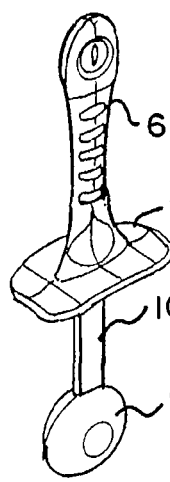
FIG. 87B
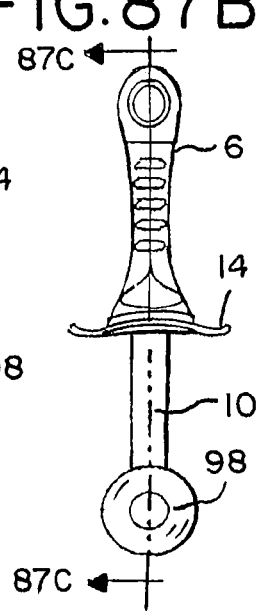
FIG. 87C
FIG. 87D
FIG. 87E
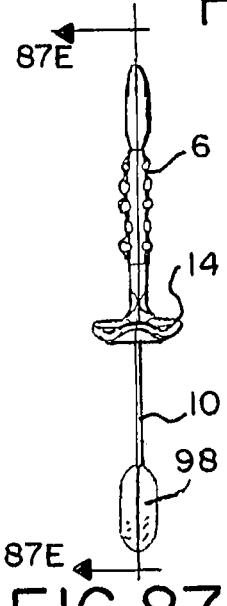
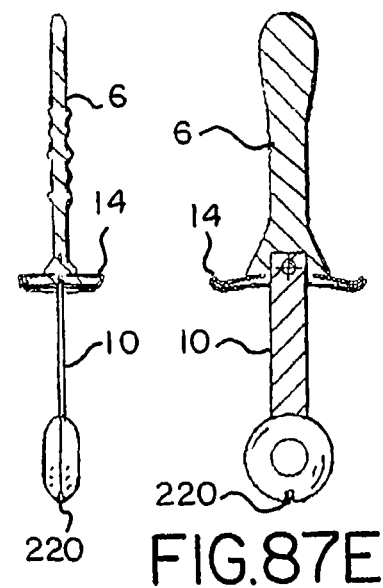

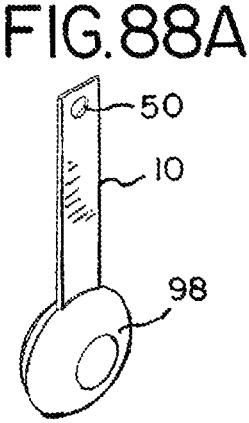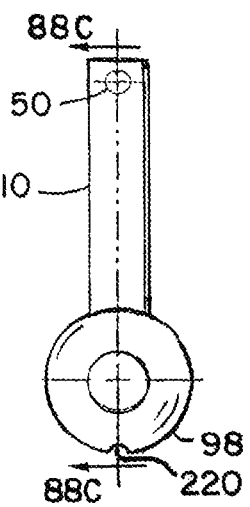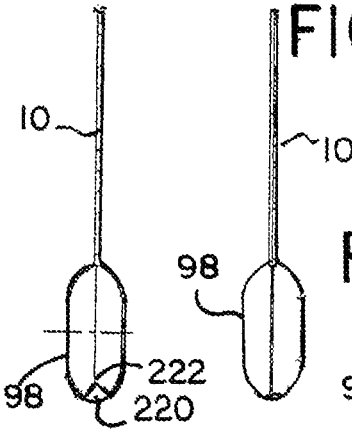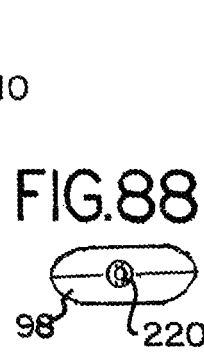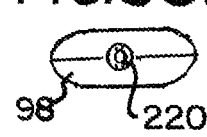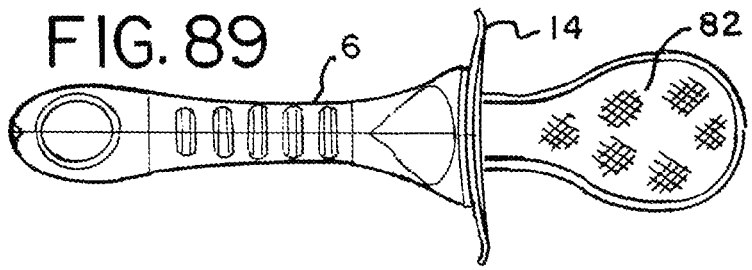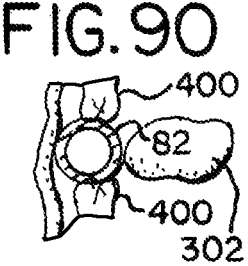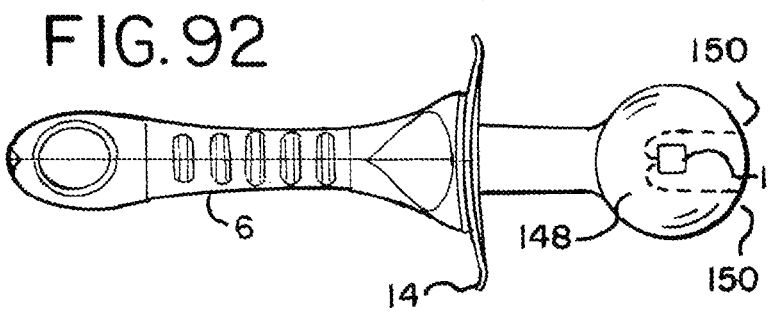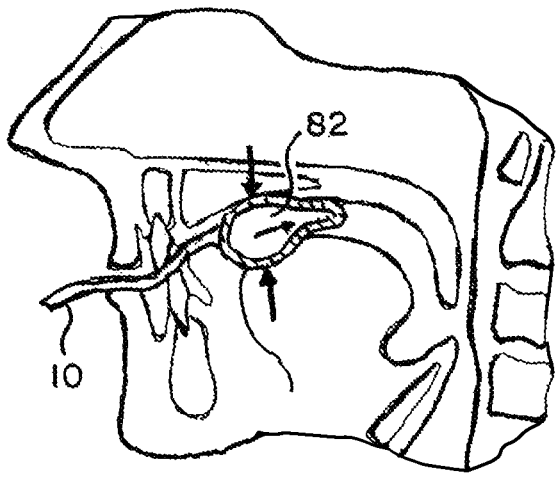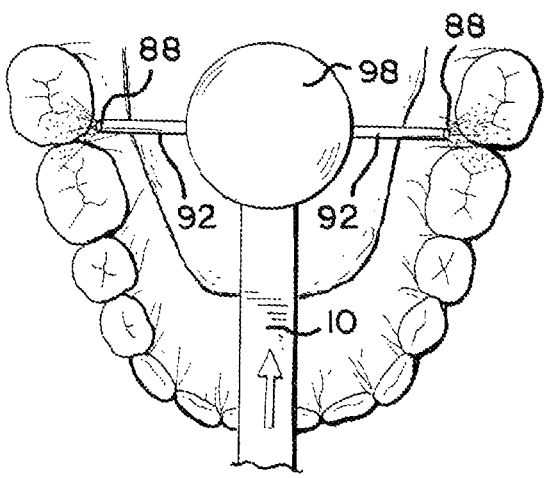

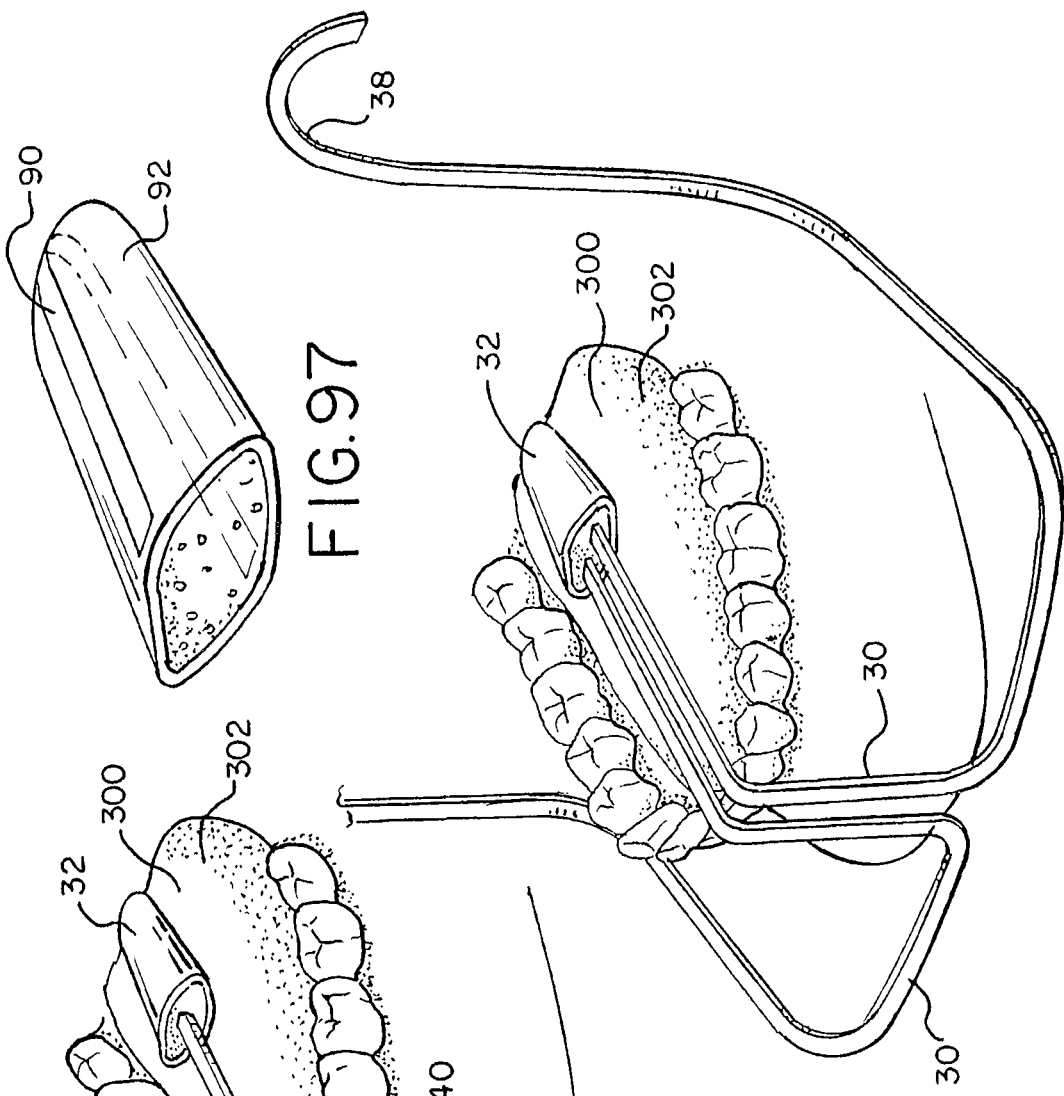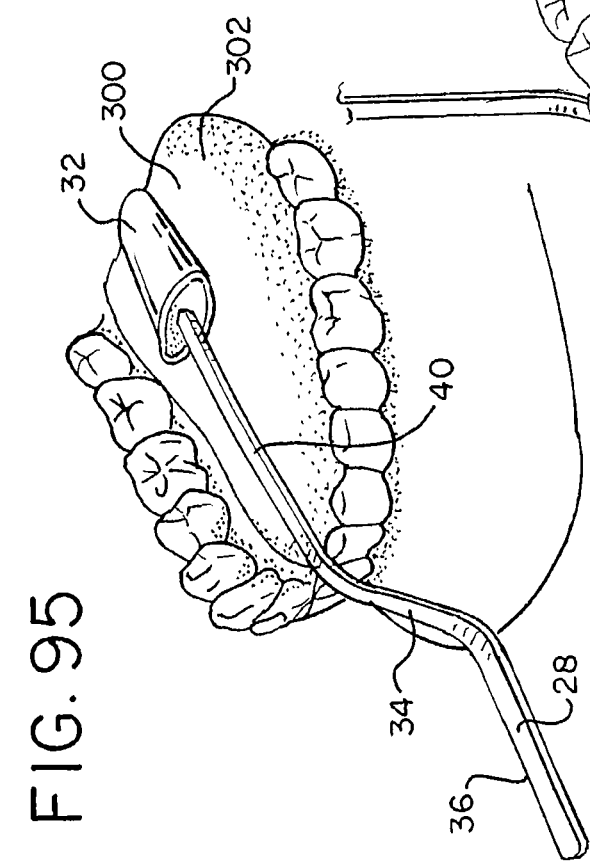

FIG. 100A
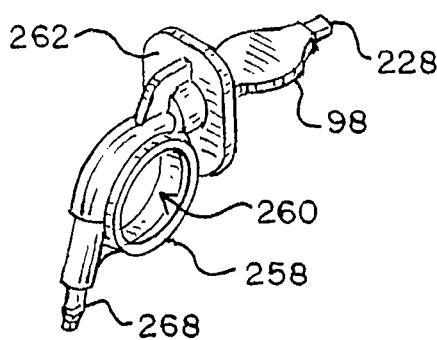
FIG. 100B
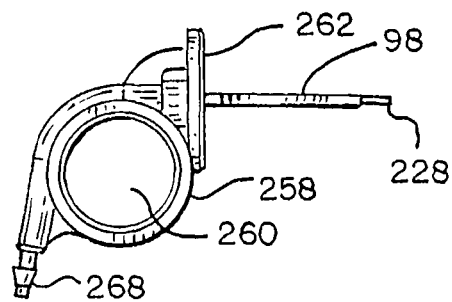
FIG. 100C
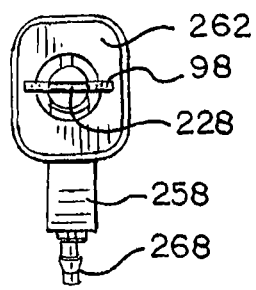
FIG. 100D
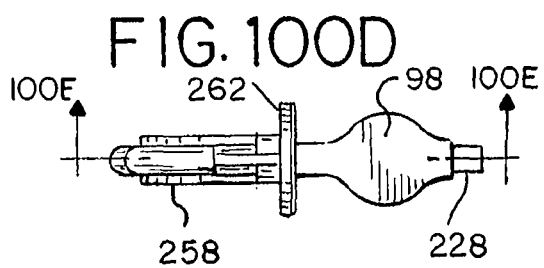
FIG. 100F
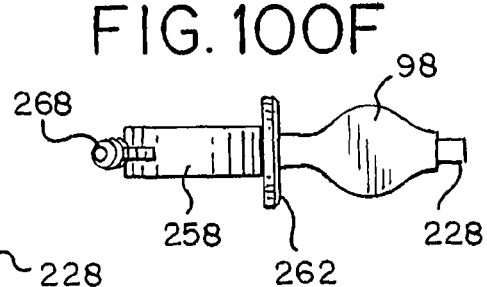
FIG. 100E
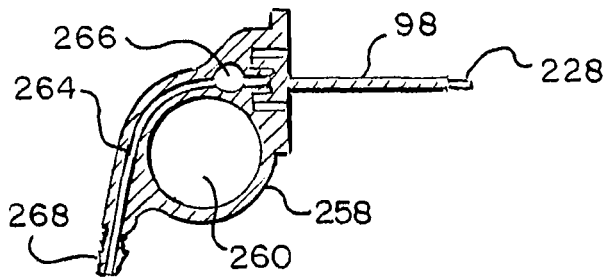
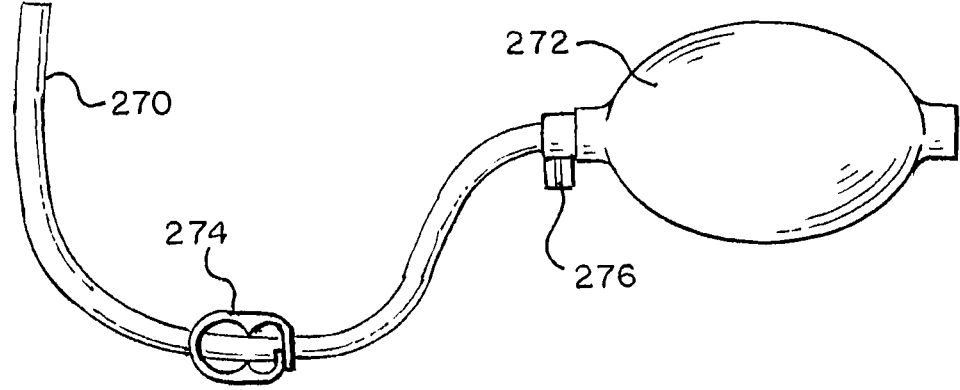

FIG. 103
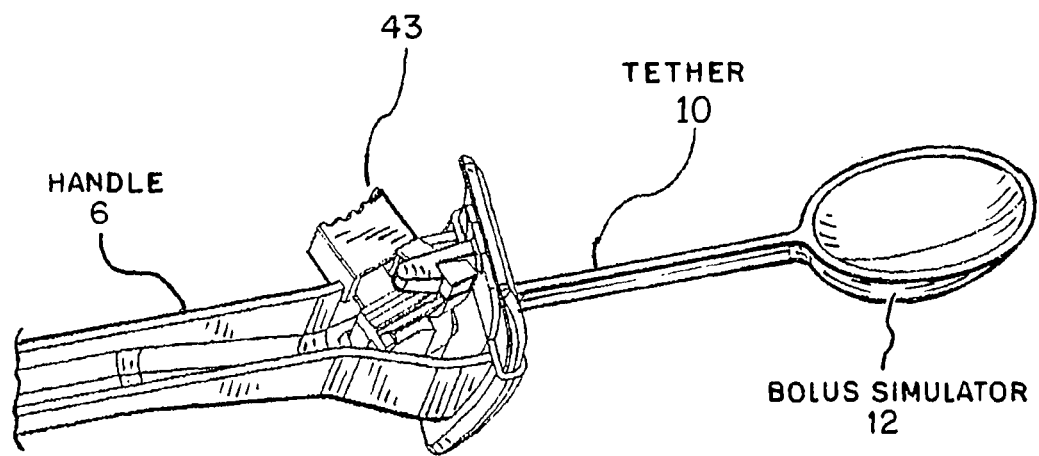
FIG. 104
FIG. 105
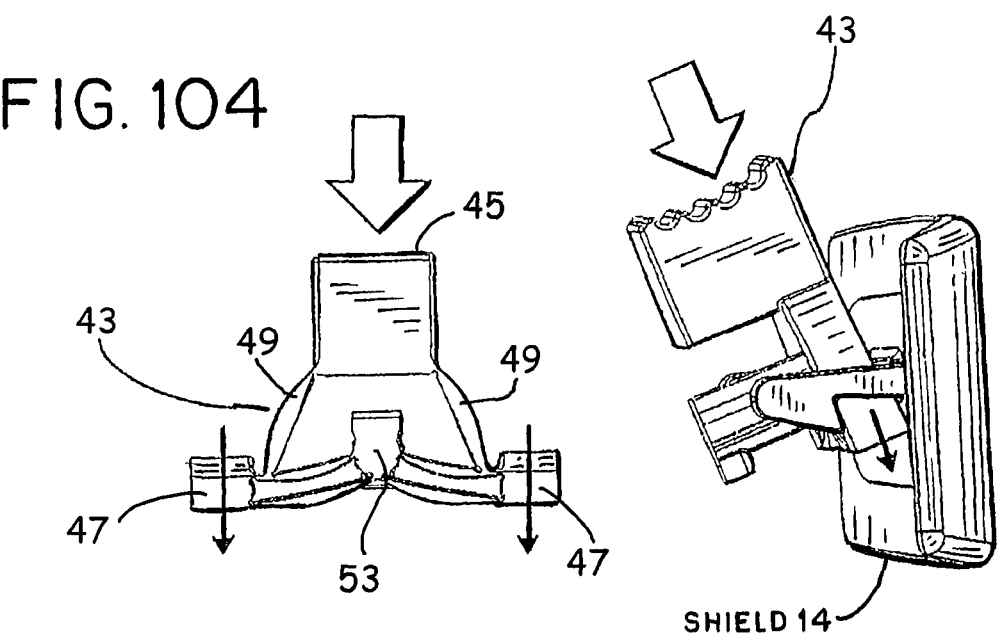

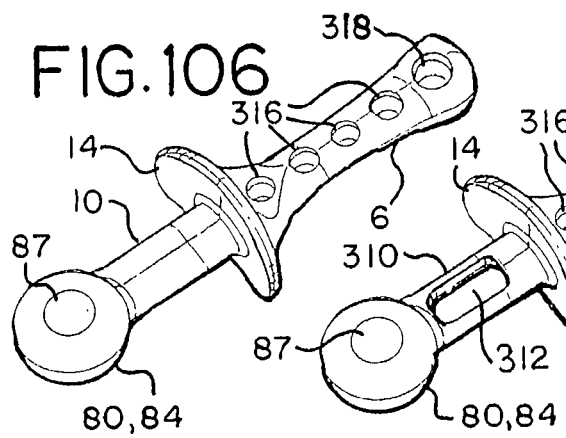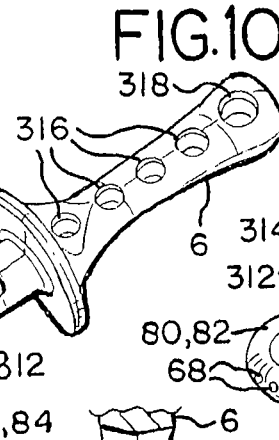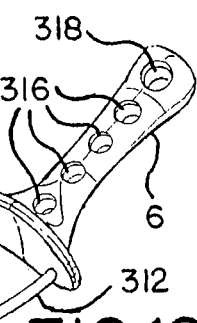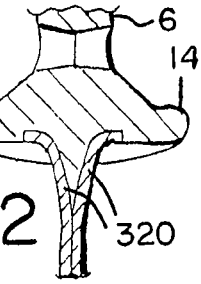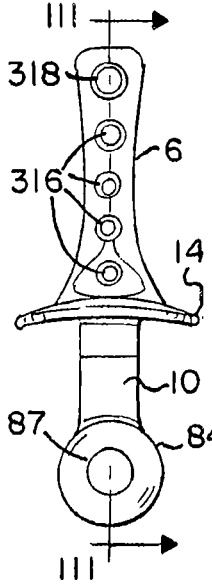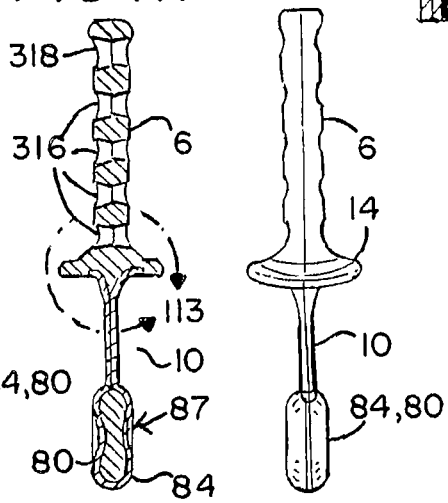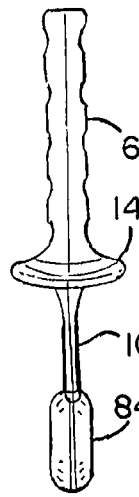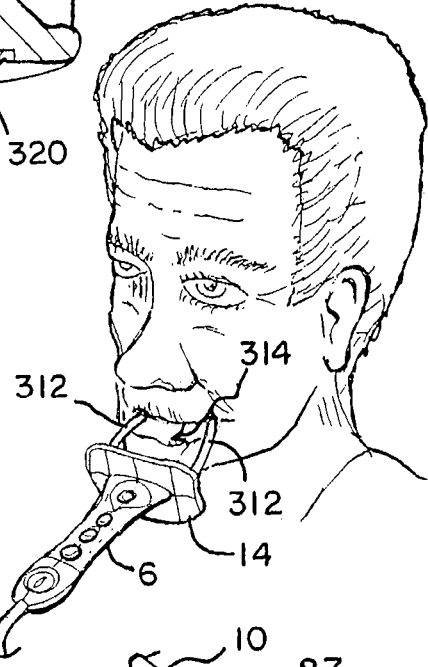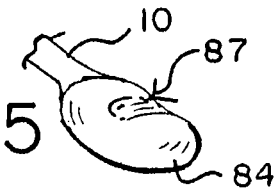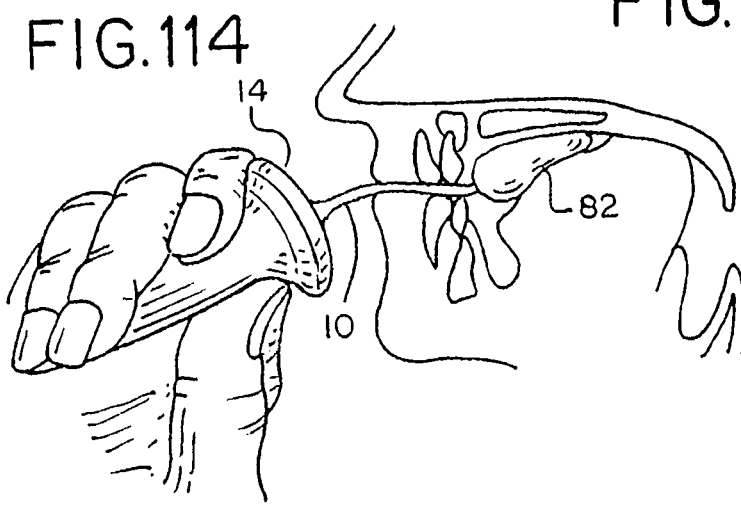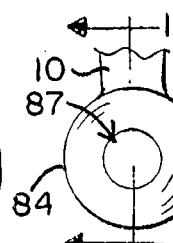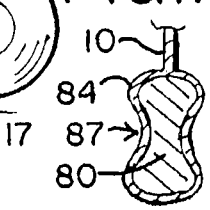

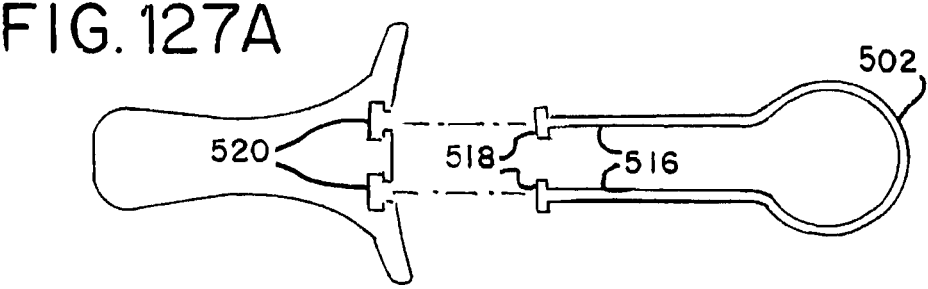
FIG. 127A
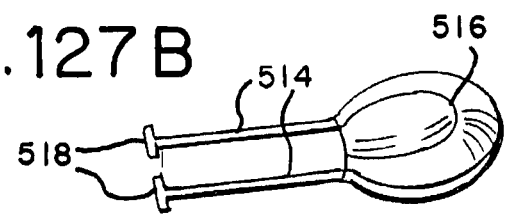
FIG. 127B
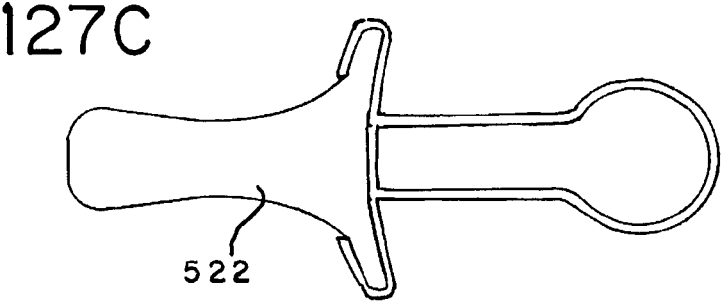
FIG. 127C
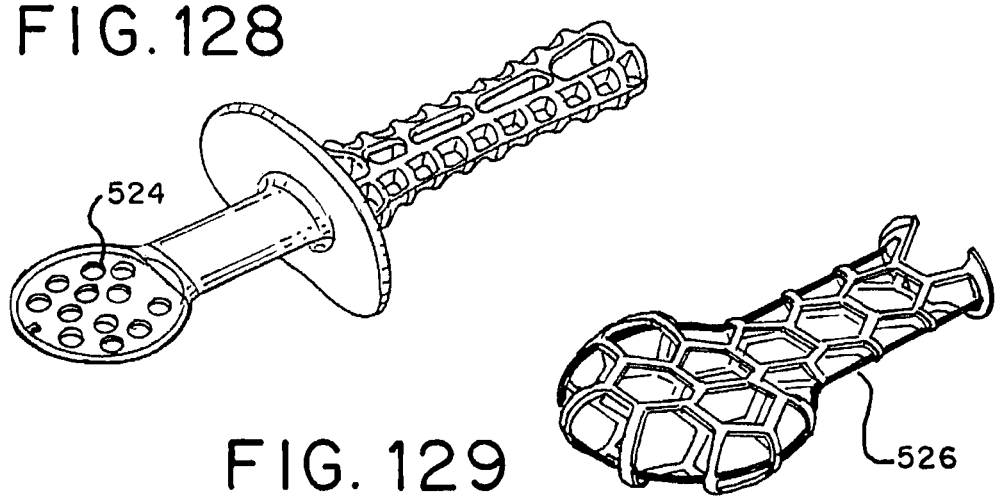
FIG. 128
FIG. 129

FIG. 144
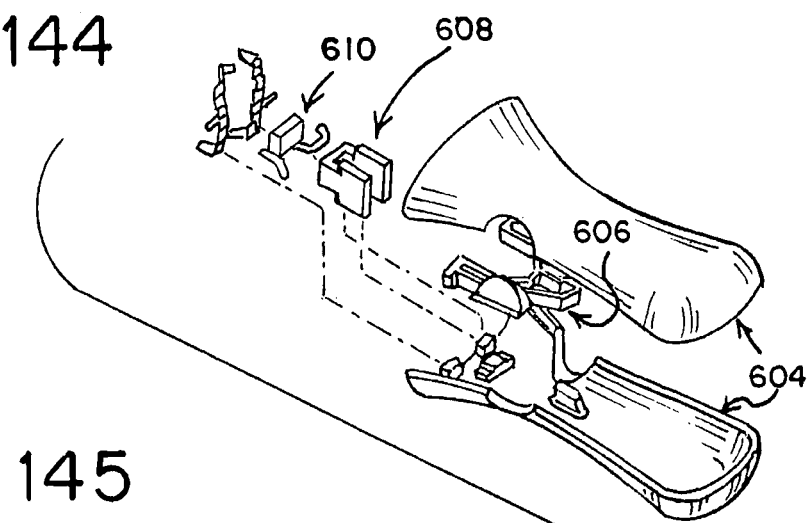
FIG. 145
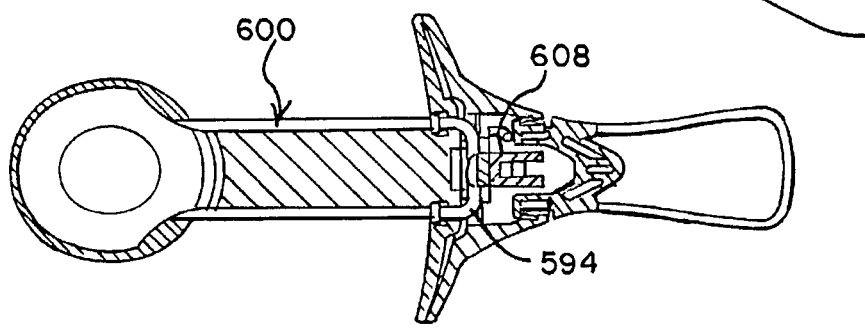
FIG. 146A
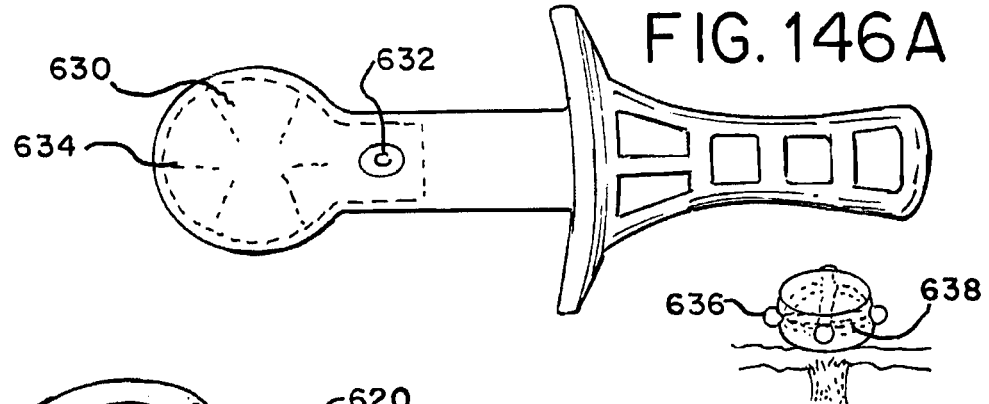
FIG. 146B
FIG. 147
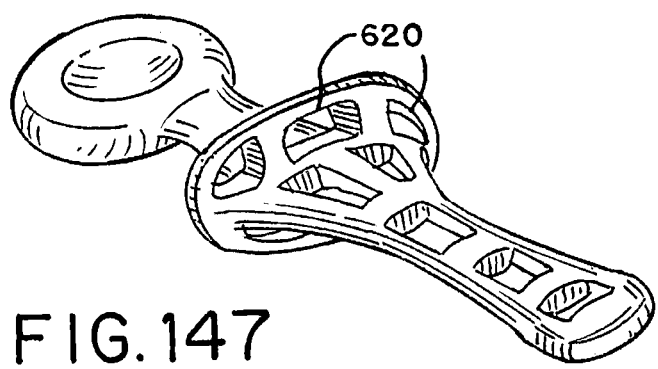

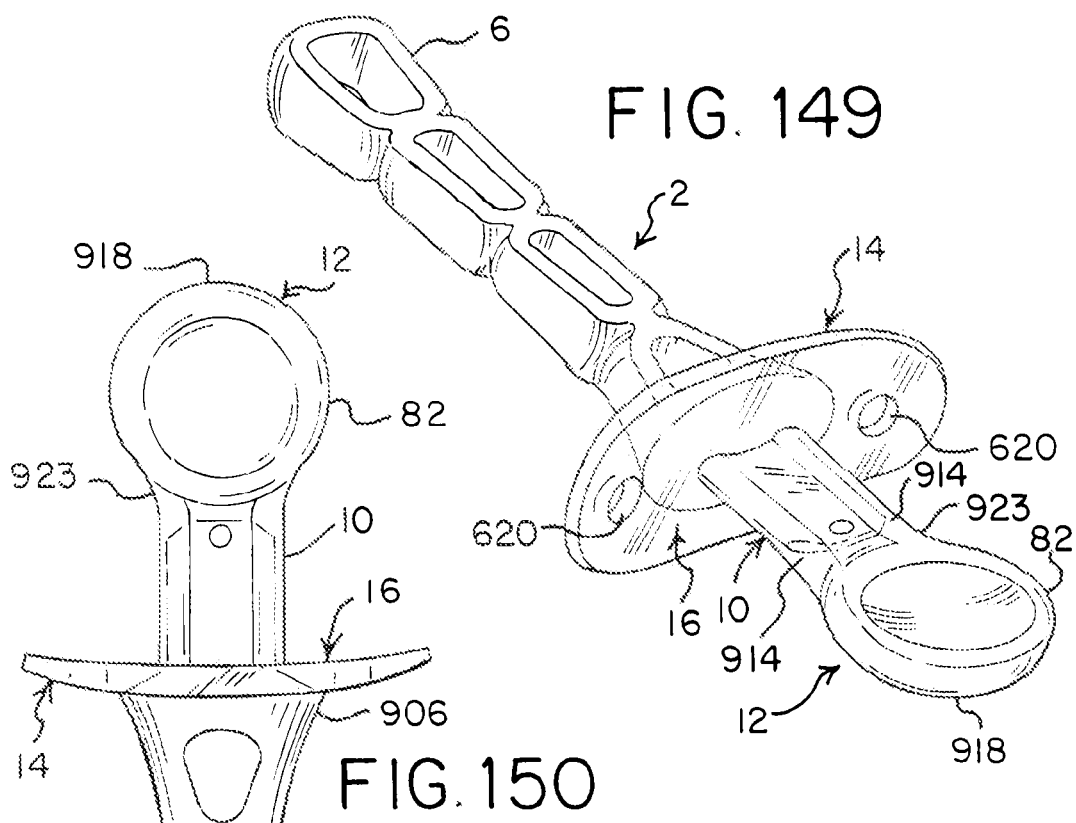
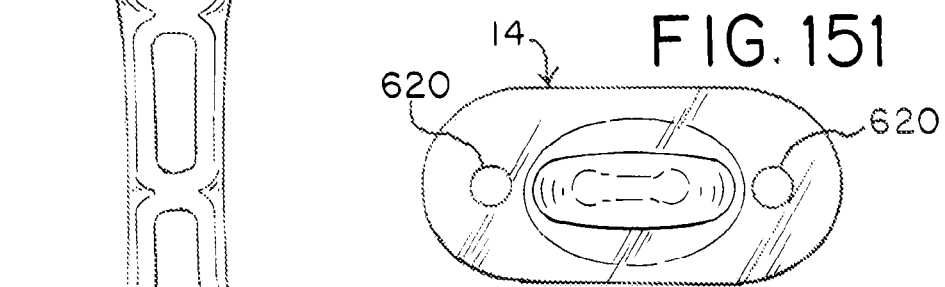
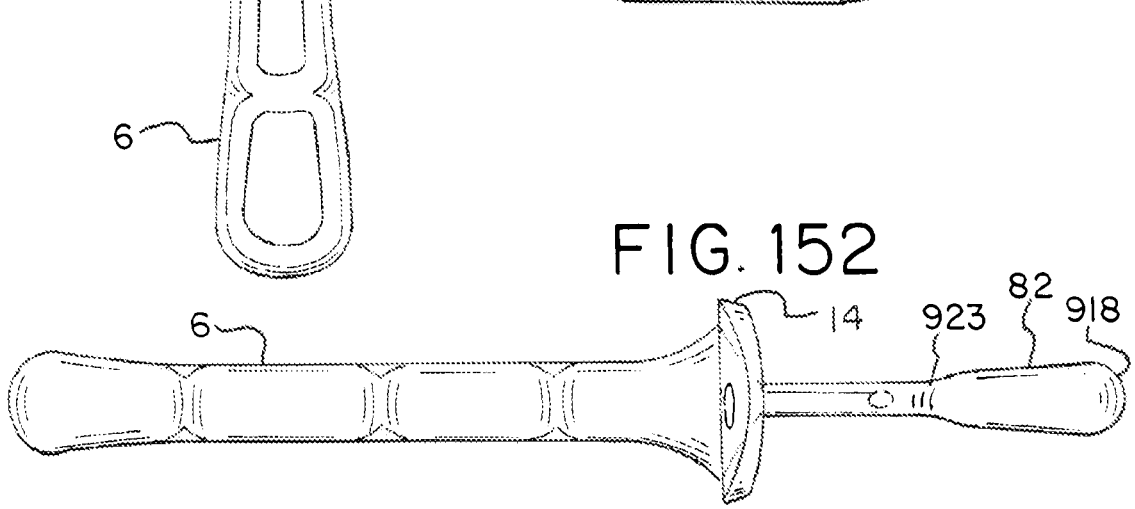

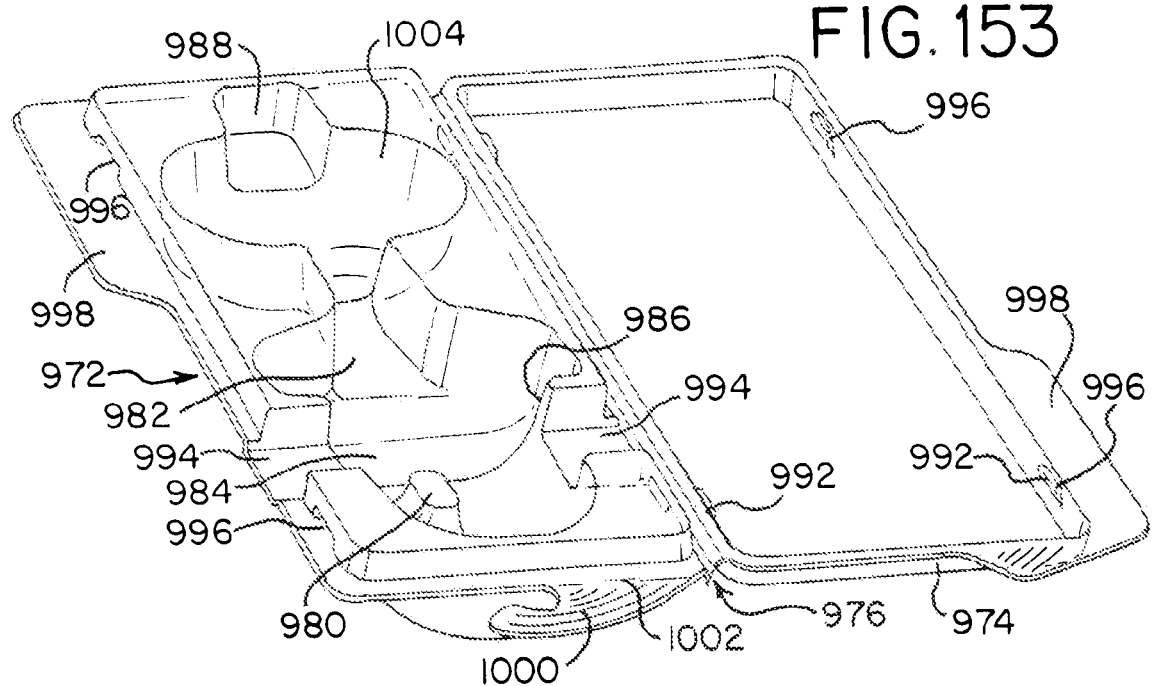
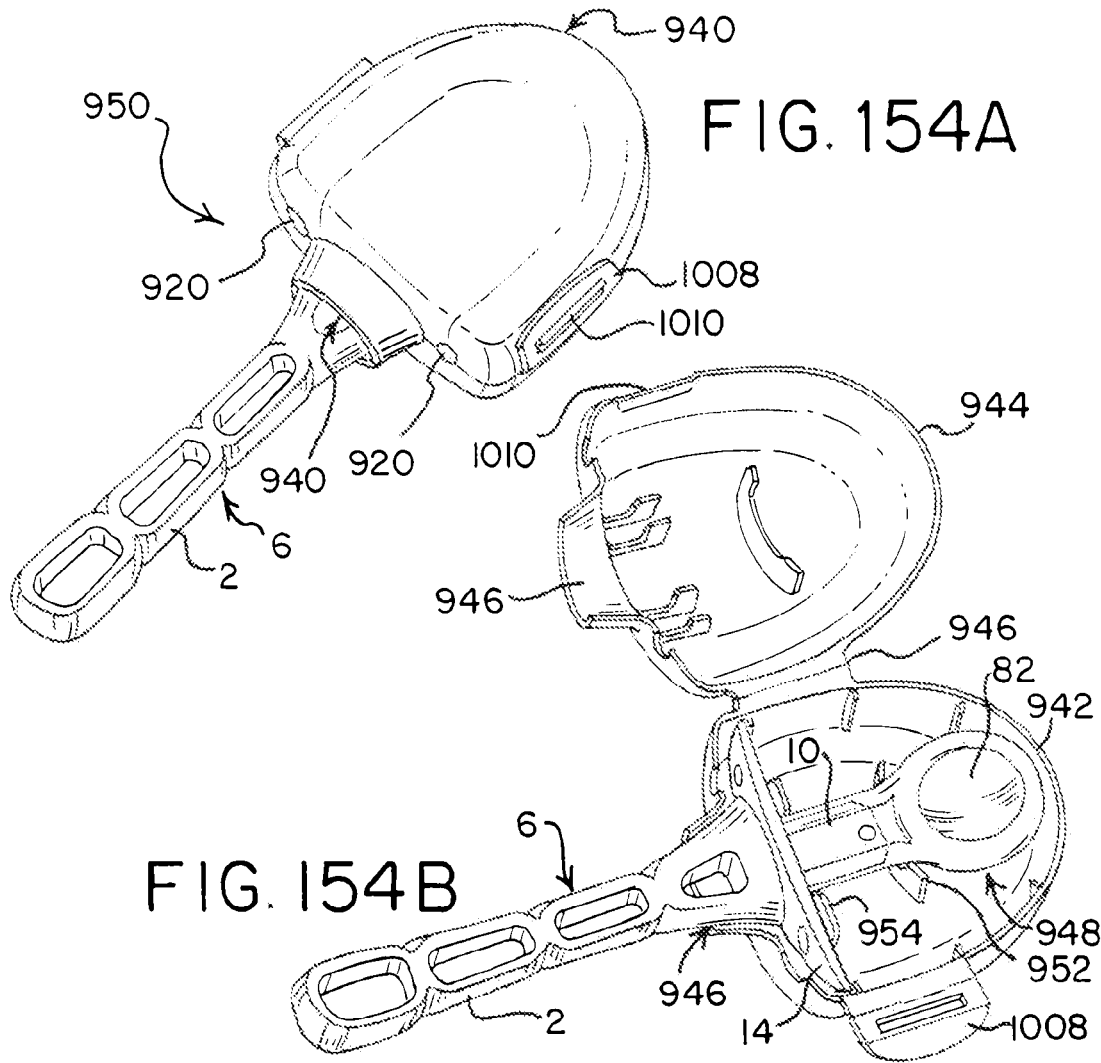

ORAL DEVICE, ASSEMBLY AND METHOD FOR THE USE THEREOF

This application claims the benefit of U.S. Provisional Application 62/265,088, filed Dec. 9, 2015, the entire disclosure of which is hereby incorporated herein by reference.

FIELD OF THE INVENTION

This invention relates to an oral device and in particular a device used to simulate a bolus and/or apply a sensory stimulus to the oral cavity or oropharynx, and to an assembly and travel kit therefore.

BACKGROUND OF THE INVENTION

Swallowing is a complex sensorimotor function that serves the dual functions of transporting material from the mouth to the stomach while protecting the respiratory tract from foreign material. Swallowing involves four stages: the oral preparatory, oral, pharyngeal and esophageal stages. While the oral preparatory and oral stages are under voluntary control, with contributions from the cerebral cortex, the pharyngeal and esophageal stages are autonomic, being controlled by a brainstem network. The pharyngeal stage is triggered when an appropriate pattern of sensory stimulus excites sensory receptors within the oral cavity, oropharynx, and/or pharynx.

Dysphagia, or swallowing impairment, occurs in a number of common diseases and conditions including stroke, cerebral palsy, head and neck cancer, and Parkinson's disease. Dysphagia may affect any or several of the stages of swallowing. For example, a common swallowing abnormality in dysphagia is reduced, or delayed, triggering of the pharyngeal stage of swallowing. As a result, individuals with dysphagia often swallow less frequently when compared with healthy individuals. In addition, when swallowing is performed, the swallow may be slow and/or weak, thus placing the individual at risk of reduced nutritional intake or entry of foreign material into the respiratory tract.

Dysphagia also may result from a lack of saliva, called xerostomia. Xerostomia and associated swallowing impairment occurs in a number of patient diagnostic groups including persons who have undergone radiation therapy in the region of the salivary glands for treatment of cancer of the head or neck, persons with certain systemic conditions, e.g., Sjogren's syndrome, and persons taking medications that reduce salivary flow. When experiencing dysphagia following radiation therapy, patients may perceive their mouths to be even dryer than objective measures of saliva indicate. Unfortunately, the severity of dysphagia is correlated with the degree of perceived mouth dryness. Therefore, both dry mouth and the perception of dry mouth may be problems for patients who have undergone radiation therapy of the head and neck. In addition to the association between dry mouth and dysphagia, dry mouth is unpleasant to the patient, thereby reducing the quality of life.

A variety of stimulus modalities have been applied in attempts to elicit or facilitate swallowing, including electrical stimulation of the pharynx, neck or laryngeal musculature, thermal stimulation of the faucial pillars, modification of diet, exercises, postural adjustments and the use of gustatory stimuli, such as a sour bolus, or combinations thereof. Air-pulse trains also have been considered as a stimulus that may facilitate the pharyngeal swallow. Some devices have been suggested for delivering such air-pulse trains, as disclosed for example in US Patent Publication No. 2010/0016908, published Jan. 21, 2010, the entire disclosure of which is hereby incorporated herein by reference. Air pulse trains are directed to the oral cavity by way of an oral device, which is positioned and secured through various devices. For example, the '908 publication describes, in one embodiment, an "over-the-ear" oral device configured such that the flexible tubing that delivers the air pulse trains wraps around the ears of the user.

SUMMARY

The present invention is defined by the following claims, and nothing in this section should be considered to be a limitation on those claims.

In one aspect, one embodiment of an oral device includes an intraoral bolus simulator comprising an exterior surface and having an interior volume fillable with a fluid. An extraoral user interface extends from the bolus simulator, and may be used to locate or position the intraoral bolus simulator. In various embodiments, the fluid may be a gas or a liquid, or combinations thereof.

In one embodiment, the interior volume may include an inlet and an outlet. The interior volume is reconfigurable from a first volume, wherein the interior volume is filled with a first amount of fluid, to a second volume, wherein the interior volume is filled with a second amount of fluid. A reservoir may be provided, such that the amount of fluid in the device remains fixed, but transferable between the interior volume and the reservoir. In other embodiments, the amount of fluid may be variable, wherein it is introduced by way of a pump.

In one embodiment, a gas passageway may be segregated from the interior volume. The gas passageway extends through the bolus simulator, which includes a gas outlet with the gas passageway. A gas, including without limitation air, may be directed to various regions of the mouth of the user.

In various embodiments, the oral device may be configured with a shield disposed between said intraoral and said extraoral portions. In various embodiments, the shield may be scented, flavoured, or both. In various embodiments, a tether may extend between the shield and the bolus stimulator. The tether may be flexible, and/or may be configured as a fluid passageway, whether to transmit a gas or liquid.

In various embodiments, the bolus simulator may include a solid core, which may be formed for example and without limitation from a flavour impregnated polymer. In other embodiments, the bolus simulator may include a liquid core. In some embodiments, the exterior surface of the bolus simulator, whether defined by the core or by an outer coating, is textured. An outer coating may also be flavoured. In addition, a coating and/or the core may be provided with a pharmaceutical agent, which may be transmitted to the user.

In another aspect, one embodiment of an oral device includes an extraoral handle, a bolus simulator connected to the extraoral handle, and a vibrator coupled to one or both of the extraoral handle and the bolus simulator.

In yet another aspect, an oral device includes an extraoral handle and a bolus simulator connected to the extraoral handle. The bolus simulator includes a bite sensor and at least one electrode exposed on an exterior surface of the bolus simulator and operably coupled to the bite sensor. The electrode transmits a current to the mouth of the user as a function of the amount of force applied to the bite sensor.

In yet another aspect, a method of inducing swallowing includes gripping an extraoral user interface connected to an intraoral bolus simulator, inserting the intraoral bolus simulator into a mouth of a user between the user's tongue and palate, wherein the intraoral bolus simulator has an exterior surface and an interior volume finable with a fluid, manipulating the bolus with the user's tongue, and expelling at least a portion of the fluid from the interior volume.

Other methods of use and of assembling the oral device are also provided. Such other methods of use include, but are not limited to the stimulation of certain oral cranial nerve afferents that are critical for a number of oral sensory motor behaviours such as without limitation mastication, speech production and salivation.

In another aspect, an oral device assembly includes a carrying case having first and second clam shell members hingedly connected along one side thereof. The first and second clam shell members define an interior cavity when in a closed position. An oral device includes handle, a tether coupled to the handle and an intraoral bolus simulator coupled to the tether. At least a portion of the oral device is disposed between the first and second clam shell members with a support member engaging and supporting the said oral device such that the intraoral bolus simulator is suspended in the interior cavity free of any engagement with the carrying case when the first and second clam shell members are in said closed position.

In yet another aspect, an oral device includes an intraoral bolus simulator having a fluid filled bulb portion with opposite faces. First and second lubricated patches are disposed on the opposite faces. The lubricated patches are transformable in response to an application of a liquid from a first state, wherein the lubricated patches each comprise water soluble thermoplastic particles suspended in a silicone matrix, to a second state, wherein the water soluble thermoplastic particles are depleted from the silicone matrix.

In another aspect, a method of stimulating an oral cavity includes disposing an intraoral bolus simulator in an oral cavity of a user, presenting a smooth surface to the user with the lubricated patches, contacting the lubricated patches with saliva and thereby depleting the water soluble thermoplastic particles from the silicone matrix, and presenting a rough surface to the user with the lubricated patches after the water soluble thermoplastic particles are depleted from the silicone matrix.

The various embodiments provide significant advantages over other types of treatment modalities for various swallowing impairments. For example and without limitation, various embodiments of the oral device may provide for multiple stimuli, including without limitation, gustatory, scent, somesthetic, thermal and auditory stimuli. In applicable embodiments, the fluid bolus may provide a more accurate simulator than solid devices, while at the same time providing in some embodiments an additional air pulse stimulant. In some embodiments, the end of use feature alerts the user that certain feature, such as lubricants or coatings, have been depleted and that it is time to use a new device.

The device is extremely portable and easy to use. The carrying cases provide a convenient, sanitary assembly for transporting and/or storing the device, while maintaining the isolation of the bolus simulator from any contact surface, thereby insuring that the integrity of any end of use features is preserved. Many embodiments provide for the user to use the device on their own, for example at home. At the same time, the device is provided with various safeguards, such as a shield and tether, which prevent the bolus simulator from being swallowed and/or blocking the patient's airway. In addition, in some embodiments, the device may be provided with means to deliver pharmaceutical and/or antiseptic agents.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIGS. 7A-C provide perspective views of an alternative embodiment of closed and open molds with an insert component disposed in one of the mold components.

FIGS. 8A-C provide perspective views of an alternative embodiment of closed and open molds with an insert component disposed in one of the mold components.

FIG. 9 is a perspective view of one embodiment of an oral device.

FIGS. 10A and B are perspective views of an alternative mold configuration.

FIGS. 11 and 12 are perspective views of an alternative mold configuration.

FIGS. 13 and 14 are perspective views of an alternative mold configuration.

FIG. 15 is a perspective view of an alternative embodiment of an oral device.

FIG. 16 is a perspective view of a handle incorporated into the embodiment of FIG. 15.

FIGS. 17A and B are perspective views of a mold set and mold for one embodiment of a handle.

FIG. 18 is a cross-sectional view of the oral device shown in FIG. 15.

FIG. 19 is a perspective view of one embodiment of a mold core.

FIG. 20 is a partial, enlarged perspective view of valves overmolded on the handle.

FIG. 21 is a perspective view of lost core wax insert.

FIG. 22 illustrates a duck bill valve core coupled to the handle.

FIG. 23 is a perspective view of an alternative embodiment of an oral device.

FIG. 24 is a perspective view of an alternative embodiment of an oral device configured with a single gas passageway.

FIG. 25 is a perspective view of an alternative embodiment of an oral device configured with a pair of gas passageways.

FIG. 26A is a side cross-sectional view of one embodiment of an oral device with a fluid filled bolus simulator being manipulated inside a user's mouth.

FIG. 26B is a side cross-sectional view of the oral device shown in FIG. 26A positioned near the back of the mouth and delivering a gas pulse.

FIG. 36 is a partial perspective view of an alternative embodiment of an oral device.

FIG. 37 is a cross-sectional view of the oral device shown in FIG. 36 taken along line 37-37.

FIG. 38 is a partial perspective view of an alternative embodiment of an oral device.

FIG. 39 is a partial perspective view of an alternative embodiment of an oral device.

FIG. 40 is a top view of the oral device shown in FIG. 39.

FIG. 41 is a cross-sectional view of the oral device shown in FIG. 40 taken along line 41-41.

FIG. 42 is a perspective view of a self-inflating oral device.

FIG. 43 is a partial, cross-sectional view of the oral device shown in FIG. 42.

FIGS. 44A-E are various views of an alternative embodiment of a oral device.

FIG. 45A is a perspective view of the oral device shown in FIG. 44 as applied to a user.

FIG. 45B is a perspective view of the oral device shown in FIG. 45A prior to application to a user.

FIGS. 46A-F are various views of one embodiment of an oral device.

FIGS. 47A-F are various views of one embodiment of an oral device.

FIGS. 52A-E are various views of one embodiment of an oral device.

FIGS. 53A-E are various views of one embodiment of an oral device.

FIGS. 54A and B are cross-sectional side views of an oral device with a self-inflating bolus simulator after being inflated and then deflated.

FIG. 57A-D are various views of one embodiment of a handle for an oral device.

FIG. 58A-E are various views of one embodiment of a bolus simulator and tether.

FIG. 59A-E are various views of a shield for an oral device.

FIG. 60 is an exploded view one oral device embodiment.

FIG. 61 is an exploded view of an alternative embodiment of an oral device.

FIG. 62 is an exploded view of an alternative embodiment of an oral device.

FIG. 63 is an exploded view of an alternative embodiment of an oral device.

FIG. 64 is an exploded view of an alternative embodiment of an oral device.

FIG. 65 is an exploded view of an alternative embodiment of an oral device.

FIG. 66 is an exploded view of an alternative embodiment of an oral device.

FIG. 67 is an exploded view of an alternative embodiment of an oral device.

FIGS. 71A-C are various views of an oral device.

FIGS. 72A-D are various view of a bolus simulator.

FIGS. 73A-F are various views of an oral device.

FIGS. 74A-F are various views of a bolus simulator.

FIGS. 75A-E are various views of a shield.

FIGS. 76A-E are various views of a handle.

FIGS. 77A-D are various views of an oral device.

FIGS. 78A-G are various views of an oral device.

FIGS. 79A-C are various views of an oral device.

FIGS. 80A-D are various views of an oral device.

FIGS. 81A-E are various views of an oral device.

FIGS. 82A-E are various views of a handle for an oral device.

FIGS. 83A-E are various views of an oral device.

FIGS. 84A-E are various views of a handle for an oral device.

FIGS. 85A-G are various views of a bolus simulator for an oral device.

FIGS. 86A-F are various views of a valve arrangement for an oral device.

FIGS. 87A-E are various views of an oral device.

FIGS. 88A-E are various views of a bolus simulator for an oral device.

FIG. 89 is a top view of an oral device.

FIG. 90 is a cross-sectional view of the oral device shown in FIG. 89 disposed in a user's mouth.

FIG. 91 is a cross-sectional view of the oral device shown in FIG. 89 disposed in a user's mouth during operation.

FIG. 92 is top view of an oral device.

FIG. 93 is a cross-sectional view of an oral device during operation.

FIG. 94 is a top view of an oral device during operation.

FIG. 95 is a perspective view of an oral device disposed in a mouth of a user.

FIG. 96 is a perspective view of an oral device disposed in a mouth of a user.

FIG. 97 is a perspective view of a bolus simulator.

FIGS. 100A-F show various view of an oral device.

FIG. 103 is a cutaway view showing the connection between the intraoral portion and the handle of FIG. 101.

FIG. 104 is a front view showing the catch mechanism included in the embodiment of the oral device shown in FIG. 101.

FIG. 105 is a side view showing the catch mechanism of FIG. 104.

FIG. 106 is a perspective view of an alternative embodiment of an oral device.

FIG. 107 is a perspective view of an alternative embodiment of an oral device.

FIG. 108 is a perspective view of an alternative embodiment of an oral device.

FIG. 109 is a perspective view of the oral device shown in FIG. 108 as applied to a user.

FIG. 110 is a top plan view of the oral device shown in FIG. 106.

FIG. 111 is a cross-sectional view of the oral device shown in FIG. 110 taken along line 111-111.

FIG. 112 is a side view of the oral device shown in FIG. 106.

FIG. 113 is an enlarged partial view of the oral device shown in FIG. 111 taken line 113.

FIG. 114 is a cross-sectional view of an oral device applied to a user.

FIG. 115 is a perspective view of an alternative embodiment of a bolus simulator.

FIG. 116 is a top view of the bolus simulator shown in FIG. 115.

FIG. 117 is a cross-sectional view of the bolus simulator shown in FIG. 116 taken along line 117-117.

FIG. 119 is a partial cut-away view of the oral device shown in FIG. 118.

FIG. 120 is an enlarged partial view of the bolus simulator shown in FIG. 118 inserted in a mouth of a user.

FIGS. 121-123 show different stages of the assembly of an oral device.

FIGS. 124-126 show different stages of the assembly of another oral device.

FIGS. 127A-C show different stages of the assembly of another oral device.

FIG. 128-136 show an alternative bolus reinforcement structures.

FIGS. 137-147 show various alternative embodiments of an oral device.

Figure 148A:
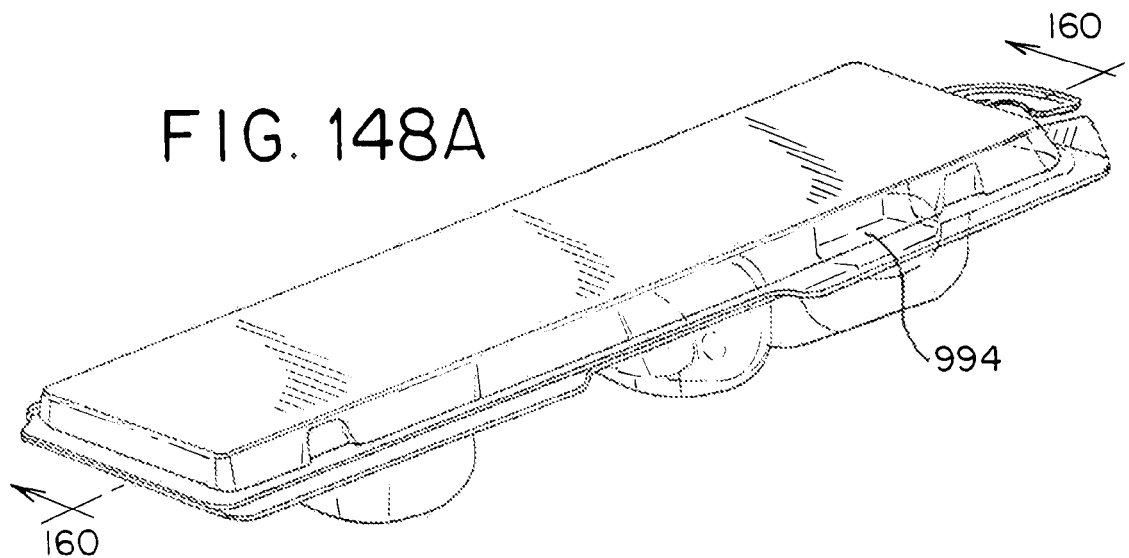

FIGS. 148A and B shows perspective views of one embodiment of a closed and open carrying case with an oral device disposed therein.

FIG. 149 is a perspective view of one embodiment of an oral device.

FIG. 150 is a front view of the oral device shown in FIG. 149.

FIG. 151 is a top view of the oral device shown in FIG. 149.

FIG. 152 is a side view of the oral device shown in FIG. 149.

Figure 148B:
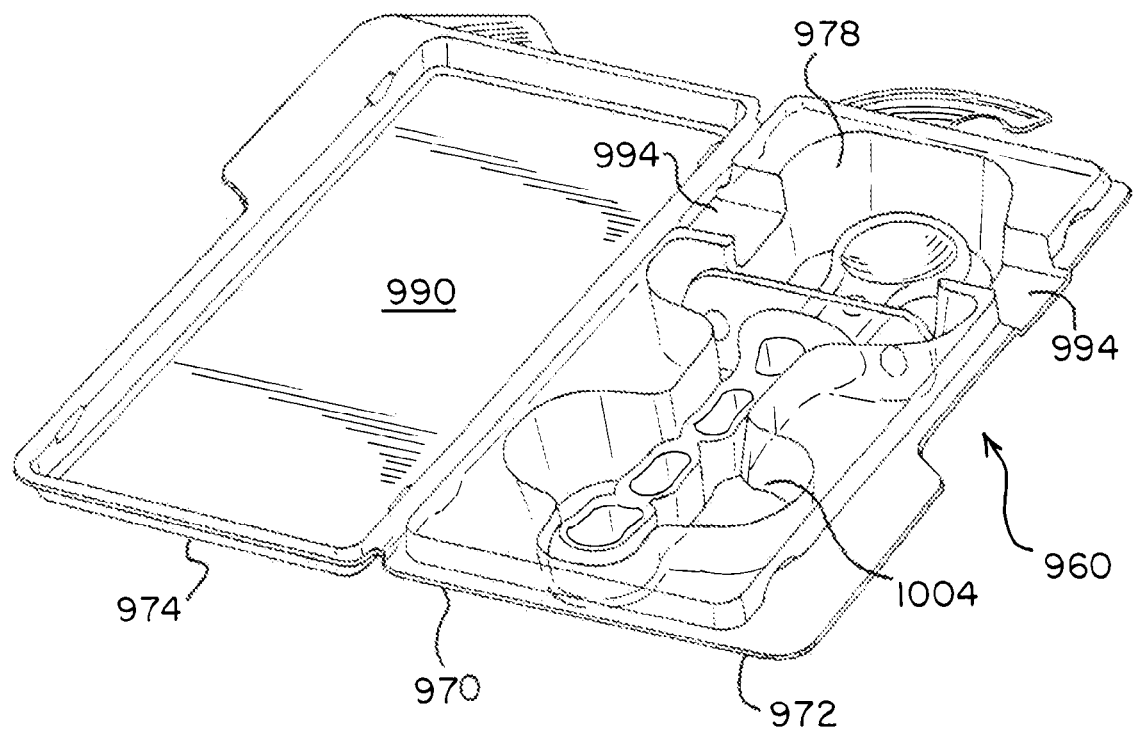

FIG. 153 is a rotated perspective view of the open carrying case shown in FIG. 148B without the oral device.

FIGS. 154A and B shows perspective views of another embodiment of a closed and open carrying case with an oral device disposed therein.

Figure 155:
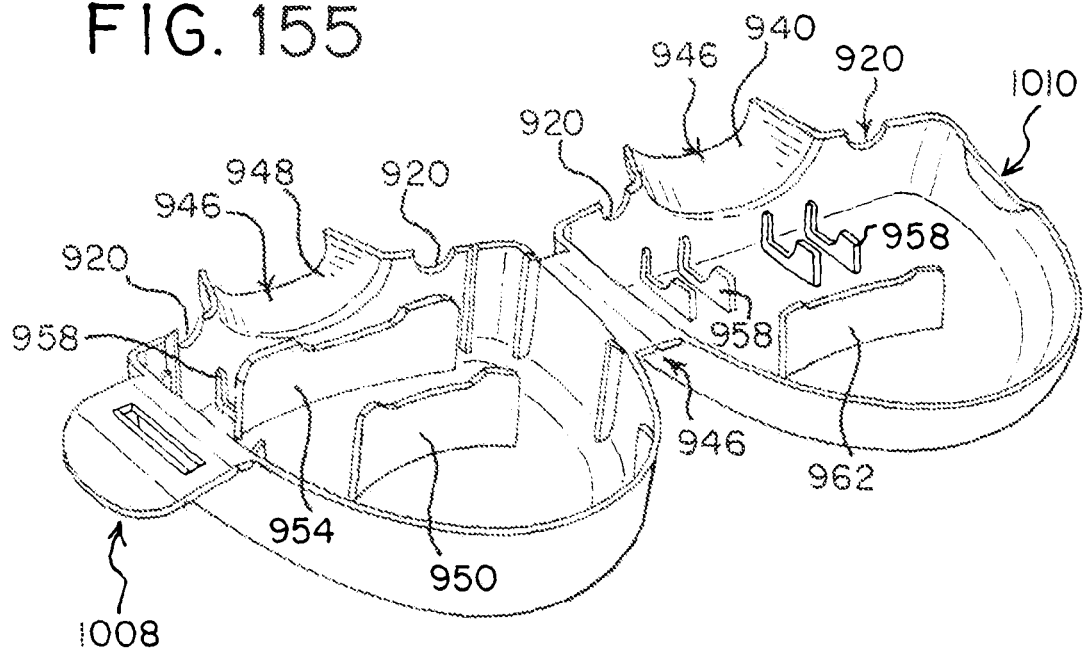

FIG. 155 is a perspective view of the open carrying case show in FIG. 154B without the oral device.

Figure 156:
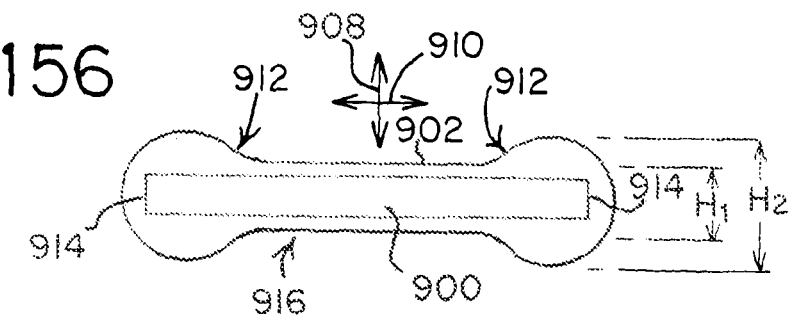

FIG. 156 is a cross-sectional view of one embodiment of a tether.

Figure 157:
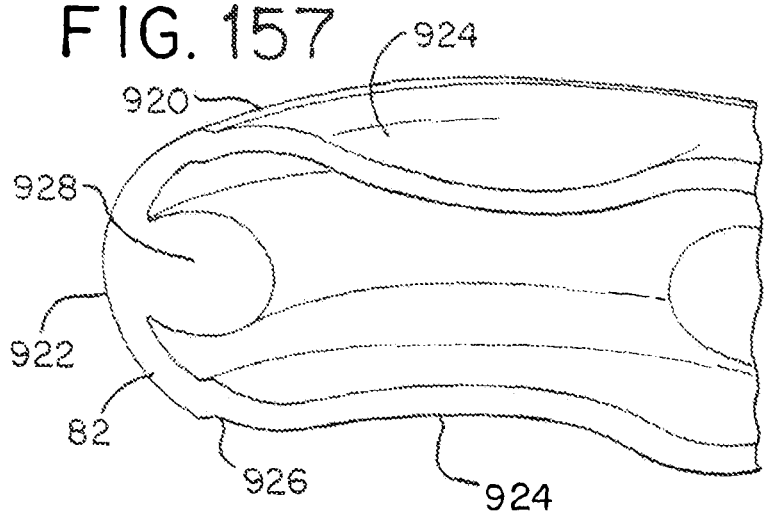

FIG. 157 is a partial, cross-sectional view of one embodiment of a bolus simulator.

Figure 158:
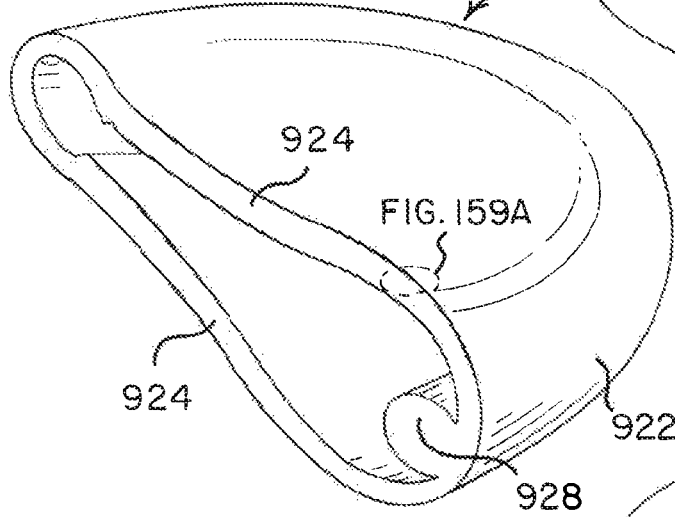

FIG. 158 is a partial, cross-sectional view of one embodiment of a bolus simulator.

Figure 159A:
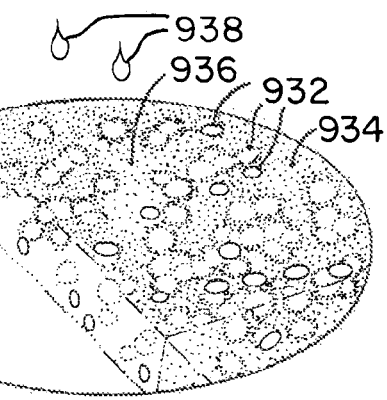
Figure 159B:
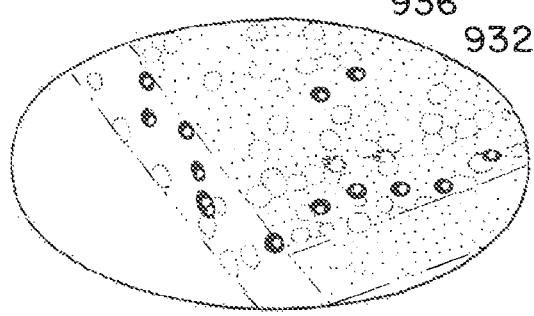
Figure 159C:

FIGS. 159A-C are enlarged partial views of a portion of lubricated patch portion of a bolus is an original, partially depleted and completely depleted state respectively.

Figure 160:
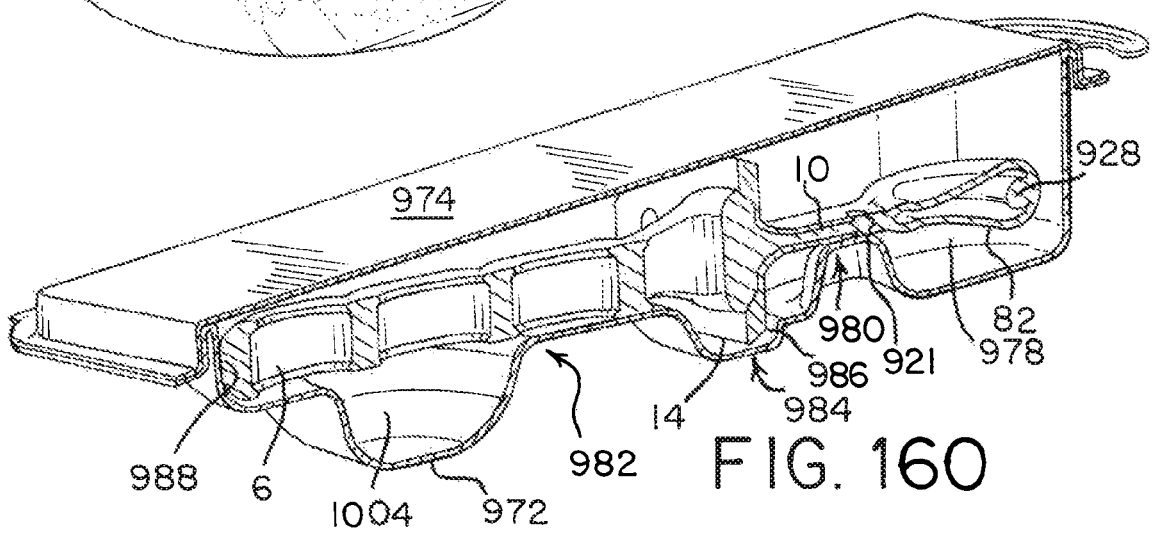

FIG. 160 is a cross-sectional view of the carrying case and oral device taken along line 160-160 of FIG. 148A.

DETAILED DESCRIPTION OF THE DRAWINGS AND THE PRESENTLY PREFERRED EMBODIMENTS

The term "lateral," "laterally," and variations thereof refer to the widthwise or side-to-side direction between the cheeks of the user. The term "longitudinal," "longitudinally," and variations thereof refer to the lengthwise direction of a component. The term "upper" or "above" refers to the vertical direction or orientation towards the roof of the mouth of a user when sitting upright, while the term "lower" or "below" refers to the vertical direction or orientation towards the ground. The term "radially" refers to extending outwardly from, but is not limited to features extending outwardly from a single center point, meaning for example a feature(s) may extend radially outwardly from a line segment. The term "fluid" refers to either a gas or a liquid, or combinations thereof, including liquids with particles or solids suspended therein. It should be understood that when referring to "first" and "second" herein, it should be understood that any terms modified thereby, including for example volume and amounts of fluid, may vary between many different measures, not just two defined measures, and that the volume and amount of fluid may be infinitely adjustable along a continuum, with "first" and "second" merely referring to two different measures along such a continuum of such measures.

Extraoral User Interface

Turning now to the drawings, FIGS. 23, 25, 27, 42, 46, 47, 60-70 and 149-152, an oral device 2 is shown as including an extraoral user interface 4. The extraoral user interface may be configured with a contoured handle 6, having various grippable features, such as ribs, knurls or other features. In various embodiments, the extraoral portions may be constructed from medical grade or other materials. For example, the extraoral portions may be made of Saint-Gobain Tygon Plastic Tubing, PolyFlav+EVA flavored plastics and/or Saline solution, 3D Systems Rapid Prototype Resin and/or Cast Urethane.

A shield 14, also forming part of the extraoral interface 4, is coupled to an intraoral member 8, configured in one embodiment with a bolus simulator 12 and tether 10. In one embodiment, the shield 14 is integrally formed as part of the extraoral interface, and is configured as a thin flange extending transversely to a longitudinal axis of the handle, or radially outwardly from the handle. Referring to FIGS. 50, 51, 59, 64, 75, 149, 150 and 152 the shield 14 may have a slight concave contour 16 facing the bolus simulator so as to conform to the face of the user. The outer, lateral edges 18 of the shield are flared outwardly, forming a concave contour 20 relative to a horizontal axis, and running transverse to the curved contour 16 formed about the vertical axis. The shield may be made of a hard plastic material such as polypropylene, polyethylene and/or nylon, including mineral filled or glass filled variations thereof, and may be scented, for example using a scenting agent. The shield also may be made of polycarbonate and phthalate and lead free polyvinyl chloride (PVC). In one embodiment, if more flexibility is desired, 70- to 90 Shore A durometer silicone material may be used. In one embodiment, the handle is made of polyethylene or polypropylene, while the shield is made of PolyFlav+EVA. In various embodiments, the shield is configured with one or more openings 201 or slots 52, 203 that receive the tether and/or provide through holes for fluid conduits 70, 56, 62, 66, 42, whether for a gas or liquid, and also a slot or groove 203 that receives and surrounds a portion of the handle as a support structure 22 is inserted into an interior of the shield.

In one embodiment, shown in FIGS. 48 and 49, the handle is provided with a shield support structure 22 extending substantially transverse to the handle. The support structure is configured in one embodiment as a flange with a plurality of alternating ribs 24 and recesses 26. The shield 14, shown in FIGS. 50, 51, 59 and 75, includes a shroud or cover that fits over and surrounds the internal support structure 22, thereby allowing the user to alter the materials interfacing with the outer lips and face of the user. Moreover, the outer cover portion of the shield 14 may be replaced, and/or the handle 6 removed for sanitizing. The shield may be formed as an inseparable assembly with a soft polymer user interface 14 overmolded or co-molded with the support structure 22, with the support structure made of one or more of the materials disclosed above. The outer casing, or interface material, of this two-shot component may be made of EVA, flexible PVC and/or silicone. The durometer values for the outer overmolded materials may range from 30 Shore A to 80 Shore A. Various scenting agents may be incorporated into the polymer or silicone material making up the outer user interface layer. The shield may be flavored or scented by way of material impregnation, or by mechanical bonding through dipping or coating. Portions of the shield may be flavored or scented, or the shield may be free of any such agents. In one embodiment, the outer user interface layer, which encases the support structure 22, is formed as a one piece injection molded part overmolded onto the support structure.

In other embodiments, the shield 14 is co-molded with an outer casing or skin portion 902 of the tether 10 and also the bolus simulator 12, and is over-molded on an end portion 906 of the handle and a core portion 900 of the tether (which are co-molded), as shown in FIGS. 149, 150 and 160. As further explained below, the handle 6 and core 900 may be made of a harder, stiffer material, with the casing or skin 902 made of a material that is softer and more flexible than the material of the core and handle. An anchor portion 921 may extend from the core of the tether and help anchor the casing and shield.

The shield 14 prevents the bolus simulator, or other intraoral portions, from travelling too far into the mouth cavity of the user, wherein the intraoral portion may induce a gag reflex or present a choking hazard. In addition, the shield functions as a barrier that prevents saliva or other deposits adhered to the intraoral portion from contaminating the extraoral portion, such as the handle, or the user's hand. Like the handle, it is preferable to provide the shield with aesthetic properties that avoid conjuring up an image of a device for use with infants or small children, such as a pacifier. The shield may also provide a measurement device, advising as to how far the bolus simulator has been inserted into the user's mouth.

Referring to FIGS. 147, 149 and 151, the shield may include vent holes 620. In the embodiment of FIGS. 149 and 151, the shield includes a pair of holes 620, one positioned on each side of the tether, which may be aligned with openings 920 in a carrying case as further explained below. The alignment of the vent holes 620, 920 ensures maximum air circulation when the oral device is in a stored position within a carrying case 940. The vent holes also prevent choking in the event that the device gets dislodged in the patient's breathing air path.

Referring to FIGS. 95 and 96, a positioning handle 28 may be made of a thin, narrow strip of rigid, but deformable, material. One end of a tether portion 40, or intraoral portion, of the handle may have the same proximate shape, but with lesser dimensions, as the bolus simulator 32, thereby providing internal support for the bolus simulator. The handle may be smooth and light weight such that it does not cause injury to the oral tissues. Referring to FIGS. 106, 107, 110 and 111, the handle may be provided with lightening holes 316. A lanyard hole 318 may be provided at a distal end of the handle. In one embodiment, the overall weight of the oral device is less than or equal to 40 grams. The lightening and lanyard holes 316, 318 are sized and positioned to locate the center of mass of the oral device near the proximal end of the handle to minimize the distance from the device's centroid and the center of mass, which minimizes the pendulum effect of the handle with the device is being used off-hand. As shown in FIG. 113, a portion 320 of the handle protrudes into the center of the tether to provide a reinforcement for the tether core. While configured as a slender body, the handle may also be configured as a knob or loop.

The handle may be configured with a bright color such that it is easily seen. In one embodiment, the tether portion 40 of the handle exits the mouth of the user anteriorly between the upper and lower teeth, where it deforms to the occlusal relationship of the upper and lower teeth as the jaw is closed after positioning the bolus simulator, thereby allowing for use with the teeth in occlusion. The handle 28 includes an intermediate portion 34 that extends downwardly as the tether portion 40 is deformed, and a grippable portion 36 that extends outwardly for grasping by the user. In another embodiment, the handle exits from the lateral aspects of the bolus simulator and exits the mouth at the angle of the mouth, passing between the upper and lower teeth posterior to the canine at a point where the contacting surfaces of the upper and lower teeth are not in contact.

In yet another embodiment, shown in FIG. 96, a pair of positioning handles 30 exit the right and left sides of the end of the bolus simulator and exit the mouth at an angle, one handle 30 attached to and stabilizing the right side of the bolus simulator and the other attached to and stabilizing a left side. In one embodiment, the two positioning handles 30 extend downwardly, outwardly and then upwardly, terminating in hook portions 38 that may be secured over the ears of the user to further stabilize the bolus stimulator while also freeing up the hands of the user or operator of the device.

In one embodiment, the handle 28, 30 and bolus simulator 32, as well as a tether and shield, are permanently affixed such that they may not be separated, with the assembly being particularly well suited for a single use, single session, or for several sessions by a single user.

Figure 102:
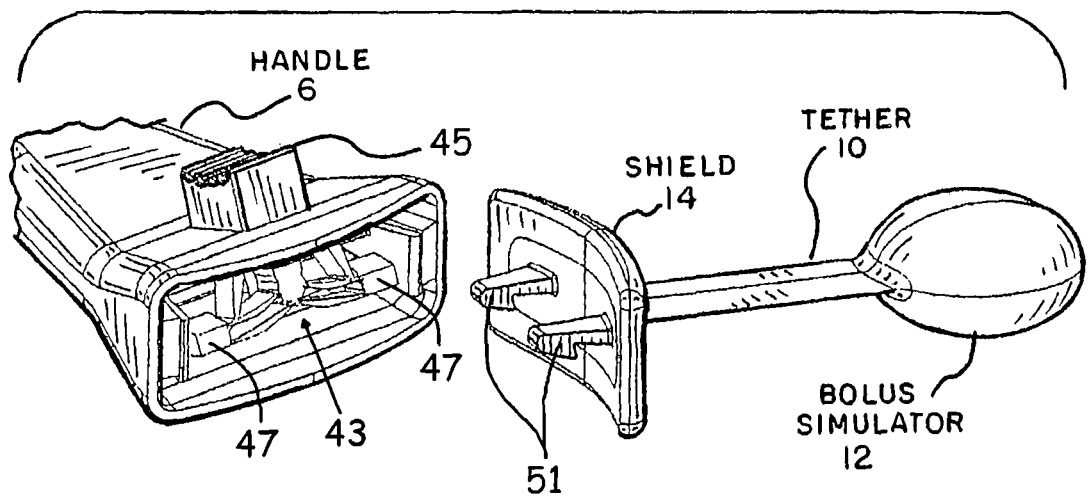
FIG. 102 is a partial, perspective view of a handle and intraoral portion shown in FIG. 101 in a released configuration.
Figure 118:
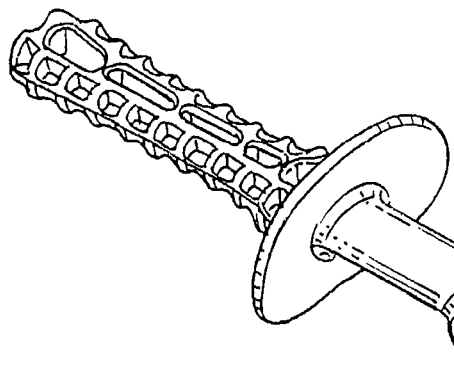
FIG. 118 is a partial perspective view of an alternative embodiment of an oral device.
Figure 119:
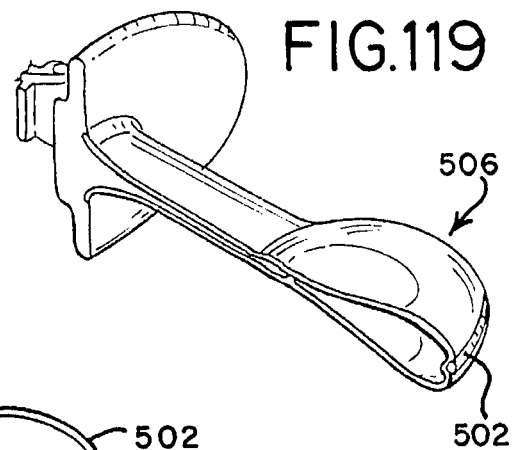
Figure 120:
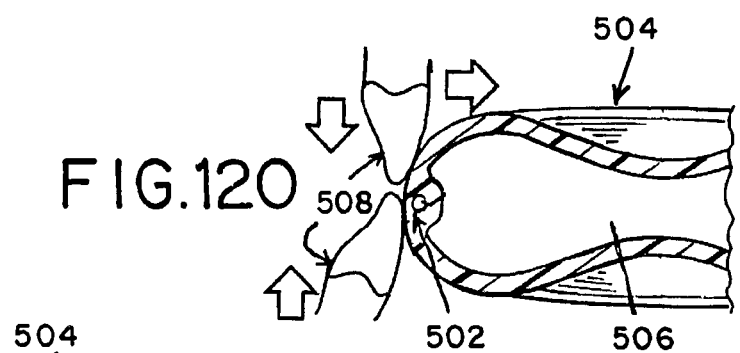

Alternatively, as shown in FIGS. 62-67, 77C and 79C, the handle 6 may be releasably connected to the bolus simulator 12 with a tether 42, for example with a clip, snap-fit or engagement with a catch member 43, such that the handle 6 may be separated, cleaned and reused with another bolus simulator 12. Referring to FIGS. 101-105, the handle incorporates a catch member 43 that allows the intraoral portion 8, along with the shield 14, to be detached or released from the handle 6. FIG. 102 shows the detachable handle in a released or separated state revealing the catch mechanism 43. As shown in FIGS. 102-105, the handle includes an actuator, shown as a button 45, with a coupled to a pair of laterally spaced catch members 47 connected with a bridge member 53. The catch members 47 have an angled surface forming a wedge configuration. The actuator is connected to the catch members with a pair of legs 49, which function as a spring to return the actuator to an engaged position. The shield 14 is configured with a pair of hooks or catch members 51 that extend longitudinally from the shield. In an assembled configuration, the handle's twin wedge feature 47 is engaged by the catch members 51 so as to releasably couple the shield and the intraoral subassembly to the handle. As illustrated in FIGS. 104 and 105, releasing the shield 14 and intraoral portion 8 is accomplished by pressing the button 45 located in the middle of the catch member 43 and thereby moving the twin retaining wedge features 47 in the same direction of the movement of the button 45, away from the catch members 51 attached to the shield. This allows the shield and intraoral portion to be moved longitudinally out of engagement with the handle. Insertion is accomplished by movement in the opposite longitudinal direction, with the catch members 51 either biasing the wedge members 47, or with an assist from the button, until they are released into a releasable snap-fit configuration.

In one embodiment, the handle 6 may be configured with a vibratory element that imparts a vibration to the bolus simulator. For example and without limitation, a vibration in the frequency range of 2 to 70 Hz may be applied. The vibration may be initiated manually by the user or care giver through actuation of a button on the handle. Alternatively, the vibration may be triggered by movement of, or pressure applied to, the bolus simulator by the user.

In another embodiment, the handle may also be configured to emit a verbal cue, for example a human voice providing instructional information, for example "Get ready to swallow, swallow hard," etc. The verbal cue may be initiated manually by the user or care giver through actuation of a button on the handle 6. Alternatively, the cue may be triggered by movement of, or pressure applied to, the bolus simulator by the user.

In various embodiments, the handle may be made of the same types of materials as the shield, including a hard durometer (80 Shore A) silicone. In another embodiment, the handle includes a hard main core over molded with a softer material, such as silicone, flexible PVC or EVA with durometer values ranging from 40 Shore A to 80 Shore A.

Referring to FIGS. 44 and 45A and B, another embodiment of an oral device is shown. The oral device includes a pair of laterally spaced intraoral portions 112 defining intraoral conduits each having at least one outlet port 120 adapted to dispense at least one fluid pulse. An extraoral portion 114 is integrally formed with each of the intraoral portions. The extraoral portions define extraoral conduits in flow communication with the intraoral conduits. An auxiliary support device includes a yoke. In one embodiment, the yoke is configured as a Y-shaped frame 132 having a pair of arm portions 134 and an inlet portion 136, each configured with grooves or channels in which the extraoral portions are disposed and secured. The arm portions curve rearwardly from the inlet portion. In one embodiment, the arm portions extend at an angle α of about 20-60 degrees, and in one embodiment at an angle α of about 30-45 degrees, and in one embodiment at an angle α of 38.5 degrees. The frame shapes and holds the extraoral portions 114. In addition, each of the pair of arm portions 134 includes a wing with an attachment member 140. At least one securing member 142, configured for example and without limitation as an elastic band, may be secured to the attachment members 140. The band may be configured as a pair of ear loops, or as a single headband that encircles the user's head and locates and holds the yoke in position.

In one embodiment, wing portions have a concave curved portion 144 that interfaces with the lips, or corner of the user's mouth, with the end portions of the yoke arms 134 extending into, and positioning intraoral portions 112 of the tubing, in the mouth of the user. In essence, the end portions and the attachment member 140 have a recess formed therebetween so as to locate the yoke relative to the user, and the lips/mouth in particular, with the force applied by the securing member 18 urging the yoke against the user's lips/mouth. The width (W) of the wing may be widened at the junction of the end portions and the wings at the area of contact with the user's lips/mouth so as to reduce the tissue contact pressure.

Referring to FIGS. 15, 16, 18, 24, 25, 27 and 28, fluid passageways 56 extend through the handle 6 and communicate with input ports 60 at distal end of the handle. Alternatively, the passageways, configured as conduits 56, extend from the handle. A fluid supply, such as a compressor or pump (hand or motor driven), may be coupled to the inlet ports 60 or conduits to supply a gas. The conduits 56 may be open to the ambient environment, or may be coupled to a gas source, such as oxygen, wherein other medicaments may be introduced into the gas passageway and delivered to the user. Alternatively, a liquid may be supplied to the inlet ports.

The purpose of the handle 6 is to be used in the insertion and extraction of the intraoral part of the device from patient's mouth, as well as a means to help maneuver the bolus simulator 12 inside the patient's mouth. To serve that purpose well, the handle shall be ergonomically friendly. In addition, since in the intended treatment regiment the intraoral portion may be left inside the patient's mouth for an extended period of time, the handle 6 should be light enough that it does not have to be supported externally while the intraoral component 8 is in the patient's mouth without causing discomfort.

From an aesthetic standpoint, while the handle 6 shall retain its ease-of-use characteristics, especially for someone with impaired fine motor skills, the handle should not conjure up any negative perceptions to the intended users or patients. As an example, for patients with early onset of dementia, who are otherwise able to lead a normal social life, having to use a device that resembles something that is intended for an infant or a severely disabled person, can be quite disheartening.

Tether

The oral device also includes various intraoral components, including a tether 10 and a bolus simulator 12. In various embodiments, the intraoral components are constructed from medical grade material. For example, the intraoral components may be made of Dow Corning Silastic M room Temperature Vulcanization (RTV) Silicone, Dow Corning Silastic MDX4 RTV Silicone, Saint-Gobain Tygon Plastic Tubing, 0.04 inch Clear Mouth Guard Thermo-Forming EVA sheets, PolyFlav+EVA flavored plastics, PVC (lead and Pthhalate free), EVA, and/or Saline solution. In one embodiment, the tether is made of a composite of fully cross-linked soft silicone outer casing or skin 902, and a harder silicone core 902, shown for example in FIG. 156. This construction, with its stiffer core, laterally elongated geometry and correspondingly defined moment of inertia, ensure that the bolus simulator may move up and down along a transverse direction 908 by way of bending the tether, but its movement is restricted in a lateral direction 910, which permits the user to control the lateral placement of the bolus simulator in the oral cavity. The outer casing or skin 902 may originate from a tubular portion of the preform that forms the bolus simulator, which tubular feature is compressed into a ribbon like shape in a subsequent molding process before the shield and handle components are molded thereover. The core 900 may be an extension of the handle and shield formed during the overmolding process. Referring to FIGS. 113, 149 and 150, the overmold interface 111 between the tether 10 and the shield is shown, which minimizes the presence of crevices or gaps between the two components that may harbor contaminants. This type of smooth transition may alternatively be achieved by way of mechanical bonding including for example gluing, welding and heat staking.

Referring to FIGS. 149 and 156, the casing or skin 902 is formed with enlarged side portions 912, cylindrically shaped in one embodiment, and which surround opposite side edges 914 of the core. The casing or skin also includes comprises middle portions 916 extending between the enlarged side portions 912 on opposite faces of the core. The middles portions, in combination with the core, define a first thickness H1 that is less than a second thickness H2 of the enlarged side portions, in combination with the core 900. The enlarged side portions 912 provide a tear retardation feature. As such, if a tear were inadvertently made in the tether, whether by biting or otherwise, the propagation thereof is slowed down by the enlarged side portions. In particular, at the transition between the middle portion and enlarged side portion, the stress magnitude and direction is changed due to the change in geometry, with a large portion of the stresses taken up by the enlarged portion, otherwise referred to as a reinforcement feature, leaving the middle portion with less longitudinal stress that slows down any tear extending laterally across the tether. In addition, the enlarged side portions 912 compress the middle portion 916 when tension is applied, thereby further reducing the ability of the tear to propagate laterally.

The tether may be flavored or scented by way of material impregnation, or by mechanical bonding through dipping or coating. Portions of the tether may flavored or scented, or the tether may be free of any such agents.

In one embodiment, shown in FIGS. 107 and 109, the tether may include a pair of spaced apart side portions 312 that define a space or opening 314 therebetween. The opening 314 allows for at least a portion of the user's tongue to be received therein, and for the tongue to touch the hard palate of the user's mouth to further facilitate swallowing. The side portions 312 may be configured as fluid conduits. As shown in the embodiment of FIG. 109, a right tether portion enters the user's mouth at the right angle of the user's lips, while the left tether portion enters the user's mouth at the left angle of the user's lips, which ensures that no material of the tether is disposed between the upper and lower lips at and near the sagittal midline where somatic sensitivity is greatest. Accordingly, the user experiences natural sensory feedback from the lips contacting each other during use. Similarly, no material is disposed between the maxillary and mandibular teeth anteriorly at and near the sagittal midline, and no material is disposed between the tongue tip/blade and the roof of the mouth (i.e., alveolar ridge posterior to the maxillary incisors). Therefore, the user may maintain a natural tongue/aveolar ridge relationship during use with the associated advantage that the user receives natural somatic sensory feedback from the oral cavity. In addition, the user may more easily use their tongue and lips in oral functions, such as during speaking, drinking and eating. It should be understood that one of the side portions may be eliminated altogether, with the tether being formed from a single, asymmetric side portion, whether left or right. This may be particularly well suited for users with unilateral oral impairment, such as patients with lateral oral resections for oral cancer, or unilateral oral paresis following stroke or other neurological condition.

The tether may be made of a single material, or a composite of materials such that it satisfies applicable pull and durability tests, including but not limited to EN13450 and EN1400. Included in the pull and durability test requirements are the connection between the tether and the bolus simulator and the shield/handle. A single material design may include silicone (durometer Shore A 40 or higher), phthalate and lead free flexible PVC or EVA (durometer Shore A4 or higher). A composite material design may include reinforcing elements with a polymeric or silicone binder matrix. Various reinforcements may include woven fabrics, such as a KEVLAR material available from Du Pont, and/or tougher polymeric and silicone materials with higher durometer values than the binder. The binder material may be, but is not necessarily, the same as the overmolded layer of the shield or the casing of the malleable bolus simulator.

As shown in FIGS. 23-33, a tether 10 extends between the extraoral user interface 4 and the bolus simulator 12, and which retains the structural integrity between those components. The tether may also be configured to communicate any external dynamic input to the bolus simulator from the operator, e.g., manipulation of the handle. In one embodiment, the tether may be configured as a thin, flat piece of material that does not substantially interfere with a closing of the user's mouth or jaws, or otherwise hinder the acts of swallowing, mastication, or chewing. In one embodiment, shown in FIGS. 53, 62, 63 and 65-67, the tether has an opening 50 extending through an end thereof. The tether is inserted through a slot 52, 203 in the shield, formed in one embodiment as a cover, and into a slot 54 formed in the end of the handle. The opening 50 is engaged on a catch member to secure the tether to the handle as shown in FIG. 87.

Referring to FIGS. 15, 16, 18, 24, 25, 26A and B, 27 and 28, the tether 62 is configured as a gas passageway communicating with the handle conduits 56. As shown in FIGS. 25, 60 and 61, a continuous tube, or tubes, may function as both the gas conduit 56, extending through the handle, and as the tether 62. As shown in FIG. 18, a one-way fluid intake valve 64 is disposed between the handle conduits 56 and the tether conduits 62 to permit one-way flow passage of fluid to the tether conduits. As noted, the tether 10 may be configured with one or two conduits that extending from the handle to the intraoral bolus simulator. The conduits 62 may be configured as tubes, which serve alone as the tether, or may be incorporated into an integral system, passing through or formed in a separately molded tether. A fluid, such as a gas, may be passed through fluid passageways 66 formed interiorly of the bolus simulator, and then out through exit ports 68 forming an outlet, wherein the fluid, such as gas pulses, may be directed at various locations of the user's mouth. Again, the passageway or conduit 66 formed in the bolus simulator may simply be configured as an end portion of a continuous tube that also makes up the tether conduit 62 and handle conduit 56 as shown in FIGS. 60 and 61.

As shown in FIGS. 28, 30, 31, 64 and 74, the tether 10 may also include or contain one or more fluid conduits 70 extending between an interior volume 72 of the intraoral bolus simulator and a reservoir 74. The fluid conduits 70 may be positioned next to, or spaced on opposite sides of, the gas conduit 66, but are segregated therefrom. In one embodiment, the reservoir 74 is positioned in the handle 6, for example in an opening 403 formed in the handle as shown in 64, on an opposite side of the shield 14 from the bolus simulator 12, such that the reservoir 74 is extraoral. In one embodiment, the sides of the reservoir are exposed to the user for actuation and manipulation. The reservoir 74 and conduits 70 may be separately formed and installed in the handle through the shield as shown in FIG. 64. The fluid conduits communicate with an interior volume of a bolus simulator via an inlet and outlet 83, 85, which may be the same opening. Alternatively, separate conduits may be provided to communicate from an inlet to the interior volume, and from an outlet to the reservoir. The reservoir 74 may also be provided as a component separate from the handle.

The tether 10 is flexible enough to allow for easy manipulation of the position of the bolus simulator 12 within the oral cavity, but strong enough to withstand chewing, biting, pulling etc., so as to prevent separation of the bolus simulator from the tether, and ultimately the handle or other user interface.

Referring to the embodiment of FIGS. 44 and 45, a tether 10 is coupled to the yoke 136 and extends longitudinally therefrom.

Bolus Simulator

Referring to FIGS. 23-25, 31, 33-43, 60-67, and 149-152 the intraoral bolus simulator 12 may be configured in a number of different variations. In various embodiments, the intraoral bolus simulator is configured with a solid core 80, a fluid (gas or liquid) filled core 82 or bulb, whether or a constant or variable volume, or combinations thereof. In various embodiments, the gas may be air, oxygen, nitrogen, or other suitable and non-toxic gases. The fluid may be water or saline solution, and may include solid particles to provide additional texture. The core may be configured with a polymer, foam, fluid, foam gel, gel or combinations thereof in a polymeric pouch, which may present a tough but pliable characteristic.

In one embodiment, the bolus simulator has a solid inner core 80 and an outer coating 84. The outer coating may contain, or be impregnated with, a chemical agent, such as menthol, that gives rise to a cool percept when coming into contact with the oral mucosa. The outer coating may also include an oral antiseptic that may provide improved hygiene, which may help avoid aspiration pneumonia. The outer coating may also contain, or be impregnated with an oral medication. In one embodiment, the solid core 80 is made of flavored or non-flavored polymers, and is covered with a protective jacket 84 made of PVC (lead and Pthhalate free), EVA or PolyFlav+EVA. In one embodiment, the bolus simulator has a length of about 2.0±0.5 cm, a width at a distal end of about 2.0±0.5 cm, a width at a proximal end of about 1.5±0.5 cm and a heath of about 1.0±0.5 cm.

In one embodiment, referring to FIG. 97, the bolus simulator 12 is configured with a sensory stimulation region 92 and a bolus region 90, which extends about 0.5 cm wide along the length of a top and bottom of the simulator. This region may release a bolus, such as water, from the inner core into the oral cavity when pressure is applied by the user's tongue as the tongue moves toward the palatal contour. The remainder of the bolus simulator forms the sensory stimulation region 92, including the lateral and distal portions of the simulator, which are the regions that may contact various taste receptors for sour and bitter taste stimuli. The sensory stimulation region 92 may be covered with a base layer of water insoluble material, or an outer coating, that provides a means of separating the inner core, which may include a bolus such as water, from a gustatory agent that may be included in an outer coating. In one embodiment, the sensory stimulation region includes the outer coating, while the bolus region is configured only with an inner core. The outer coating may include a carrier, or jacket, housing the stimulating agent. When contacted by saliva-covered mucosa of the tongue and palate, the carrier releases the stimulating agent into the oral cavity and oropharynx. Of course, the outer coating may be configured such that it does not leach into the oral cavity of the user, which may be important when in use by dysphagia individuals vulnerable to tracheal aspiration of oral secretions.

Various gustatory stimuli may be suitable for use with the device. The outer coating, or the inner core, may be coated or impregnated with a number of chemicals known to stimulate, facilitate or evoke swallowing by means of stimulating saliva, or by way of exciting gustatory sensory endings that impinge on the brainstem or cortical swallowing networks, or by exciting other sensory nerves that are involved in the triggering of swallowing. Various gustatory agents may include without limitation NaCl, sucrose, quinine or other bitter agents, or sour agents such as lemon juice. Flavouring agents may be mixed into a silicone material or by way of coating/dipping. The flavouring agents may be scent, taste or combinations thereof.

In one embodiment, the inner core 80 is made of an absorbent, deformable material, including for example foam. The inner core may be include a bolus to be swallowed, such as water, which is released into the oral cavity and oropharnyx when the user applies pressure to the inner core by moving the superior tongue surface toward the palate as occurs during the act of swallowing. For example, in one embodiment, a fluid, for example a liquid, of 1 to 3 ml, is released from the inner core by pressure applied by the approximation of the tongue and palate. The inner core may be remotely assembled with a fluid, or it may be filled at the point of use, for example by dipping the core into a fluid such that the inner core may absorb or be filled with the fluid.

In some embodiments, the inner core 82 is formed as a closed volume or hydrostat, such that the fluid contained therein may not escape during use such that it cannot be swallowed or aspirated. If the fluid is a liquid, the properties of the liquid, including the viscosity, may be varied to simulate a variety of bolus types, including without limitation a thin liquid, a thick liquid, a honey thick liquid, a puree, a fine chopped mixture, etc. The malleable core, such as a liquid or gel, may be encased in a durable but flexible skin or pouch. The fluid filled bolus simulator 82 allows the user to manipulate the bolus simulator shape much like a masticated piece of real food, and provides an organic feel, which may aid in inducing swallowing and be manipulated to simulate swallowing. The flexible tether 10, with a minimum thickness, further provides for maximum maneuverability of the bolus simulator. In this embodiment, the bolus simulator 82 and a reservoir 74 communicating therewith may form a closed volume, but with the fluid being transferred back and forth between an inlet/outlet to the interior volume of the bolus simulator. The pouch may be made of silicone, EVA, phthalate free flexible PVC with durometer values ranging from 30 Shore A to 80 Shore A. The core may be composed of saline, edible and nonperishable oil, silicone gels such as SILPURAN and ELASTOSIL series gels available from Wacker, and/or propylene glycol. If both the pouch and core are made of silicone, it may be possible to vulcanize both materials together. The bolus simulator should meet the same strength and durability requirements as outlined for the tether, with additional burst resistance requirements if made from any of the materials other than the vulcanized silicone.

As shown in FIGS. 89-91, 149, 151, 152, 157 and 158, the bolus simulator 82 is configured with a sealed volume of air, gel, liquid, silicone or foam, with the outer skin configured in one embodiment with a flavoring.

Referring to FIGS. 33-41 and 47, the bolus simulator 80 may be configured as a solid piece of flavor impregnated polymer. Alternatively, as explained above, a flavored core may be encapsulated in a porous, flexible and tough polymer jacket 84. The bolus simulator may assume any number of shapes, including a donut shape, a lollypop shape (e.g., circular, oval, triangular, elliptical, and so on), combinations thereof, or other suitable shapes. As shown in FIG. 152, the bolus simulator 82 has a greater thickness at a distal end 918 than a proximal end 923 connected to the tether. When the bolus simulator is covered with a coating or jacket 84, the outer coating may function as an initial flavor burst once placed in the oral cavity, with a flavor impregnated core 80 providing a longer lasting flavor stimulation that is less intense in nature than the initial burst. As shown in FIGS. 36-38, 65, 67 and 77-79, the outermost surface 96 of the bolus simulator maybe provided with a plurality of bumps, ridges, depressions, knurls, etc., or combinations thereof, so as to provide a textured surface that stimulates the production of saliva upon mastication. As shown in FIGS. 81 and 82, the bolus simulator 80 may be solid, but have a gas passageway 66, or a pair thereof, extending therethrough and communicating with an outlet 68.

In one embodiment, and referring to FIGS. 106-107 and 110-117, a flexible silicone pouch 84 encases a vulcanized silicone gel core 80, which is cured into a specific form such that it is not free flowing like a liquid in the pouch. This provides the advantage of avoiding a loss of material in the event of a breach to the pouch. In addition, the gel core maintains a structural integrity of the bolus simulator. At the same time, the cured shape of the core allows the pouch to flex without substantial stretching. The pouch may be made from a flexible but non-stretchable material, such as flexible PVC, or from stretchable rubber with lower tensile strengths. The bolus simulator may include indentations 87 on one or both inferior and superior surfaces thereof. The indentations may be spherical, or otherwise shaped. The indentions may not be symmetrical, with a superior side shaped and contoured to mate with and fit against the roof of the user's mouth, while the inferior side is shaped and contoured to mate with the tongue. In other embodiments, the surfaces may be contoured differently to maximize the malleability of the bolus simulator.

In the various embodiments, the pouch 84, or jacket, e.g. silicone, may be permeable so as to allow the transfer of flavor from a flavored core to the outer surface of the pouch. Alternatively, the core may be dipped in a flavored solution, with the permeability of the pouch or jacket allowing the flavor to migrate into and remain within the pouch or the core, which may also retain the flavor from the agent. During use, the flavor is slowly released onto the outer surface of the pouch or jacket.

In one embodiment, shown in FIGS. 15, 18, 43, 54, 83-85, and 98-100, the bolus simulator has a gas filled bladder 98 with an interior volume that ejects a volume of gas in response to a proper manipulation by the user to provide a sensory stimulation of sensory fields in the back of the pharynx. In one embodiment, the gas is air. Referring to FIGS. 99A-G, the oral device includes a bolus simulator 98 and an extraoral user interface 204, configured as a short handle that may be grasped by the user. A curved shield 214 is coupled to the handle. A pair of air intake conduits 208, configured as silicone tubes in one embodiment, extend longitudinally from the shield. A one-way intake valving mechanism 210 and conduit 216 communicates between the air intake conduits 208 and the bolus simulator 98. A one-way, pressure-relief exhaust valve 228 communicates with the bolus simulator, releasing the fluid when a sufficient internal pressure is realized in the interior volume of the bolus simulator. The interior volume of the bolus simulator has an inlet and an outlet, which are spaced apart in this embodiment, and with the valving mechanism and conduits acting as a pump.

Figure 70:
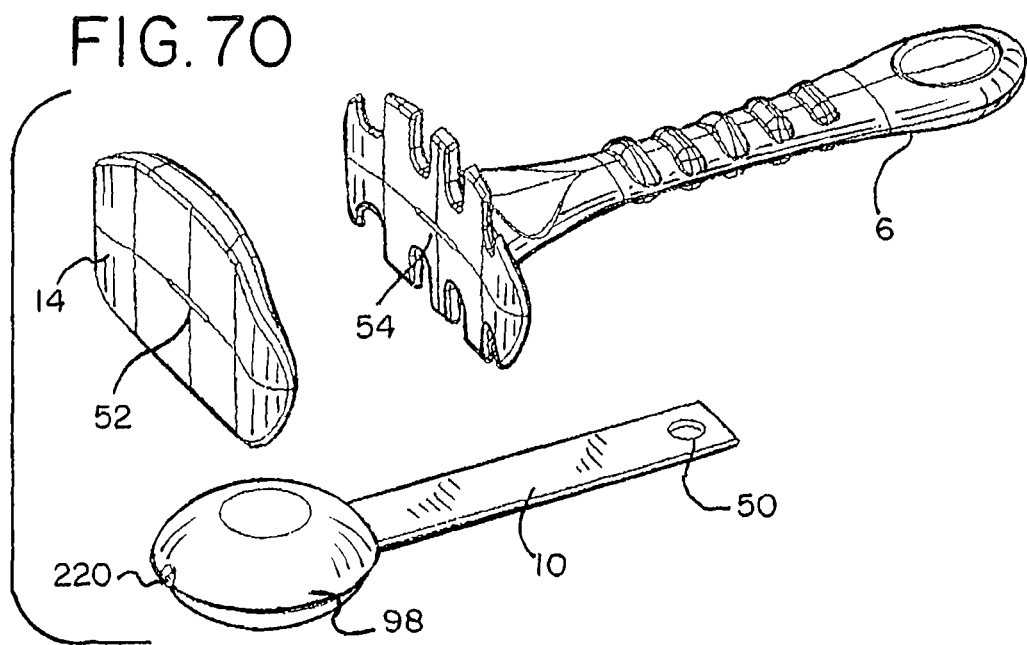
FIG. 70 is an exploded view of an alternative embodiment of an oral device.
Figure 98A:
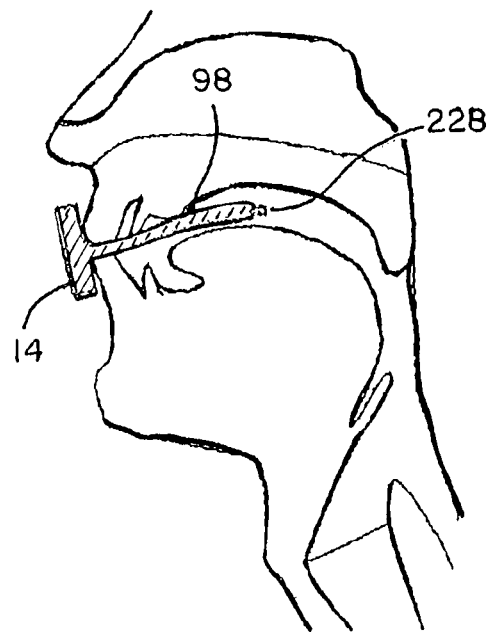
FIGS. 98A-D show the steps of inflating and deflating a bolus simulator.
Figure 98B:
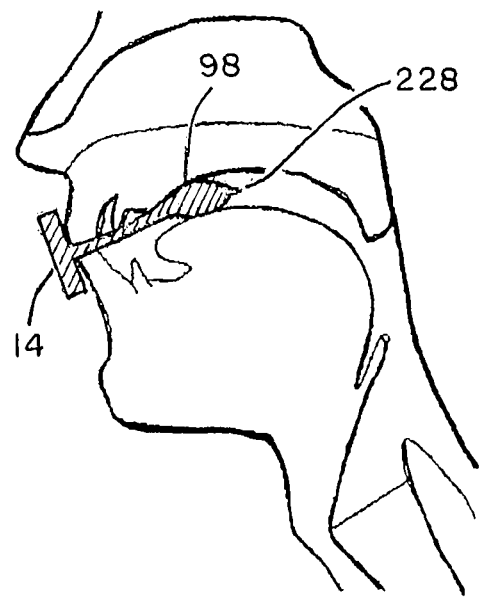
Figure 98C:
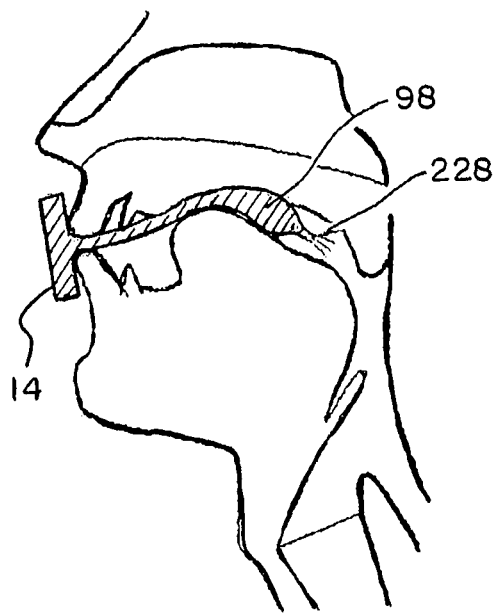
Figure 98D:
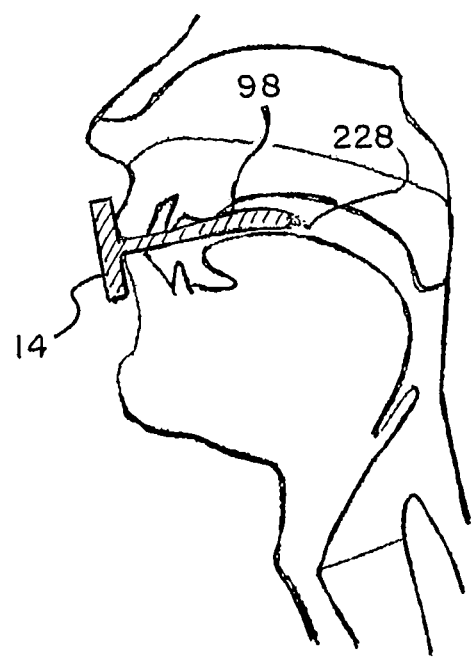
Figure 99A:
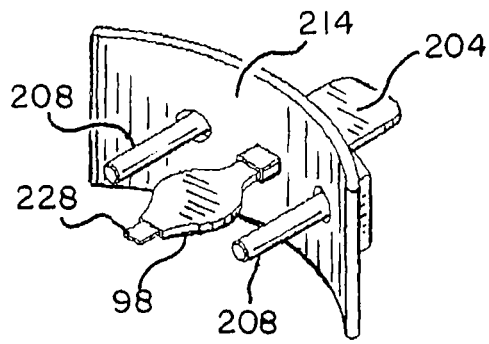
FIGS. 99A-G show various views of an oral device.
Figure 99B:
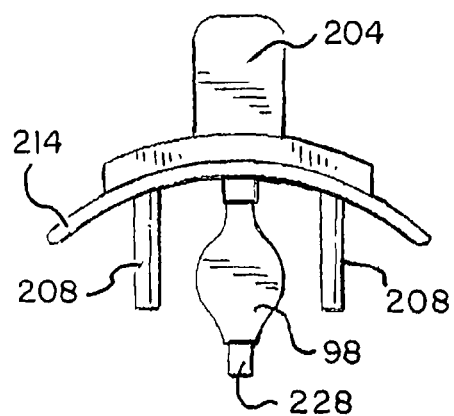
Figure 99C:
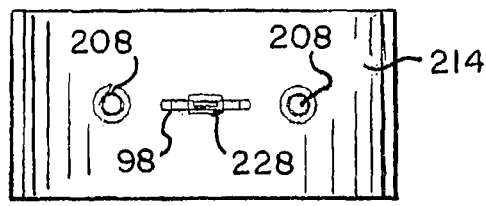
Figure 99D:
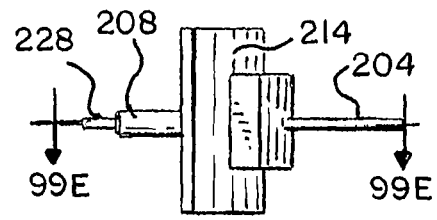
Figure 99F:
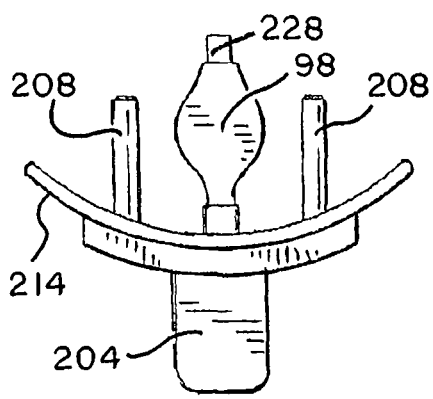
Figure 99E:
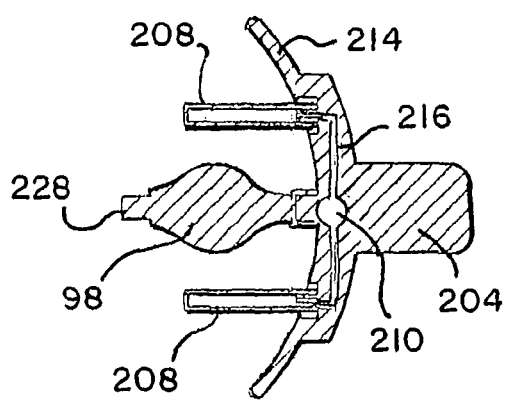
Figure 99G:
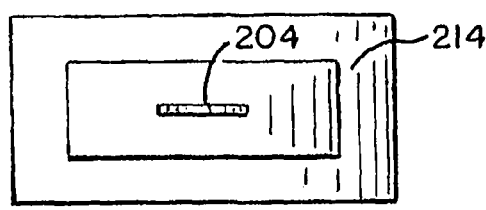
Figure 101:
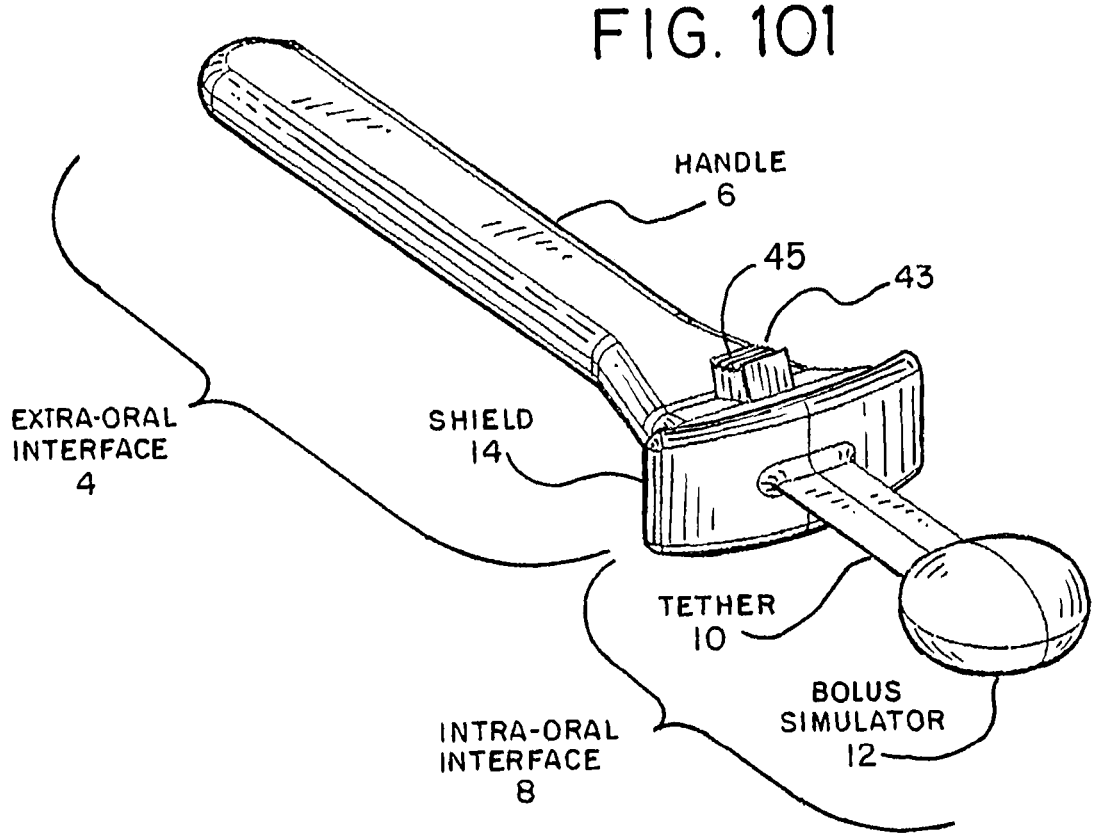
FIG. 101 is a perspective view of an alternative embodiment of an oral device.

Alternatively, as shown in FIGS. 42, 43 and 70, the bolus simulator 98 may be filled and evacuated through the same port 220, configured with a two-way valve 222. The interior volume 230 is inflated by way of a sucking action through the valve 222. When a predetermined pressure is reached, the valve 222 then releases the air from the bolus simulator. In this embodiment, the port 222 defines both the inlet and outlet to the interior volume, which may change from at least a first to a second volume in response to first and second amounts of fluid being received therein. In addition, the simulator, in combination with the valve 222 acts as a pump to fill the interior volume.

The bolus simulator 98 may be filled with a reticulated foam or sponge element to facilitate self-inflation. The sponge element may be impregnated with a flavoring that may be activated and released, or the outer casing of the bolus simulator may be coated or impregnated with a flavoring. The walls of the bolus simulator bladder 98 may have a variable thickness so as to alter the rigidity and control the shape changes of the bladder in operation. In addition, the bladder may be molded with different materials, in different layers and/or regions, to provide unique regional properties. For example and without limitation, the bladder may be made of a soft durometer rubber and co-molded or overmolded with a shield and handle.

In the embodiment shown in FIGS. 100 A-F, a bolus simulator is provided with a one-way exhaust valve. In this embodiment, a handle 258, configured with a thumb-hole 260 for gripping by the user or care giver, is coupled to a shield 262 opposite the bolus simulator. The handle includes an internal gas intake passageway 264 and a one-way intake valve 266. A nipple 268, or other coupling member, extends from the handle. A conduit 270, or tube, is coupled to the nipple, with a squeeze bulb connected to the conduit. The flow volume and pressure from the squeeze bulb may be controlled by a regulator 276. A clamp 274 may be coupled to the conduit to close the conduit. It should be understood that other fluid supply devices, such as an oxygen supply, may be coupled to the nipple.

Referring to FIGS. 15, 18, 69 and 83-85, the bolus simulator 98 is self-inflated from an external air source, such as the ambient environment, through the fluid passageways 56, 62 defining an inlet to the interior volume of the bolus simulator. The fluid, such as air, is released through a pair of duckbill valves 88 communicating the exit ports 68, defining an outlet to the interior volume of the bolus simulator. In this embodiment, the inlet and outlet to the interior volume, which may change from a first to a second volume in response to first and second amounts of fluid being received therein, are spaced apart and separate. As shown in FIGS. 82-85, the intraoral portion may be separately formed with a shield cover that fits over the support structure formed on the end of the handle, with the fluid passageways lining up upon assembly.

Referring to FIG. 92, one embodiment of an oral device includes a bolus simulator 148 with a "bite" sensor 152 or tongue press sensor, which may be configured as a piezo device or as a resistive/capacitive sensor, either of which provides an output relative to an input force applied thereto. Electrodes 150 are disposed along opposites sides of the bolus simulator such that the electrodes are capable of contacting the side of the user's cheek and/or tongue. The electrodes are operably coupled to the sensor 152. The bolus simulator may also be configured with various textures, flavoring, scent, shapes, malleability, etc. as otherwise herein described. The device may also be configured with a shield 14 and a handle 6.

In another embodiment, shown in FIGS. 27-32B, a fluid reservoir 74 is provided in the extraoral portion, for example as an expandable reservoir in the handle on an opposite side of the shield. The reservoir 74 provides a mechanism for adjusting the softness of the bolus simulator 82. For example, the user may manipulate the reservoir, which may have a flexible user interface. A fluid passageway 70 communicates between a bolus interior volume and the reservoir. The fluid may be formed of a gas, liquid, or combination thereof. The interior volume may be altered from a first volume to a second volume having respective first and second amounts of fluid through the inlet and outlet to the bolus simulator, which are one and the same in this embodiment.

Referring to the embodiment of FIGS. 44 and 45, the bolus simulator 80, 82 is connected to the tether 10 and is disposed between the intraoral gas conduits 112.

It should be understood that the various embodiments of bolus simulators may be incorporated into the various embodiments of oral devices. For example and without limitation, the various bolus simulators disclosed herein, including the bolus simulator shown in FIG. 92, may be incorporated into the oral device shown in FIGS. 44 and 45.

Referring to FIG. 94, a pair of exhaust conduits 192 extend laterally from the bolus 98 and direct a fluid to opposite sides of the mouth. Valves 88 are located at the distal ends of the conduits 192. The bolus simulator 98 is connected to a tether.

Referring to FIGS. 118-128B, the bolus simulator 500 is provided with a reinforcement member 502. The reinforcement member 502 reinforces the bolus stimulator so as to help prevent it from releasing particulates or suffer other damage, while maintaining soft and flexible properties. In one embodiment, the bolus simulator has a components made of elastomers and thermoplastics.

In one embodiment, the edges of the device are protected, since such edges may be experience localized concentrated biting with full force. As shown in FIGS. 118-120, and 157 a reinforcement member may be formed as a ring 502, which extends around the periphery of the bolus simulator. The reinforcement member may be co-molded and/or mechanically attached to a softer portion of the bolus simulator, including the jacket 504 filled for example with a gel 506. As shown in FIG. 157, the bulb portion 82, or air filled pouch, comprises a peripheral side wall 922 disposed between and connecting opposite faces of the bulb 924. A shoulder 926 may be formed at the junction between the side wall 922 and faces 924, with the faces thereby being recessed relative to the side wall. The peripheral side wall 922 includes an annular reinforcing rib 928 extending around the peripheral side wall. The rib 928 may be formed interiorly (as shown in FIG. 15), or exteriorly, and may be defined in one embodiment by the side wall being thicker than the faces. The reinforcing rib 928 functions as a tear retardation feature, which enhances the strength of the bulb without comprising the knead-ability of the air filled bulb.

Figure 121:
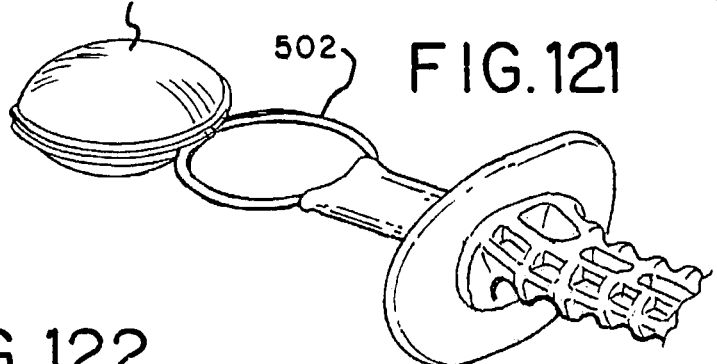
Figure 122:
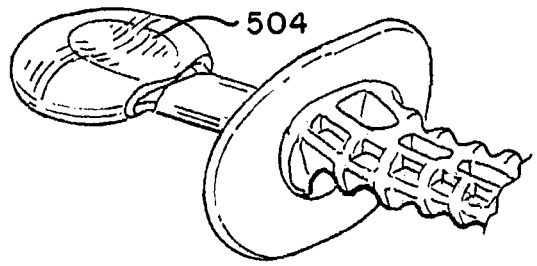
Figure 123:
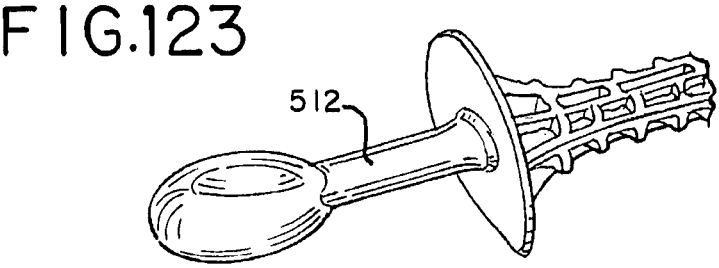

The reinforcement member may be made of the same family of material as the softer portion or other more rigid materials material. For example, various elastomer and/or thermoplastics may be used for the reinforcement member and the softer portion. The reinforcement member may also be made of various hard plastics or metal. The edge of the bolus simulator may be provided with smooth rounded sides or wide sides with steep slopes to impede the ability of the use to grab the reinforcement member with their teeth 508. The reinforcement member also is resistant to any tearing forces applied by the user to the bolus simulator. As shown in FIGS. 121-123, an inside-out bolus jacket 504 is overmolded on the ring 502, and this is inverted to cover the ring, with a second cover 512 is then molded over the tether and the end of the bolus jacket to seal the jacket.

Figure 124:
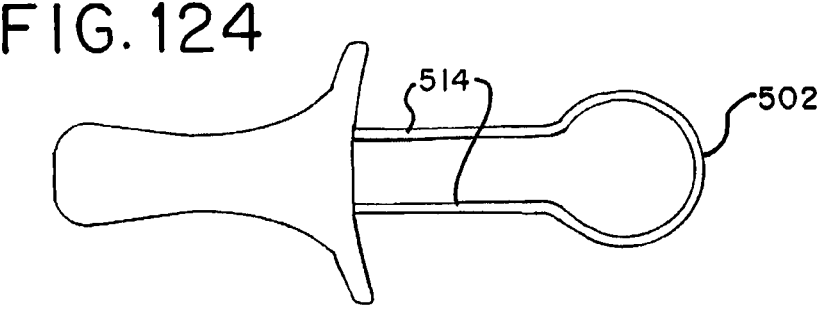
Figure 125:
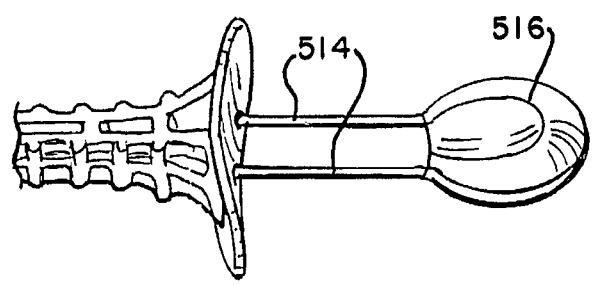
Figure 126:
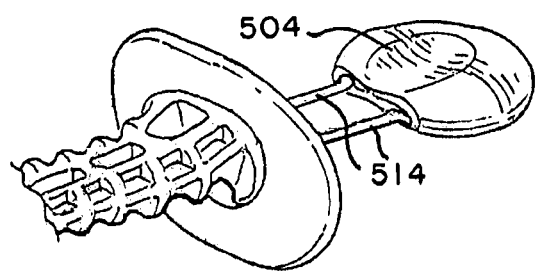

Referring to FIGS. 124-126, the ring may include a pair of legs 514 that form part of tether. A core 516 may be inserted in the ring, with a bolus jacket 504 molded over the ring and/or core. Referring to FIGS. 127A-C, the ends of the legs 514 may be configured with an interlock feature, such as an enlarged insert portion, which is received in a corresponding socket 520 in the extraoral handle, for example by mechanical attachment or snap-fit. A cover 522 may then be molded over one or more of the legs and handle to further define the tether and handle.

Referring to FIG. 128, the reinforcement member is configured as sheet, formed for example from a thermoplastic material, which is positioned as a septum 524 extending along the middle of the bolus. Referring to FIG. 129, the reinforcement member is configured as a thermoplastic mesh 526, which is over molded with a bolus and/or tether jacket.

Figure 130:
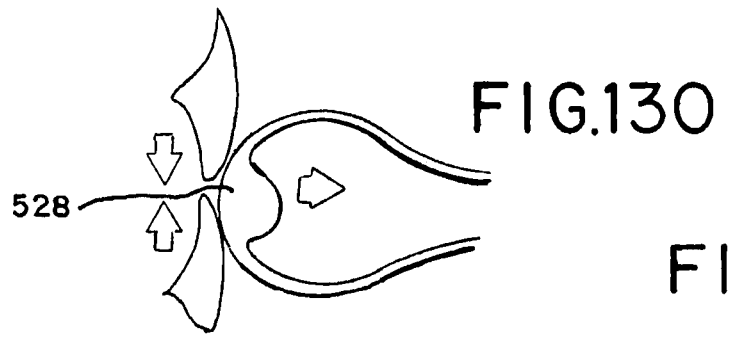

Referring to FIGS. 130-133 and 136, various embodiments are shown wherein the reinforcement member is integrally formed with the bolus simulator, preferably from the same material. In these embodiments, the geometry, shape and/or relative thicknesses help define a reinforcement member. For example, as shown in FIG. 130, the perimeter 528 of the bolus simulator may be made thicker, with the thickened portion forming a reinforcement member. In another embodiment, the entire jacket may be thickened.

Figure 131B:
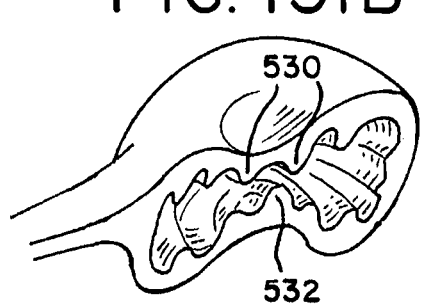
Figure 131A:
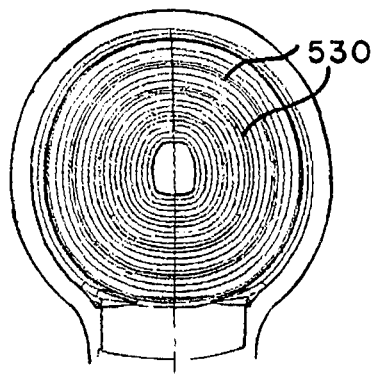
Figure 131C:
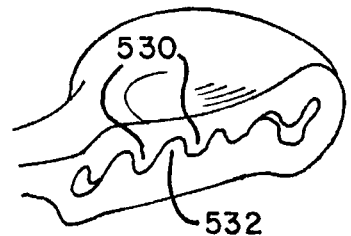

Alternatively, and referring to FIGS. 131A-C, annular rings 530, 532 having different radii are formed on one or both of the opposite interior surfaces of the bolus simulator. In one embodiment, the rings 530 on one surface are offset or staggered relative to the rings 532 on the other surface, such that the rings acting in unison mesh or nest, and reinforce the bolus simulator when compressed. The edge portion may still be reinforced, whether with a separate member or integrally.

Figure 132B:
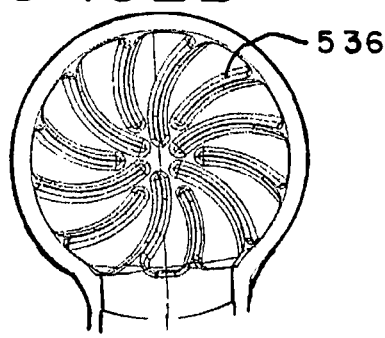
Figure 132A:
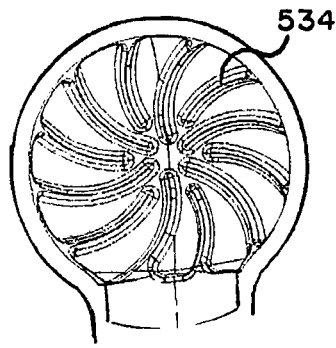
Figure 132C:
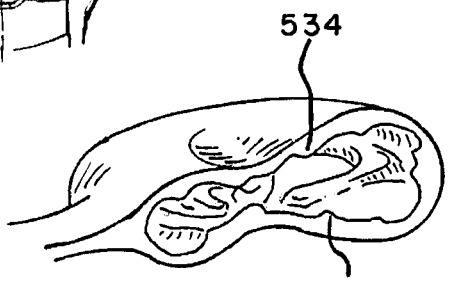

Referring to FIG. 132A-C, one or both of the interior surfaces has rifling rings 534, 536 that extend radially outwardly from the center of the bolus to the edge portion. The edge portion may still be reinforced, whether with a separate member or integrally. The rifling ribs on the two surfaces may be oriented in opposite directions so as to avoid pinching of the bolus jacket.

Figure 133A:
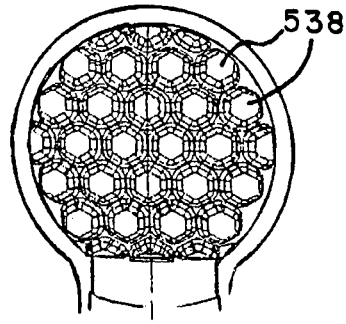
Figure 133B:
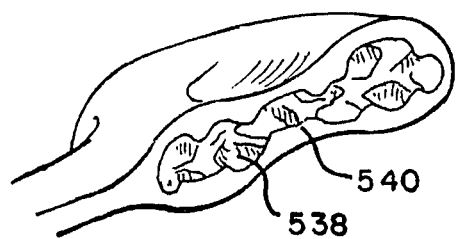

Referring to FIGS. 133A and B, one or both of the interior surfaces may be configured with a honeycomb pattern of recesses 538 and ribs 540, again with the patterns on opposing surfaces being offset in one embodiment. In this idea the bolus jacket is made to be thicker to better withstand chewing.

Figure 136A:
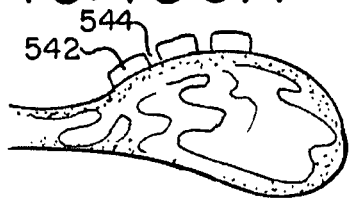
Figure 136B:
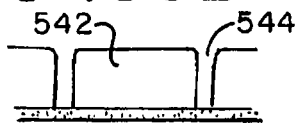
Figure 136C:
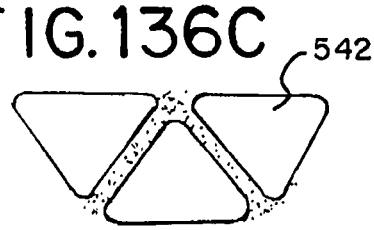

Referring to FIGS. 136A-C, the outer surface of the bolus simulator jacket is provided with tiles 542, which may be the same or different material as the jacket. The patterned tiles allow the bolus simulator to flex but the tiles protect the bolus from puncture. The tiles may have various geometrical shapes, including triangular, rectangular, polygonal, round, oval, elliptical, obround and any other suitable shape. The shape of the tiles, and the spacing or gaps 544 between the tiles 542, ensures that they do not restrict the flexibility of the bolus.

Figure 134:
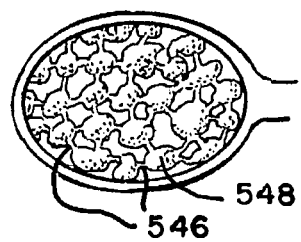
Figure 135:
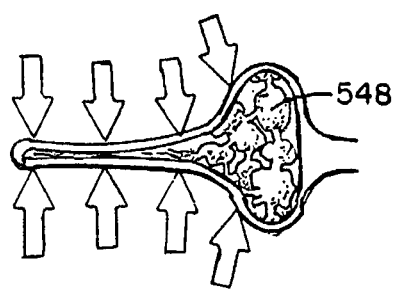

Referring to FIGS. 134 and 135, the bolus may be made out of encapsulated foam with air pockets 548 that are connected via connectors 546. When the bolus is partially compressed the filler in the bubbles, which could be gas, liquid, viscoelastic or solid, in the compressed region migrates to the bubbles that are free of compression through the connectors.

Figure 137:
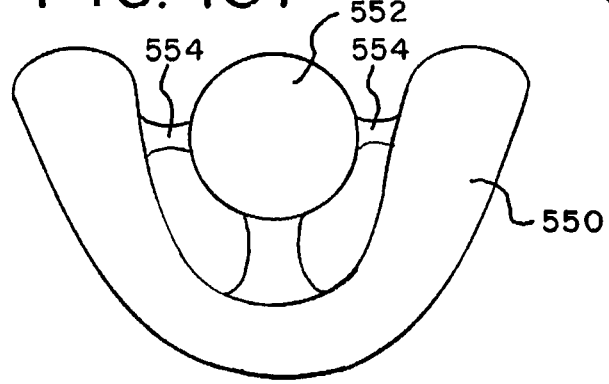

Referring to FIG. 137, one embodiment of an oral device does not have an extraoral portion, but rather includes a mouthpiece or mouthguard 550 that is shaped to fit between the occlusal surfaces of the user's teeth. One or more tethers 554 extend from the mouthguard and are connected to a bolus simulator 552.

It should be understood that it may be desirable to provide the oral device with a limited use or end of life feature, which provide indicia to the user that the device should be discarded and replaced. Such a feature will promote the safe use of the device, both from a hygienic standpoint and material fatigue standpoint. Various types of features may be utilized, including a system based on the user or patient senses, or a system based on the diminishing of the use's satisfaction over time, or some combination thereof. A diminishing satisfaction feature and method may include a transition from pleasant to neutral, or from pleasant to non-pleasant.

In a pleasant to neutral system, the device will give the user added positive feature(s) that will diminish over time into something neutral. As disclosed herein, Polyflav may be molded into the bolus simulator. Likewise, flavourant coating may be added to introduce scent and taste. A hydrophilic coating may also be used. The hydrophilic coating may improve lubricity of silicone and TPE, and thereby enhance the feel of the bolus simulator inside the user's mouth. With the coating in place, the tendency of the user to feel that their tongue is exfoliated after using the oral device for an extended period of time may be reduced. In addition, the hydrophilic coating may be loaded with colourants and flavourants. It is possible to temporarily enhance the lubricity of the surface of the bolus simulator using corona and plasma treatment. In the silicone samples exposed to corona treatment, their hydrophobic surface properties were temporarily removed. The window when the hydrophobic surface property is altered may be enough to bond something to the silicone surface that may provide certain added benefit to the product. A similar method of surface treatment is plasma.

Under the pleasant to non-pleasant category, the initially positive feature(s) will diminish over time into something unpleasant. For example, a texture change, or tactile feature, may be achieved through coating. A certain unpleasant texture is put onto the surface of the uncoated device and then it is coated with temporary coating that has pleasant surface finish that wears through as the device is used to eventually reveal the unpleasant texture. In one embodiment, a loaded or unloaded hydrophilic coating may be used. Perceived heat or coolness using menthol or mint oil may also be suitable. In another embodiment, the bolus simulator transitions from a smooth to lumpy configuration as the device is used, providing another tactile feature. Referring to FIGS. 157 and 158-159C, the fluid filled bulb 82 has opposite faces 924, which are recessed and have an outwardly concave shape in one embodiment. First and second lubricated patches 930 are disposed on the recessed opposite faces 924, for example by overmolding, and fills the recess such that they abut the shoulder 926 and may be flush with the side walls 922. In one embodiment, the lubricated patches 930 are made of water soluble thermoplastic particles 932 suspended in a silicone matrix 934. The lubricated patches are transformable in response to an application of a liquid from a first state (FIG. 159A), wherein the particles 932 are suspended in the matrix 934, to a second state, wherein the particles 932 are depleted from the matrix 934 (FIG. 159C). An exterior surface 936 of the lubricated patch is transitionable from a smooth surface in the first state to a rough surface in the second state, due to the voids from the depleted particles 932. For example, as the bolus simulator 12, 82 is put inside the user's oral cavity (see, e.g., FIG. 93), or mouth, the lubricated patches 930 make contact with saliva 938, which causes the water soluble particles to bloom out (FIG. 159B) of the patches and create a slippery feel of a masticated food item. When the water soluble thermo plastic particles 932 are completely depleted, they leave behind empty silicone matrices that have a rough surface (FIG. 159C). The appearance (visual and/or tactile) of the rough surface 936 provides an indication to the user, patient and/or care giver that it is time to replace the device.

In another embodiment, the taste and/or smell may transition from a pleasing to a displeasing smell. The device may have an initial unpleasant taste or scent that is masked by a coating that has a pleasant taste and/or smell that wears off as the device is used. In yet another embodiment, the shape of the bolus simulator may change, signaling the user that the end of life has been achieved. For example, the bolus simulator may be configured with one or more valves and an external reservoir, which allows the bolus simulator to inflate or deflate as the device is use.

In another embodiment, the limit on use is a function of noticeable improvements in the patients. A family of oral devices with different types of features may be used. As a patient's condition improves, the patient moves on to the subsequent grade of oral device.

The device may be provided with a pure indicator, such as a color indicia that changes or disappears then it is time to replace the device.

Limited use features that rely on the patient to determine when the device is not usable may be challenging due to the expected range in cognitive abilities of the target patient group. In this situation, a care giver may have to rely on the patient to communicate how the device feels or tastes. For a caregiver, more obvious indicators may be helpful. Specific indicators like a change in colour may be beneficial. Other more obvious changes in state that are easily detectable by eye would likely work well, such as size variation or tactile variation. For example, a bolus that is flat and not full of air provides a visual indicia of end of life.

Figure 138A:
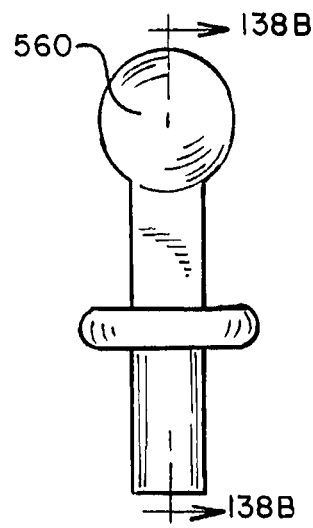
Figure 138B:
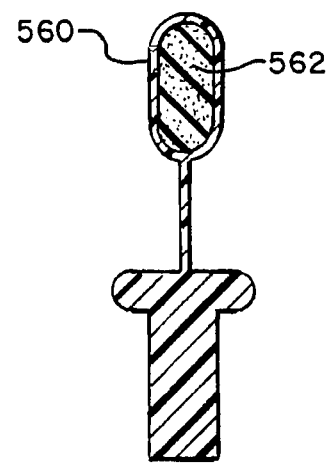

Referring to FIGS. 138A and B, an oral device includes a bolus simulator, a tether, a shield, and a handle. The skin 560 and filler 562 of the bolus simulator, together with the tether, may be made out of hydrophilic material that will absorb liquid and, not only, retain the liquid to be released slowly into patient's mouth during use, but also change their material and/or surface properties because of the liquid within them. The liquid may be a flavourant that provides scent and/or taste sensations. Examples of hydrophilic material that can be used to include, but are not limited to, hydrogels and silicone hydrogels. The bolus simulator and tether may also receive corona or plasma surface treatment to modify their wet-abilities. This change in wettability may also alter the feel of the bolus simulator and tether inside the patient's mouth. The intra-oral portion of the oral device that is covered with hydrophilic coating may be provided with a textured surface, which may both retain the coating better, and provide contrast in the user experience when the hydrophilic coating is dissipated.

The bolus simulator and the tether may also be coated with hydrophilic material to allow it to retain liquid on their surfaces, hence, alter their surface properties. This surface property changes will change the feel of the bolus and the tether inside patient's mouth.

Figure 139:
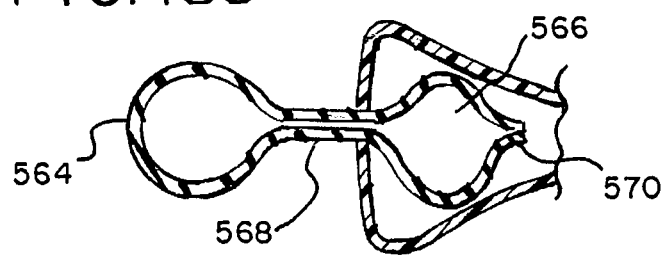

Referring to FIG. 139, an intra-oral bolus simulator includes a bulb 564 filled with air and is connected to an extraoral reservoir 566 via an air passage 568. The extra-oral portion includes a one-way valve 570, configured in one embodiment as a duck bill valve, which communicates with the ambient environment. As the bolus simulator is masticated, the bulb 564 will deflate and pump air into the reservoir 566 through the passageway 568, and stretch or change the shape of the extra-oral portion. When the mastication pressure is released, air will fill the intra-oral bulb 564 again when the extra-oral reservoir 566 relaxes. However, not all of the air may be returned to the intraoral bulb, since a small amount of air escapes through the one-way valve 570. Over time, as the intra-oral bulb is masticated, it will get smaller and smaller, thereby providing indicia as to end of life and simulating a food bolus that breaks down as it is being masticated.

In another embodiment, air leaks out from bolus simulator in a controlled manner in a period of time that allows for a typical use session (20 min to 1 hour). A reservoir would have to be refilled before each use. A valve may be used to control the leakage rate. The valve may be configured as a pin hole. Use could influence the speed at which air leaks out. If user compresses the bolus simulator, the internal pressure may increase causing the air to leak out faster. Air can be delivered to the bolus in a number of different ways, including using a pressurized canister of gas with a metering valve (similar to a Metered Dose Inhaler canister). The canister may have a one-use supply, or multiple supplies. A mechanism could be incorporated into the device that would allow the user to fill the bolus or "prime" the device. The mechanism would advance in one direction or have a counter mechanism that tracks the number of uses and then locks the device once the maximum number of uses has been reached, thus preventing further use.

Figure 140:
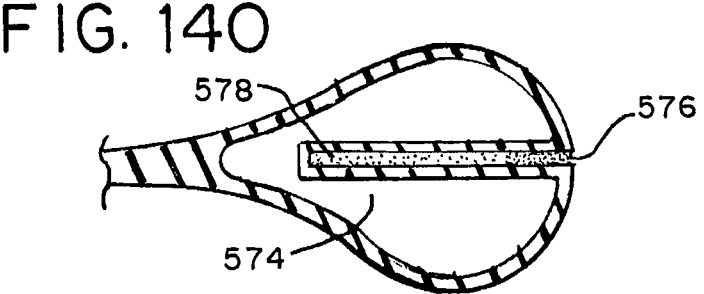

Referring to FIG. 140, in an alternative embodiment, the leak would occur in such a way that it would render the device unusable after a number of days of continued use (e.g. 7 days). The device may be provided with the bolus 574 "pre-filled" with gas. The bolus may be configured with a plug 576 that dissolves slowly with saliva. Chemical action would occur continuously when being used. Once dissolved it would release the air out of the device after which the device would not be usable. The plug could be on tether or anywhere it will be exposed to saliva. In one embodiment, a compartment 578 is provided in the middle of the bolus simulator, with the compartment being filled with hydrogel crystals. The compartment is open to the ambient environment at one side thereof, with an organic polymer plug positioned in the opening. The organic polymer dissolves in liquid. In use, the plug 576 will slowly dissolve in saliva until it disappears completely. After the plug has dissolved, the hydrogel crystals in the compartment 578 will come in contact with saliva and swell to the point that the Swab device is not usable anymore. A one way valve may be included to ensure that the air would leak out and not enter back in.

In an alternative embodiment, a device may include a prefilled canister of gas. When the user received the device it would have to be primed or activated. Activation would release the compressed gas from the canister and allow it to enter the bolus. After this point the canister and bolus would remain an open system. A controlled air leak somewhere in the system would slowly reduce the air pressure till at some point the bolus becomes flat and unusable.

In another embodiment, a gas filled bolus hardens over time, providing a tactile indicator. Two canisters deliver a set volume, with the second canister delivering a much higher volume. After a predetermined number of inflations, the bolus is over inflated making it too large to be used.

In another embodiment, the bolus is filled with silicone that will harden when kneaded. In an alternative, the bolus includes a divider or dividers, with different compartments each filled with one of two parts uncured silicone. When the bolus is manipulated in the mouth cavity the two part silicone mixes and cures.

Figure 141:
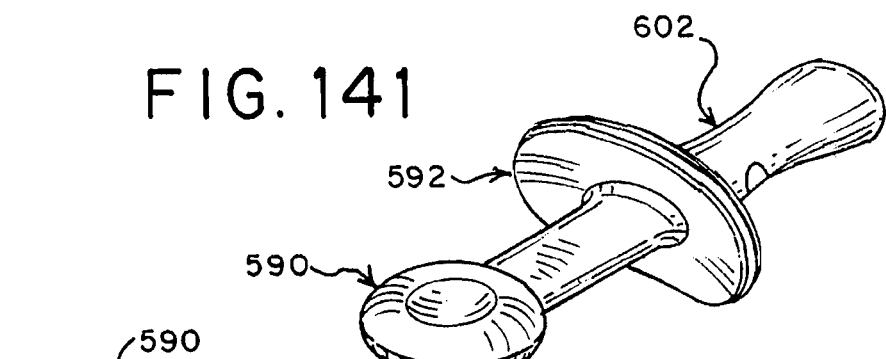
Figure 142:
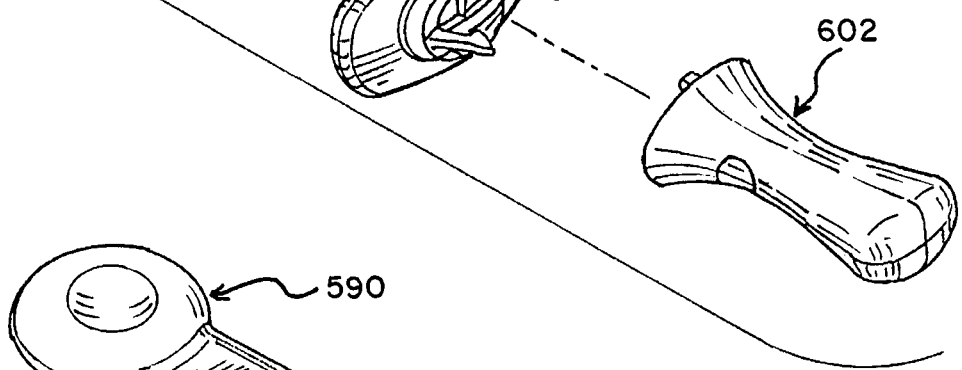
Figure 143:
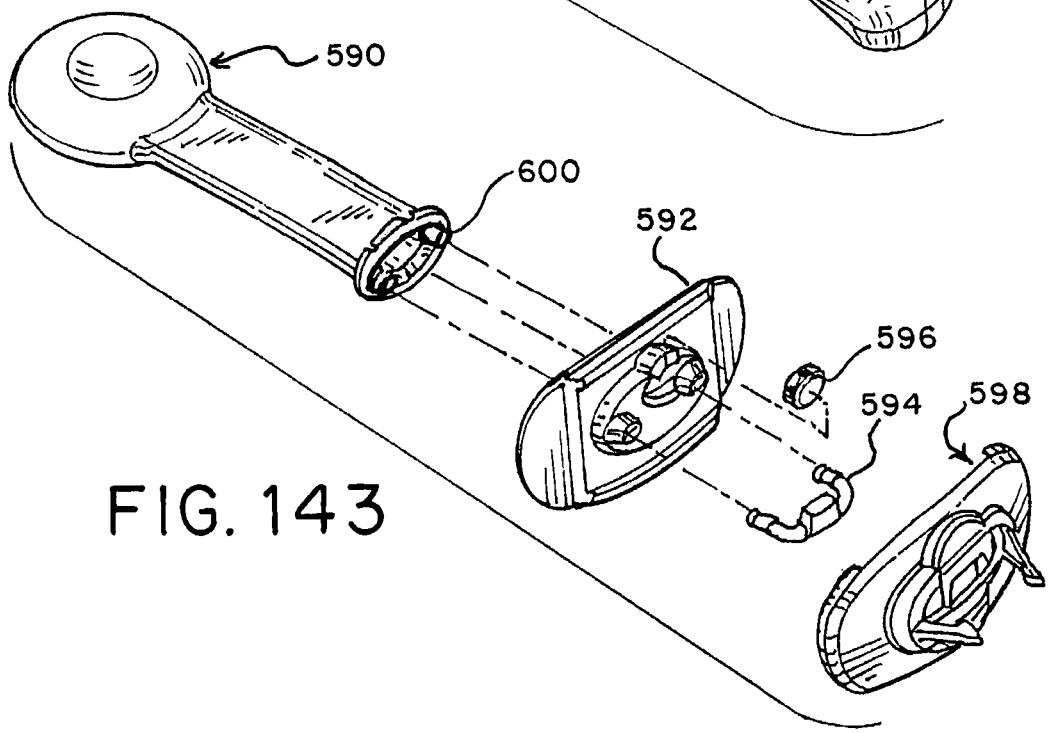

Referring to FIGS. 141-143, an oral device includes a replaceable bolus simulator, tether, and shield. The device includes a bolus jacket 590, a front shield 592, a metal pipe heat conductor 594 a battery 596, a rear shield 598, and liquid filler 600. The handle 602 includes outer shells 604, a latch mechanism 606, a heat sink 608, a thermoelectric element 610, and an electrical contact 612. When the handle is mated to the disposable portion, the latch mechanism retains the connection between the handle and replaceable portion. In addition, during the mating the electrical contacts make contact with the battery in the replaceable portion, thus, the circuit to the thermoelectric element is closed. Depending on the orientation of the handle with respect to the replaceable portion, due to the design of the electrical contacts, the connection causes the thermoelectric element to have hotter or colder bias on its face opposite to the heat sink. In the mated condition, the one face on the thermoelectric element, opposite to the one attached to the heat sink, makes contact with the replaceable portion's metal pipe heat conductor. This, in turn, warms or chills the liquid inside the bolus simulator. Through convection, over a period of time, the liquid inside the replaceable portion will have uniform temperature. The liquid filler can also be made out of material that will evaporate at mouth temperature and liquid at thermoelectric one or vise versa. The former applies to condition where the thermoelectric is in cooling mode. The latter is where the thermoelectric is in warming mode. These conditions can be achieved through either having two separate replaceable portions for warm and cool effects, or having the necessary liquids coexist within the cavity in the replaceable portion. With the former, there would be a need for a poke yoke feature to allow only one orientation. The connection between the liquid filler in the metal pipe heat conductor to the portion of it in the bolus simulator is facilitated via channels. Since the two connectors are identical, shape-wise, and installed in the opposite orientation, to each other with respect to the battery, the handle orientation dictates the thermoelectric temperature bias.

Referring to FIG. 147, and in order to prevent choking in the event that the device gets dislodged in the patient's breathing air path, vent holes 620 may be incorporated into the shield.

In alternative, and referring to FIG. 146, an oral deice 628 includes a bolus filled with H20, Sodium acetate, and configured with an aluminum disc. Clicking the aluminum disc 632 triggers a chain reaction causing the liquid 634 to crystalize and release heat for 30 minutes. The pack is then recharged by boiling it, e.g., in a pot 636, for approximately 5 minutes. Energy is put back to the heat pack and the pack is ready to be reused again for additional cycles.

Materials used to form the handle and shield include silicone materials with durometers around 60 to 80 Shore A, including for example Bluestar's USP Class VI qualified Silbione LSR 4370 is an example. Durometers for TPE options are similar to those of silicone. The bolus filler may be a gas, liquid, viscoelastic material or solid. Liquid contemplated could be saline or TPE oil. viscoelastic materials contemplated could be gels, gelatin, hydrogels, and silicone gels. An example of silicone gel is Wacker AG's Silpuran 2130 A/B.

Carrying Case

Referring to FIGS. 148A-B, 153-155 and 160, various embodiments of an oral device assembly 950, 960, including a carrying case 940, 970, are shown. The carrying cases 940, 970 each include first and second clam shell members 942, 944, 972, 974 hingedly connected along one side thereof with a hinge 946, 976, which may be integrally formed in the two members. The first and second clam shell members are pivotal relative to each other between an open position (FIG. 148B, 154B) and a closed position (FIG. 148A, 154A). The first and second clam shell members define an interior cavity 948, 978 when in the closed position.

The clam shell members include various interior support members, also functioning as positioning members. For example, in the embodiment of FIGS. 153 and 160, the first clam shell member 972 includes a first support 982, or protuberance extending into the cavity, that engages the tether 10, a second support 982, or landing, that engages a bottom surface of the handle 6, and a third support 984, or landing, that engages an edge of the shield 14. In addition, a wall 986 engages a front of the shield 14, while a second wall 988 engages an end of the handle 6, to locate the oral device longitudinally in the case 970.

The second clam shell member 974 includes opposite surfaces that engage an opposite edge of the shield 14 and an upper surface of the handle 6. An instruction manual 990 may be disposed along an interior surface of the second clam shell, with the manual providing the support surface. The manual may be secured with tabs or retainers 992.

The supports 982, 984, 986 ensure that the bolus simulator 82 is suspended in the cavity 978 such that the bolus simulator, and in particular the lubricated patches, do not contact any part of an interior surface of the carrying case, which may lead to premature depletion of the end of use feature if the surface has any moisture thereon. In addition, the suspension, or isolation of the bolus simulator, ensures and maintains the sanitary condition thereof while allowing the bolus simulator to dry after use. Vent holes 994 are provided and communicate between the cavity 978 and the exterior of the case, or ambient environment, such that moisture is not trapped but rather may evaporate. In one embodiment, the vent holes 978 are formed by mating openings in each of the first and second clam shells 972, 974. Snap features 996, or releasably latch features, are provide on the clam shells such that the case may be releasably latched in the closed position. Large tabs 998 are offset on the first and secon covers, and allow the user to grasp the tabs disengage the latch features 996 to and thereafter open the case. A hanging tab having a hook portion 1000 is disposed at one end of the case such that a retailer may easily display the device by engaging a rod. A line of weakness 1002, such as perforation, is made along the length of the hanging tab such that it may be easily removed by the end user.

In the embodiment of FIGS. 148A and B, 160, the entirety of the handle 6, tether 10 and intraoral bolus simulator 12, 82 are disposed between the first and second clam shell members 972, 974 when in the closed position. The first clam shell member 972 defines a second interior cavity 1004 positioned below the handle when the oral device is disposed on the first clam shell member when in said open position. The user may insert one or more fingers into the cavity 1004 so as to easily grasp or grip the handle and remove the oral device from the case.

In another embodiment, shown in FIGS. 154A and B, the handle 6 extends exteriorly outwardly from first and second clam shell covers 942, 944 when in the closed position. The covers 942, 944 form an opening 946, with mating annular flanges 948 that act as a positioning feature to locate the device. The first clam shell 942 includes a pair of upstanding flanges 952, 954 that extend into the cavity and support the tether along a recessed top edge portion. The bottom of the clam shell includes one or more tabs 958 or flanges that engage and support a bottom edge and front face of the shield 14. The flanges define a bottom support surface, with a protruding portion defining a stop for the front of the shield. An opposite clam shell member 944 includes a flange 962, also having a recessed top edge, that engages and traps the tether between the flanges 952, 954, 962 and also a plurality of tabs or flanges 958 that engage and locate the shield in the case. In this way, the bolus simulator may again be suspended in the cavity 948 free of any contact with an interior surface of the case 940. The clam shells, in combination, form the vent holes 920 that align with the vent holes 620 in the shield, thereby permitting an air passageway from the cavity 948 to the exterior of the case such that air may circulate and the bolus simulator may be dried out by way of evaporation after use. The first and second clam shell members also include a latch member 1008 on one of the clam shell members that engages a tab 1010 on the other, so as to provide a releasable engagement of the two clam shell member in a closed position (FIG. 154A).

Operation

In operation of the embodiment shown in FIG. 92, the oral device, and in particular the bolus simulator 148, is positioned on an affected/disfunctional side of the user's mouth, for example by a stroke. Using muscles on an unaffected side (by way of the rigid mandible), the user bites down on the bolus, with the bite force input applied to the sensor 152 resulting in a charge or current being delivered to the external electrodes 150, resulting in a mild oral electrical stimulation. The level of current or charge may be regulated through a control device to a predetermined level. The stimulation would provide real-time feedback to the neural system, thereby facilitating activation and potential modulation of the swallow related neural pathways.

The oral device may also be configured with, or operably coupled to, other feedback systems, including without limitation various visual and/or oral feedback systems such as a light, scaled numeric indicia, color gradations, sound output, or combinations thereof, that are indicative of the bite or tongue force applied by the user.

The oral device also may be used to register the tongue force of the user, for example when the device is positioned on the superior surface of the tongue, or alternatively cheek force when positioned along the side of the mouth, again with various biofeedback systems, including electrical stimulation, lights and sound corresponding to relative amounts of applied force. Any tongue manipulation (lateral, suck, push, pull) force may be a candidate for monitoring. The output results may also be recorded, manually or by a computer, to track progress.

In one embodiment, and referring to FIGS. 95 and 96, the bolus simulator 32 is positioned on the superior surface 300 of the rear tongue 302, that is, the region of the tongue surface medial to the molar teeth, or against the rear palate, with a flat surface of the simulator resting on the tongue. The mouth is then closed, with the bolus simulator 32 contacting both the superior surface of the tongue and the palate. The tongue and palate mucosa contact the outer coating so as to initiate a gradual release of any gustatory and thermal agents. Vibration of the bolus simulator may be initiated, and/or the user may be verbally cued (by the user, care giver or device) to prepare to swallow and then subsequently swallow. The tongue contains the bolus simulator by elevating around the bolus simulator at an anterior and lateral aspects. Due to its shape, size and position, the bolus simulator contacts the superior tongue surface, left and right lateral tongue margins and palate. In various embodiments, the bolus simulator stimulates both sides of the oral cavity/oropharynx, or only one side of the oral cavity. If pharyngeal swallowing is triggered, the tongue presses against the palate in an anterior-to-posterior direction, which may release a bolus, such as a fluid, from the inner core in some embodiments. The user then swallows the bolus. Users with upper dentures should remove the dentures prior to use to avoid any interference with stimulation of the sensory receptive fields on the palate.

The physical specifications of the bolus stimulator 32, 80, 82, 98 may stimulate the oral cranial nerve afferents. For example, when positioned on the superior surface 300 of the tongue, the bolus simulator may stimulate a variety of sensory receptors lining the tongue surface, as well as lining the hard and soft palates. The anterior ⅔ of the tongue receives somatic sensory innervations from the trigeminal (v) nerve, and taste sensation from the facial nerve (VII), and the glossopharyngeal extends into the anterior ⅔ of the tongue, particularly along the lateral tongue margin, with anasomoses between the IX and V nerves. In this way, the bolus simulator may stimulate the V, VII and IX afferent fibers that are critical for a number of oral sensorimotor behaviors including but not limited to normal food transport, mastication, taste, swallowing, speech production and salivation.

While the bolus simulator 32, 80, 82 may be positioned on the superior tongue surface 300 and maintained in a stationary position, the user, or caregiver, may also move the bolus simulator within the oral cavity by manually manipulating the handle. For example and without limitation, the bolus simulator may be rotated on the tongue surface, or displaced to make contact with the buccal cavity, hard and soft palates, sub-lingual region, tongue surface, and anterior facial pillar, the latter of which is believed to play a role in eliciting pharyngeal swallowing. Various approaches may also include stroking the bolus simulator along the tongue surface, which may excite both gustatory and somatosensory receptors. The user may also manipulate the bolus simulator as if it were a masticated piece of food, ready to be swallowed, with the tether preventing actual swallowing of the device. The simulator can also be treated like a lollypop, with the user practicing sucking motions. Flavoring of the bolus simulator may help the user to imagine or conjure that the bolus simulator is a real piece of masticated food, with the scented shield also serving a similar function due to the position of the shield positioned under the nose.

In use as shown in 54A and B, the bolus simulator shown in FIGS. 99 and 100 is positioned in the mouth relative to the teeth and jaw. The oral device targets the start of the pharyngeal swallow phase. The pharynx is in communication with both the esophagus and the larynx. The device also encourages the user to engage motor functions (chewing, tongue movement, etc.) that may facilitate triggering or initiation of the patterned pharyngeal swallow. The device may also be used by persons with oral preparatory stage dysfunction, such as those with cancer resection, without the oral preparatory phase. The portion of the device that extends between the teeth and lips of the user is as thin as possible to facilitate full closure of the mouth and occlusion of the teeth. At the same time, the shield 214 may be moved and located to position the bolus simulator 98 in the proper location in the mouth.

After the device is positioned, the user chews or sucks on the air intake conduits 208, acting as a pump, to inflate the bolus simulator 98 by forcing air through the valving mechanism 210 through an inlet into the interior volume, with the bolus simulator 98 positioned on the anterior of the tongue to prevent gagging. The bolus simulator may also be inflated by an external source, such as a squeeze tube or motorized pump. In an alternative embodiment, the user may suck on an air inlet to inflate the bolus simulator. Also in one embodiment, the air intake passageways may be integrally formed as part of the bolus simulator, rather than being spaced therefrom.

The user then squeezes the bolus simulator 98 with their tongue, with the chewing, sucking and squeezing engaging the motor neurons in the preparatory phase. In addition, any flavorful coating or surface texture may further stimulate the user. In response to pressure applied to the bolus simulator by the tongue during swallowing, air is forced out of the bolus simulator through the exhaust valve 228, or outlet, and into the mouth of the user, targeting for example the glossopharyngeal and/or superior laryngeal nerves. As the user squeezes the bolus simulator, due to the properties of the bladder such as the skin, the bolus simulator 98 distends out to the back of the tongue, promoting a tongue stripping wave associated with normal swallowing. As the bladder distends, the exhaust valve 228 releases the pressurized gas and directs it to the back of the throat, with the gas pulse creating a somatic stimulus on the site of the glossopharyngeal and superior laryngeal nerve receptive fields which are involved in the triggering of the pharyngeal swallow. The gas pulses may provide a sensation that there is a piece of food in the back of the user's mouth ready to be swallowed, and may trigger the nerves that initiate the involuntary portion of the swallowing sequence. The bladder 98, now flat and empty, retracts upon release of the tongue pressure to its original shape and position, ready for subsequent inflation and deflation cycles to facilitate reestablishment of the neural connections required for a normal swallow. The operation may then be repeated. No fluid, gel or foodstuff is released or positioned in the mouth during operation. Instead, the device simulates a bolus to trigger the patterned response.

Referring to FIGS. 100A-F, the squeeze bulb 272 is manipulated to force air through the conduit 270, 264, one-way valve 266 and into the bolus simulator 98. The air may then be released from the bolus simulator 98 by manipulation of the tongue, or by applying a pressure with the squeeze bulb that is sufficiently large enough to overcome the pressure release valve 228 so as to thereby open that valve and emit an air pulse from the bolus simulator.

Referring to FIGS. 42, 43 and 54A and B, the user self-inflates the bolus simulator through the two-way valve 222 by a sucking action. The valve 222 holds a predetermined pressure of fluid, or air in this instance. Upon a swallowing action, pressure from the tongue overcomes the predetermined pressure of the exhaust valve to release the air from the bolus simulator 98.

Figure 32A:
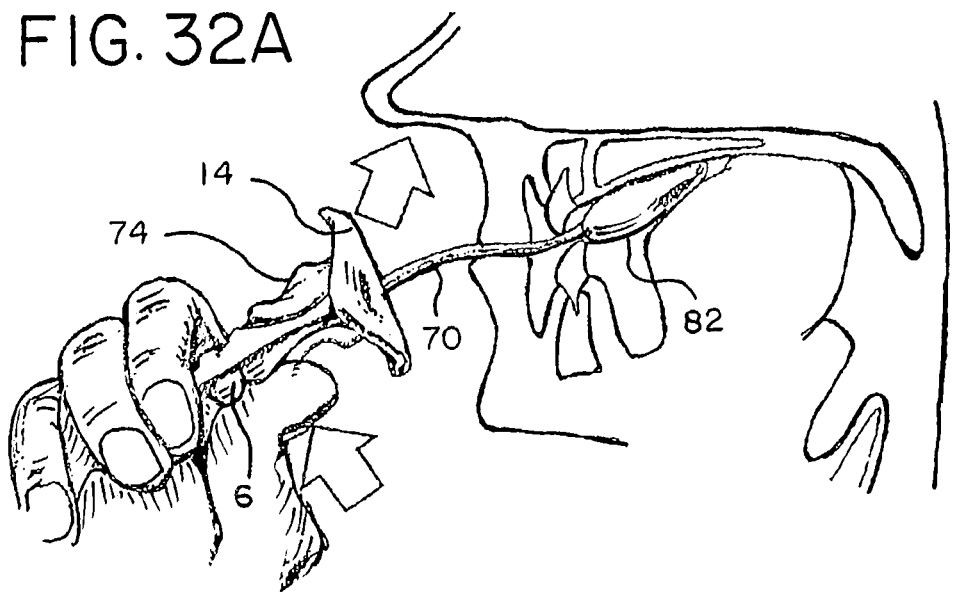
FIG. 32A is a side view of an oral device with a fluid reservoir being manipulated a user.
Figure 32B:
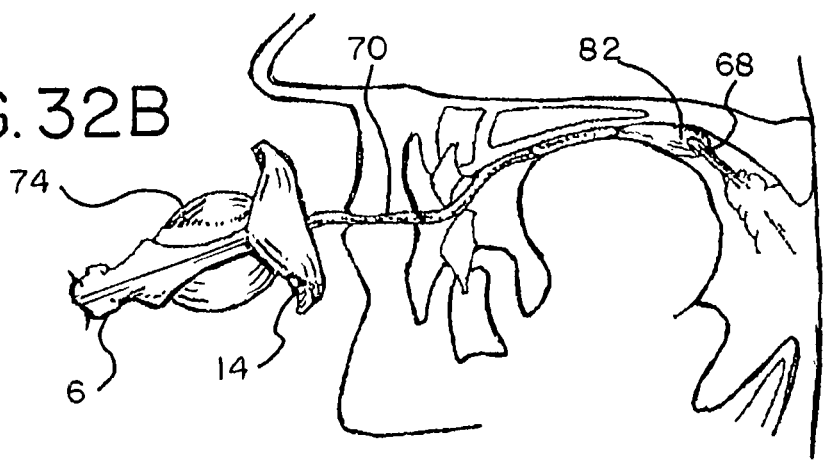
FIG. 32B is a side view of the oral device shown in FIG. 32A with fluid being displaced to the fluid reservoir and a gas passing through a gas outlet at the rear of the user's mouth.
Figure 33:
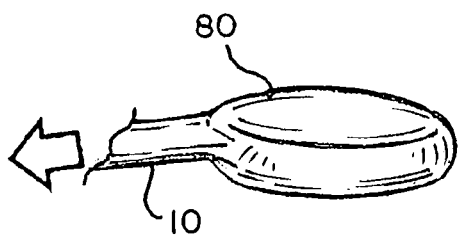
FIG. 33 is a partial perspective view of an alternative embodiment of an oral device.
Figure 34:
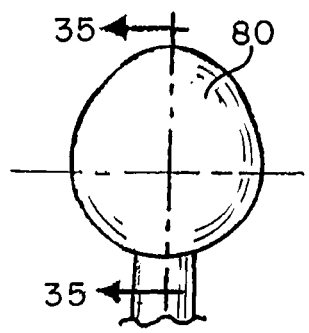
FIG. 34 is a top view of the oral device shown in FIG. 33.
Figure 35:
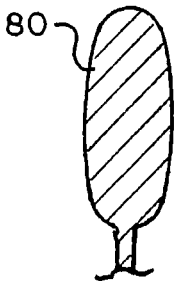
FIG. 35 is a cross-sectional view of the oral device shown in FIG. 34 taken along line 35-35.
Figure 48A:
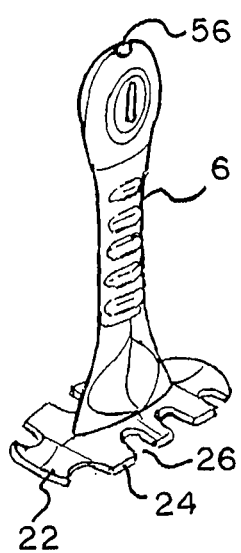
FIGS. 48A-D are various views of one embodiment of an oral device.
Figure 48B:
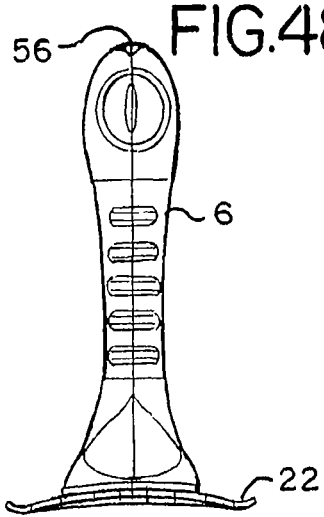
Figure 48C:
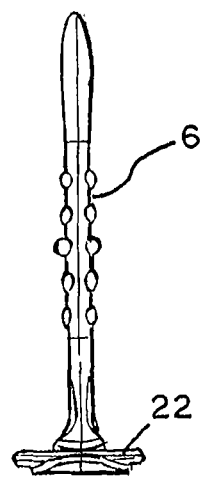
Figure 48D:
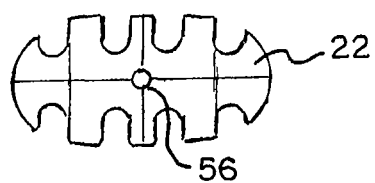
Figure 49A:
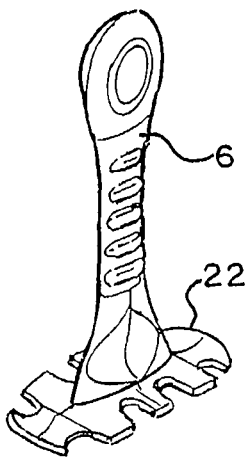
FIGS. 49A-D are various views of one embodiment of an oral device.
Figure 49B:
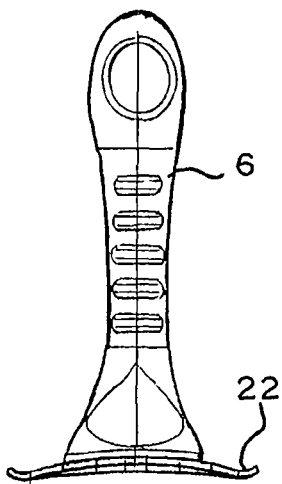
Figure 49C:
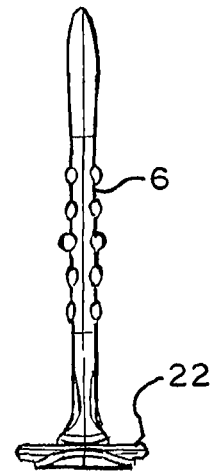
Figure 49D:
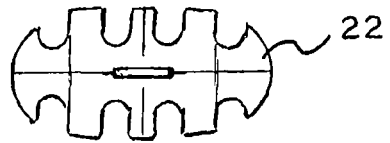
Figure 50A:
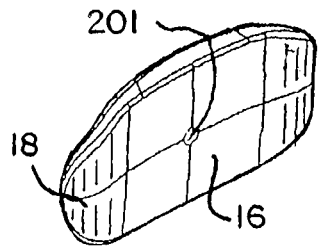
FIGS. 50A-E are various views of one embodiment of a shield for an oral device.
Figure 50B:
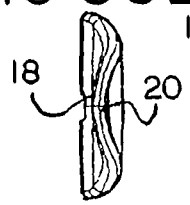
Figure 50C:
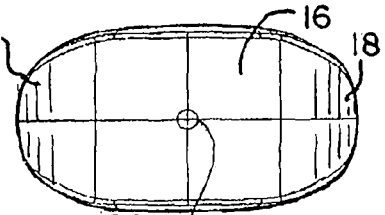
Figure 50D:
Figure 50E:
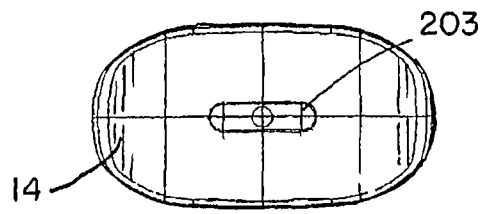
Figure 51A:
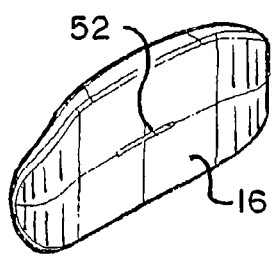
FIGS. 51A-E are various views of one embodiment of a shield for an oral device.
Figure 51C:
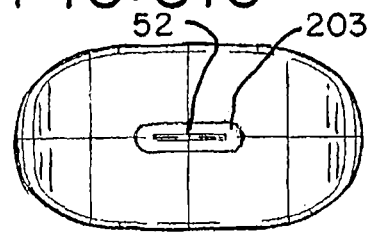
Figure 51D:
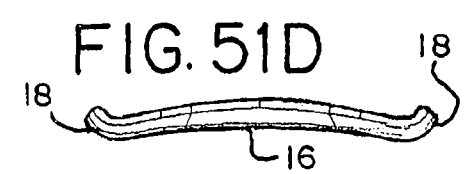
Figure 51B:
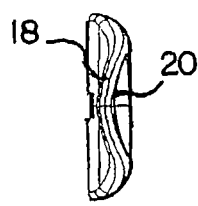
Figure 51E:
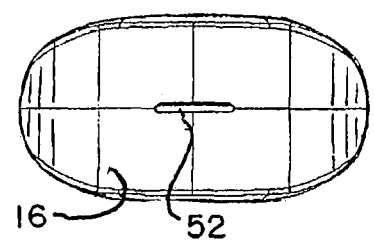
Figure 55A:
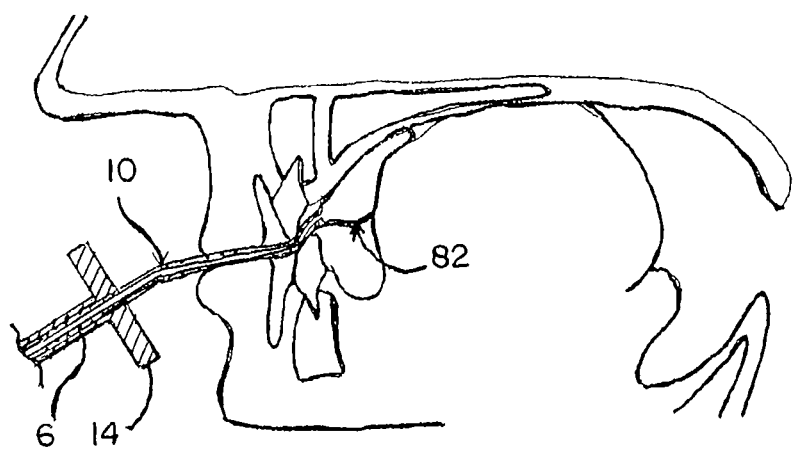
FIGS. 55A and B are cross-sectional views of a gas pulse and non-gas pulse oral devices in operation.
Figure 55B:
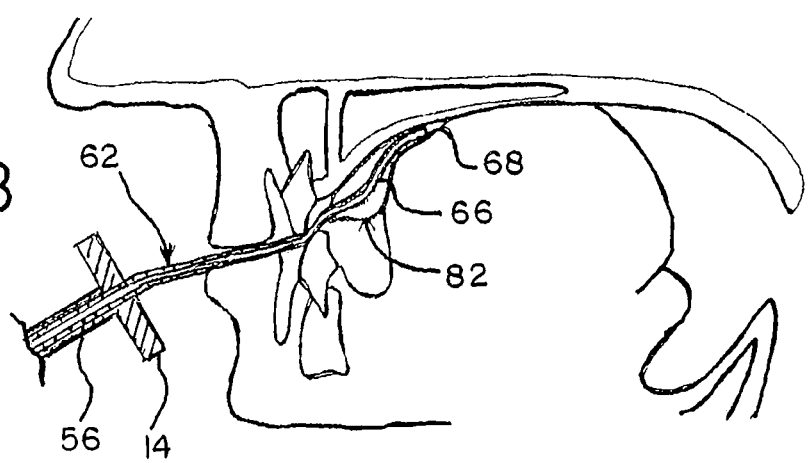
Figure 56A:
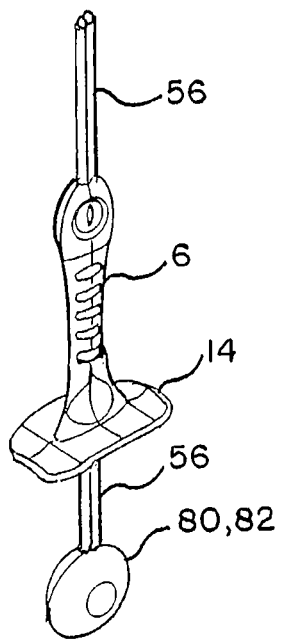
FIG. 56A-D are various views of one embodiment of an oral device.
Figure 56B:
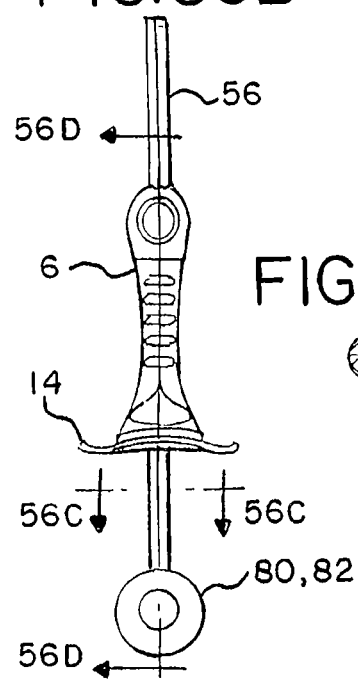
Figure 56C:
Figure 56D:
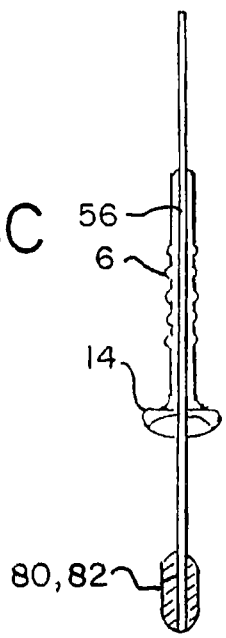
Figure 68:
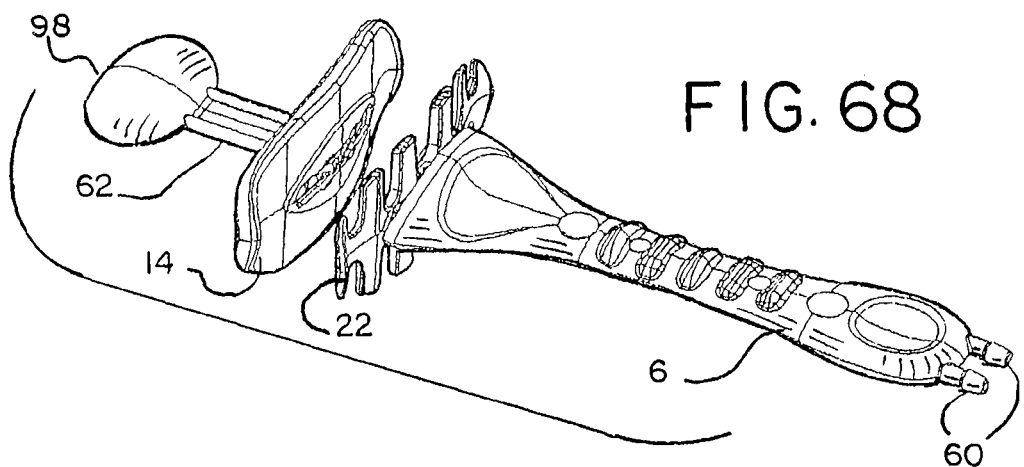
FIG. 68 is an exploded view of an alternative embodiment of an oral device.
Figure 69:
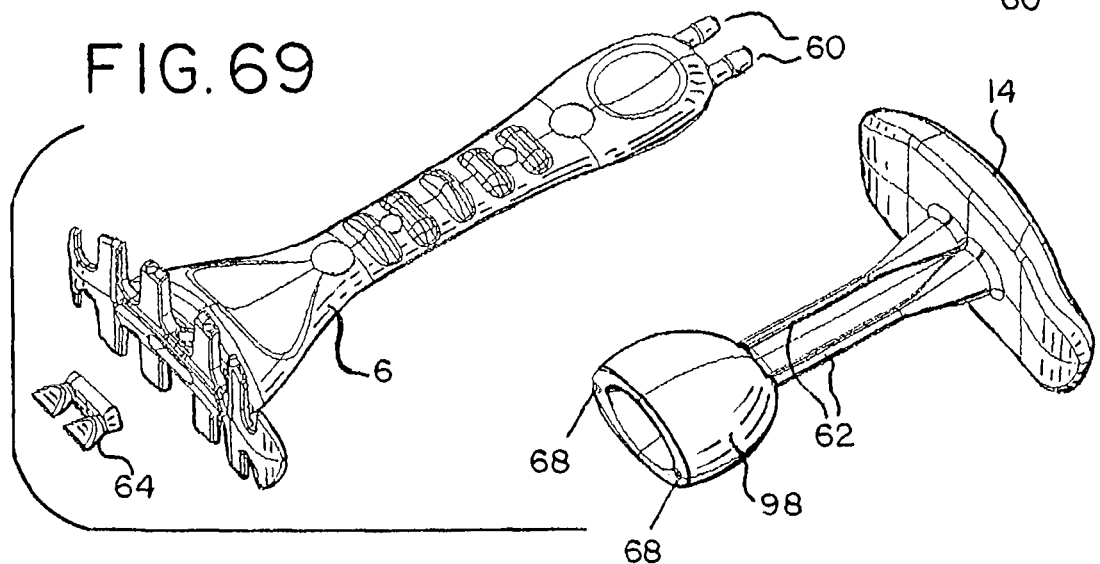
FIG. 69 is an exploded view of an alternative embodiment of an oral device.

Referring to FIGS. 32A and B, during use, the user may actuate the reservoir 74 by pushing fluid from the reservoir 74 through the inlet to the interior volume 72 of the bolus simulator. The bolus simulator may also be filled from the reservoir 74 by way of a sucking action by the user, acting as a pump. The shield 14 may be scented. As the user squeezes the bolus simulator 98, due to the properties of the bladder such as the skin, the bolus simulator distends out to the back of the tongue, promoting a tongue stripping wave associated with normal swallowing. As the bolus simulator collapses, the fluid is forced from the interior volume 72 through the outlet and back into the reservoir 74. At the same time, gas may be directed through the gas outlet 68, segregated from the interior volume, to the back of the throat, with the gas pulse creating a touch sensation on the site of the glossopharyngeal nerve and/or the superior laryngeal nerve, which is the final trigger for the pattern response and a pharyngeal swallow. The bolus simulator 82, with its interior volume diminished, flattens and retracts upon release of the tongue pressure to its original position, ready for subsequent filling and evacuation cycles to facilitate reestablishment of the neural connections required for a normal swallow. No liquid, gel or foodstuff is released or positioned in the mouth during operation, but rather travel back and forth between the bolus simulator and the reservoir. Instead, the device simulates a bolus to trigger the patterned response.

Referring to FIGS. 27-32, during swallowing, the fluid may flow from the bolus simulator 82 to the reservoir 74, thereby allowing the bolus simulator interior volume to be substantially evacuated and cuing the user that there is no more food. This action may be combined with gas pulses being automatically directed to portions of the mouth due to the same stripping movement of the tongue. The ability of the fluid to escape from the bolus simulator to the reservoir provides a safety function preventing a bursting of the bolus simulator in the event that a user inadvertently applies an excessive pressure to the bolus simulator.

Referring to FIGS. 26A and B and 114, the user's tongue manipulates the liquid filled bolus simulator 82 to position it as if it were going to be swallowed. A scent may be emitted from the shield 14 below the user's nose, which may further aid in saliva generation and/or induce swallowing. The tongue moves in a stripping wave movement that moves the bolus simulator toward the back of the mouth, with the one-way exhaust valve 88 then releasing the gas to the designated area of the user's mouth and throat. Alternatively, the gas may be delivered through a conduit, not constrained by valves, from an external gas supply, for example by delivering gas pulses through the ports 68. As shown in FIG. 94, conduits 192 may extend laterally from the bolus simulator and deliver a gas pulse to the sides of the user's mouth.

The deformable bolus simulator 82, whether variable in volume or when configured as a hydrostat as shown in FIG. 114, provides an opportunity for subtle movements of the tongue to be met by changes in the local sensory environment, which in turn may facilitate changes in tongue posture/position and corresponding oral sensory input. The user may participate in intensive oral sensorimotor transformations by maintaining the deformable bolus simulator on the superior surface of the tongue, and thereby simulate various properties of a food/liquid bolus to be swallowed. The device may also be used as a preventative measure, for example to maintain a strong and healthy swallow function in the elderly population, for example by helping them to maintain their ability to eat and drink.

Referring to the embodiment of FIGS. 44 and 45, the oral device includes conduits 112 for delivering air pulses, together with positioning a bolus simulator in the mouth of the user. The conduits and functioning of the device are disclosed and described in U.S. application Ser. Nos. 13/040,048 and 13/040,058, both filed Mar. 3, 2011, the entire disclosures of which are hereby incorporated herein by reference. The bolus simulator may be configured as any of the embodiments disclosed herein. In this embodiment, the air pulses may be directed to areas of the mouth and throat at locations spaced from the bolus simulator.

In an alternative mode of operation, and referring to FIGS. 90-91, the bolus simulator 82 is positioned between the molars 400 on an affected side of the mouth, for example a stroke victim suffering from dysphagia. Using the muscles on the unaffected side of the mouth, the bolus simulator 82 is compressed between the teeth 400, causing the simulator to be distended laterally. The distended portion applies a force to the side of the cheek on one side, and to the side of the tongue 302 on the other, thereby providing a tactile stimulation associated with a chewing action that may facilitate neural activation and potentially neural modulation with associated behavioral improvement in oral, chewing and swallowing functions.

Referring to FIGS. 148A-B, 154A-B and 159-C, the oral device 2 may be sold in the carrying case 940, 970. The user, care-giver or patient may release the latch 996, 1008, open the carrying case, and extract the oral device 2. The oral device 2 may then be manipulated by inserting the bolus simulator 82 into the oral cavity, as explained above. After use, the oral device 2 may be reinserted into the carrying case 940, 970, which may be closed and releasably latched, with the vent holes 920, 620, 994 permitting drying of the oral device within the carrying case. This process may be repeated as appropriate, for example per a prescribed medical protocol.

After a predetermined number of uses, or period of time within the oral cavity, the oral device 2, and the bolus stimulus 82 in particular, may provide indicia to the user that the device has reached its end of life, and should be replaced. For example, as explained above, the water soluble particles 932 may bloom out (FIG. 159B) of the lubricated patches 924 during use, with the silicone matrices 934 providing a rough surface 936, or tactile indicia, once the water soluble thermo plastic particles are completely depleted (FIG. 159C). The appearance (visual and/or tactile) of the rough surface provides an indication to the user, caregiver and/or patient that it is time to replace the device.

Assembly and Manufacture

Figure 1A:
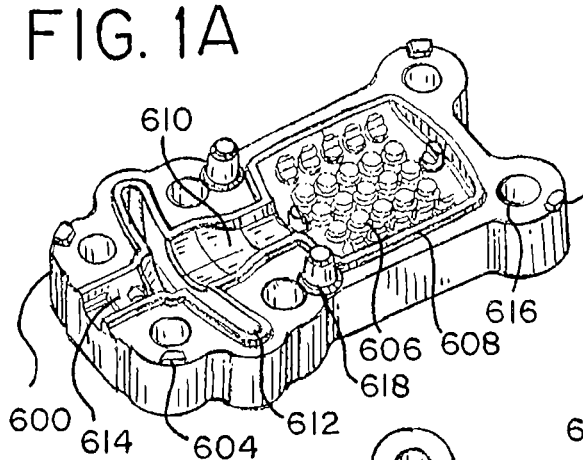
FIGS. 1A and B are perspective views of two mold components.
Figure 1B:
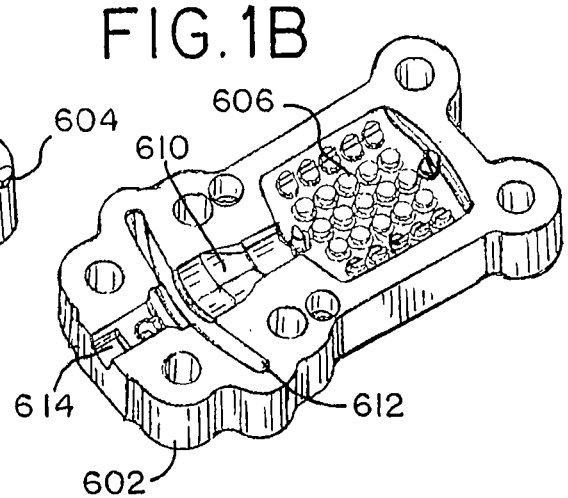
Figure 2:
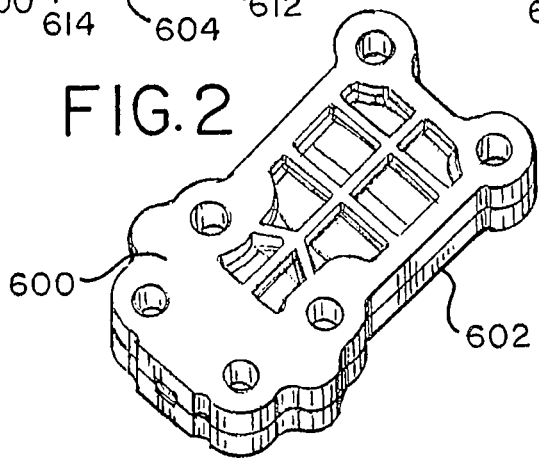
FIG. 2 is a perspective view of the mold components in FIG. 1 in a closed configuration.

FIGS. 1-17 show various molds used to manufacture various embodiments of oral devices herein described. Referring to FIGS. 1A and B, a pair of mold halves 600, 602 are shown. A first mold half 600 has mold stand offs 604, a bolus simulator cavity 606 with a seal-off lip 608 formed around a perimeter thereof, tether and shield cavities 610, 612 and a cavity 614 for an extraoral coupling member.

Various bolt holes 616 and alignment pins 618 are provided to interface and couple the two mold halves.

Figure 3:
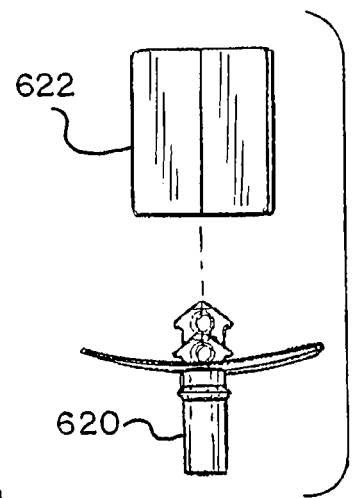
FIG. 3 is an exploded view of a pair of insert components making up portions of an oral device.
Figure 4:
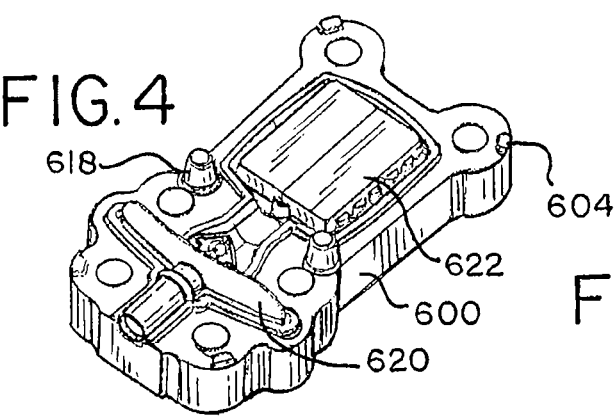
FIG. 4 is a perspective view of the insert components of FIG. 3 disposed in one of the mold halves of FIG. 1.
Figure 6:
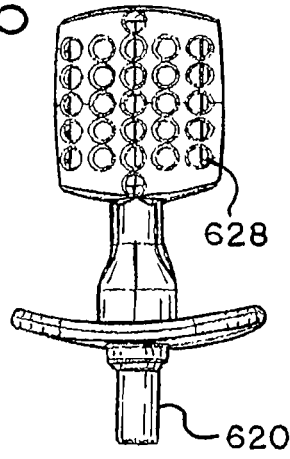
FIG. 6 is a perspective view of one embodiment of an oral device.
Figure 5:
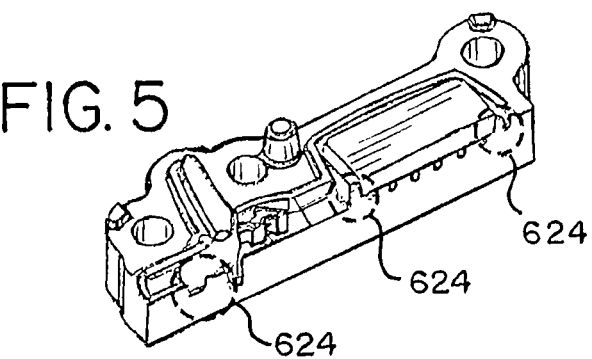
FIG. 5 is a cross-sectional perspective view of FIG. 3.
Figure 27:
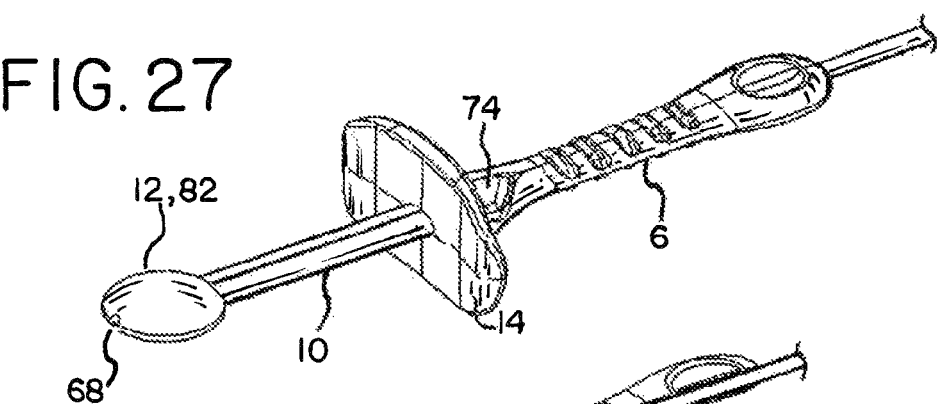
FIG. 27 is a perspective view of an embodiment of an oral device having a liquid filled bolus simulator and gas passageway.
Figure 28:
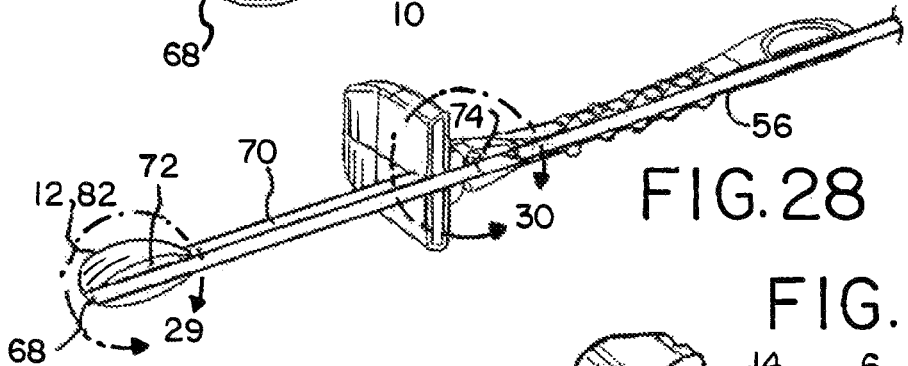
FIG. 28 is a cross-sectional view of the oral device shown in FIG. 27.
Figure 29:
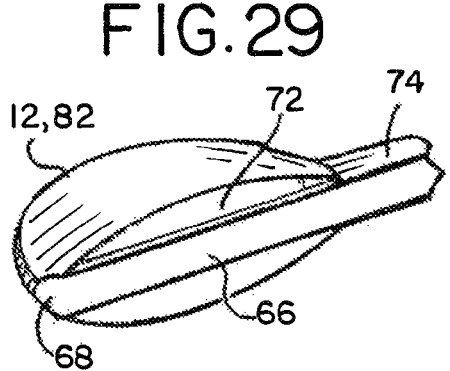
FIG. 29 is an enlarged view of the bolus simulator and gas passageway taken along line 29 in FIG. 27.
Figure 30:
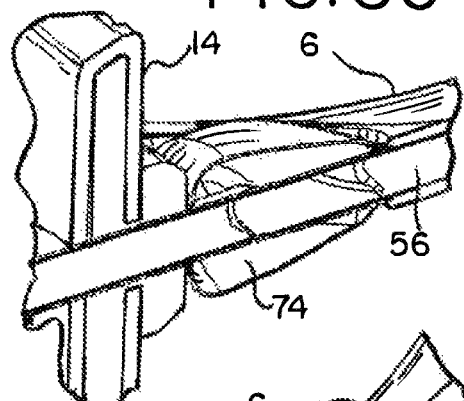
FIG. 30 is an enlarged view of fluid reservoir taken along line 29 in FIG. 27.
Figure 31:
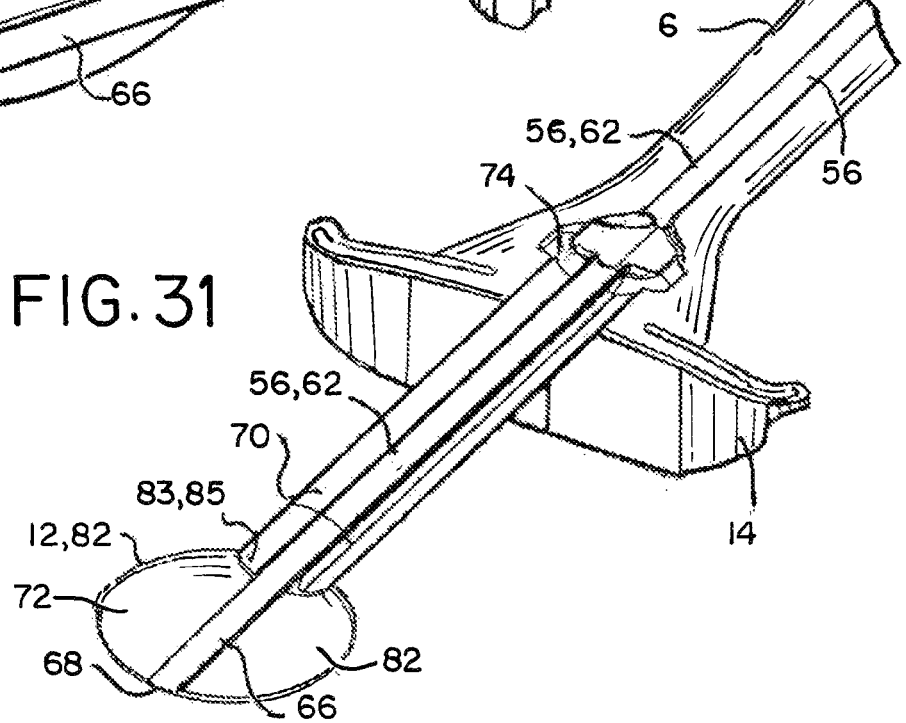
FIG. 31 is an alternative, partial cross-sectional view of the oral device shown in FIG. 27.

In operation, overmolding operations may be employed to form the intraoral portions, extraoral portions, and/or to join the intraoral and extraoral portions. For example, as shown in FIGS. 3-5, a handle adapter 620 and flavored core 622 are disposed as inserts between the mold parts 600, 602. A material, such as RTV Silicone, is then overmolded so as to encapsulate those components. As shown in FIG. 5, insert locators 624 position the core 622 and adapter 620 in the mold. The mold halves 600, 602 define the shape and contour of the bolus simulator, and may provide openings, for example, to the flavored inner core as shown in FIG. 6. The handle adapter 620, or extraoral coupling member may be coupled to a handle 6, for example with a set screw, snap-fit or interference fit. Mold gates and vents are provided in one of the mold halves, with the perimeter ridge providing a positive seal-off at the mold parting lines.

Alternatively, as shown FIGS. 7A-C, a mold configuration is shown with a handle adapter 630, but wherein the bolus simulator is formed as a solid, homogenous component. Referring to FIGS. 8A-C, a handle insert 632 may be positioned between the mold halves with a shield and bolus simulator being overmolded over the support structure of the handle insert 632. A handle 6 and shield 14 is then coupled to the insert 632 as shown in FIG. 9, for example by sliding the handle onto the insert.

To provide for separable mold halves, and referring to FIG. 10, a 7 degree ramp cavity seal-off 301 may be provided, which allows clamping bolts to be oriented substantially perpendicular to the mold parting lines. A removeable piece 303 includes guides allowing disassembly form the main mold components 305. In addition, dovetail locking interfaces 640, shown in FIGS. 11 and 12, provide an interlocking mechanism between a pair of first mold halves 642 used to mold the bolus simulator, and a system of second mold components 644 used to mold the shield. Alternatively, as shown in FIGS. 13 and 14, the first and second pairs of mold halves may be coupled with bolts 646 extending perpendicular to the first set of clamping bolts 648.

With respect to an embodiment incorporating a self-inflating bolus simulator, as shown in FIGS. 15, 16 and 18, the handle 6 may be made of cast urethane, with a pair of fluid conduits 56 formed interiorly of the handle. Each conduit has an inlet port 60 formed adjacent a distal end of the handle. As shown in FIGS. 17A and B, a pair of intermediate mold halves 660, 662 are used, with a gate 664 and a vent 668 communicating with the mold cavity. A core 670, including a pair of metal rods 672 and an end piece 674 for the cutout for the center of the shield structure, are disposed between the mold halves, with paths 663 provided for the metal rods 672 and a pocket 667 for the insert 674. After the handle is molded, a pair of one-way inlet valves 64, shown as duck-bill valves in FIG. 20, are insert molded with a mold clamped over the handle. The valves are formed by using cores 680 (one shown) that are inserted into the handle opening prior to closing the mold halves around the handle as shown in FIG. 22. After the valves 64 are molded, a slit is cut in the end of each valve, for example using a razor. The cores 680 are then extracted through the slit. The final step is to mold the bolus simulator using a lost core wax insert 682, shown in FIG. 21, to form the inside contour as well as the one-way exhaust valve, configured as a duck bill valve. The wax core 682 is molded separately.

In some embodiments, the oral device, including the handle, tether, shield and bolus simulator are constructed as an inseparable assembly with overmolded silicone subcomponents, which may provide desired material strengths and durabilities at a minimum cost by eliminating some post molding assembly. Alternatively, as disclosed, one or more, including all, of the bolus simulator, tether and shield may be separable, removable and replaceable, for example by replacing one or more components that have lost their flavouring.

In some embodiments, the oral device has both lateral and vertical symmetry which helps to eliminate ambiguity in device placement in the user's mouth, although it should be understood that devices may be constructed without such symmetry to address additional functionalities. It should be understood that one or more, including all, of the bolus simulator, tether and shield components may be flavoured.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An oral device comprising:
   an intraoral bolus simulator comprising an fluid filled bulb portion having opposite faces;
   first and second lubricated patches disposed on said opposite faces, said lubricated patches transformable in response to an application of a liquid from a first state, wherein said lubricated patches each comprise water soluble thermoplastic particles suspended in a silicone matrix, to a second state, wherein said water soluble thermoplastic particles are depleted from said silicone matrix;
   wherein an exterior surface of said lubricated patch is transitionable from a smooth surface in said first state to a rough surface in said second state in response to said water soluble thermoplastic particles being depleted from said matrix.

2. The oral device of claim 1 is transformable from said first state to said second state in response to contact from a liquid.

3. The oral device of claim 1 wherein said bulb portion comprises a peripheral side wall disposed between and connecting said opposite faces, wherein said peripheral side wall comprises an annular reinforcing rib extending around said peripheral side wall.

4. The oral device of claim 1 further comprising a tether coupled to said intraoral bolus simulator, wherein said tether comprises a core and a skin surrounding said core, wherein said skin comprises enlarged side portions surrounding opposite sides of said core.

5. The oral device of claim 4 wherein said skin comprises middle portions extending between said enlarged side portions on opposite faces of said core, wherein said middle portions define a first thickness less than a second thickness of said enlarged side portions.

6. The oral device of claim 4 further comprising a handle extending in an opposite direction from said tether, and a shield extending radially at a junction between said tether and said handle.

7. The oral device of claim 6 wherein said shield comprises a pair of holes formed therethrough.

8. A method of stimulating an oral cavity comprising:
   disposing an intraoral bolus simulator in an oral cavity of a user, wherein said intraoral bolus simulator comprises an fluid filled bulb portion having opposite faces, and first and second lubricated patches disposed on said opposite faces, said lubricated patches each comprising water soluble thermoplastic particles suspended in a silicone matrix;

presenting a smooth surface to said user with said lubricated patches;

contacting said lubricated patches with saliva and thereby depleting said water soluble thermoplastic particles from said silicone matrix; and presenting a rough surface to said user with said lubricated patches after said water soluble thermoplastic particles are depleted from said silicone matrix.

9. The method of claim 8 further wherein said disposing said intraoral bolus simulator in said oral cavity comprises supporting said intraoral bolus simulator with a handle and a tether, wherein a shield extends radially from the junction of the handle and tether and is disposed outside of the oral cavity, wherein said intraoral bolus simulator, handle, shield and tether form an oral device, and further comprising removing said intraoral bolus simulator from a carrying case prior to said disposing said intraoral bolus simulator in said oral cavity, wherein said intraoral bolus simulator is suspended in said carrying case free of any contact with said carrying case prior to said removing said intraoral bolus simulator from said carrying case.

10. The method of claim 9 further comprising reinserting said intraoral bolus simulator in said carrying case before said depleting all of said water soluble thermoplastic particles from said silicone matrix, and drying said intraoral bolus simulator in said carrying case by providing air passageways from an exterior of said carrying case to an interior cavity thereof.

* * * * *